United States Patent
Pantelopoulos et al.

(10) Patent No.: US 12,070,297 B2
(45) Date of Patent: *Aug. 27, 2024

(54) PHOTOPLETHYSMOGRAPHY-BASED PULSE WAVE ANALYSIS USING A WEARABLE DEVICE

(71) Applicant: Fitbit, Inc., San Francisco, CA (US)

(72) Inventors: Alexandros A. Pantelopoulos, El Cerrito, CA (US); Andrew Larsen Axley, Bend, OR (US)

(73) Assignee: FITBIT, INC., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/316,746

(22) Filed: May 12, 2023

(65) Prior Publication Data
US 2023/0277075 A1    Sep. 7, 2023

Related U.S. Application Data

(63) Continuation of application No. 17/196,983, filed on Mar. 9, 2021, now Pat. No. 11,684,281, which is a
(Continued)

(51) Int. Cl.
*A61B 5/02* (2006.01)
*A61B 5/00* (2006.01)
(Continued)

(52) U.S. Cl.
CPC ........ *A61B 5/02438* (2013.01); *A61B 5/0059* (2013.01); *A61B 5/02007* (2013.01);
(Continued)

(58) Field of Classification Search
CPC .............. A61B 5/02438; A61B 5/0059; A61B 5/02108; A61B 5/02416; A61B 5/6831; A61B 5/7203; A61B 5/7285
See application file for complete search history.

(56) References Cited

U.S. PATENT DOCUMENTS 6,331,162 B1    12/2001  Mitchell
6,583,369 B2    6/2003   Montagnino et al.
(Continued)

FOREIGN PATENT DOCUMENTS

EP    1 721 237 A1    8/2012

OTHER PUBLICATIONS

Fuke et al., "Blood Pressure Estimation from Pulse Wave Velocity Measured on the Chest," Thirty-fifth Annual International Conference of the Institute of Electrical and Electronics Engineers Engineering in Medicine and Biology Society, Osaka, Japan, Jul. 2-3, 2013, pp. 6107-6110.
(Continued)

*Primary Examiner* — Eric D. Bertram
(74) *Attorney, Agent, or Firm* — DORITY & MANNING P.A.

(57) ABSTRACT

Disclosed are devices and methods for non-invasively measuring arterial stiffness using pulse wave analysis of photoplethysmogram data. In some implementations, wearable biometric monitoring devices provided herein for measuring arterial stiffness have the ability to automatically and intelligently obtain PPG data under suitable conditions while the user is engaged in activities or exercises. In some implementations, wearable biometric monitoring devices are provided herein with the ability to remove PPG data variance caused by factors unrelated to arterial stiffness. In some implementations, wearable biometric monitoring devices have the ability to perform PWA while accounting for the user's activities, conditions, or status.

19 Claims, 23 Drawing Sheets

Related U.S. Application Data continuation of application No. 15/406,501, filed on Jan. 13, 2017, now Pat. No. 10,973,422.

(60) Provisional application No. 62/286,224, filed on Jan. 22, 2016.

(51) Int. Cl.
  *A61B 5/021*     (2006.01)
  *A61B 5/024*     (2006.01)
  *A61B 5/0205*    (2006.01)

(52) U.S. Cl.
  CPC ...... *A61B 5/02108* (2013.01); *A61B 5/02416* (2013.01); *A61B 5/6831* (2013.01); *A61B 5/7203* (2013.01); *A61B 5/7285* (2013.01); *A61B 5/002* (2013.01); *A61B 5/02055* (2013.01); *A61B 5/4812* (2013.01); *A61B 5/681* (2013.01); *A61B 5/7225* (2013.01); *A61B 5/7264* (2013.01); *A61B 5/746* (2013.01); *A61B 2503/10* (2013.01); *A61B 2560/0462* (2013.01); *A61B 2562/043* (2013.01); *A61B 2562/16* (2013.01); *A61B 2562/182* (2013.01); *A61B 2562/185* (2013.01)

(56) References Cited

U.S. PATENT DOCUMENTS

| | | | |
|---|---|---|---|
| 7,479,111 | B2 | 1/2009 | Zhang et al. |
| 8,313,439 | B2 | 11/2012 | McCombie et al. |
| 10,201,312 | B2* | 2/2019 | Kumar ............ A61B 5/02 |
| 10,973,422 | B2* | 4/2021 | Pantelopoulos ... A61B 5/02108 |
| 11,179,049 | B2 | 11/2021 | Niehaus et al. |
| 11,457,824 | B2 | 10/2022 | Yuen |
| 11,589,758 | B2 | 2/2023 | Pantelopoulos et al. |
| 11,684,281 | B2* | 6/2023 | Pantelopoulos ... A61B 5/02108 600/480 |
| 2005/0143665 | A1* | 6/2005 | Huiku ............ A61B 5/4035 600/500 |
| 2008/0043128 | A1 | 2/2008 | Poonen et al. |
| 2008/0200819 | A1 | 8/2008 | Lynn et al. |
| 2008/0262361 | A1 | 10/2008 | Gutfinger et al. |
| 2009/0105556 | A1 | 4/2009 | Fricke et al. |
| 2009/0326386 | A1 | 12/2009 | Sethi et al. |
| 2010/0318578 | A1 | 12/2010 | Treu et al. |
| 2010/0331145 | A1 | 12/2010 | Lakovic et al. |
| 2011/0032105 | A1 | 2/2011 | Hoffman et al. |
| 2012/0136261 | A1 | 5/2012 | Sethi et al. |
| 2012/0136605 | A1 | 5/2012 | Addison et al. |
| 2012/0274508 | A1 | 11/2012 | Brown et al. |
| 2013/0106684 | A1 | 5/2013 | Weast et al. |
| 2013/0310700 | A1 | 11/2013 | Wiard et al. |
| 2014/0012117 | A1 | 1/2014 | Mensinger et al. |
| 2014/0012147 | A1 | 1/2014 | Li et al. |
| 2014/0051941 | A1 | 2/2014 | Messerschmidt |
| 2014/0099614 | A1 | 4/2014 | Hu et al. |
| 2014/0142403 | A1 | 5/2014 | Brumback et al. |
| 2014/0155767 | A1 | 6/2014 | Fukuda et al. |
| 2014/0213863 | A1* | 7/2014 | Loseu ............ A61B 5/725 600/324 |
| 2014/0275854 | A1 | 9/2014 | Venkatraman et al. |
| 2014/0288435 | A1 | 9/2014 | Richards et al. |
| 2014/0358012 | A1* | 12/2014 | Richards ............ H04W 4/027 600/479 |
| 2015/0032009 | A1 | 1/2015 | LeBoeuf et al. |
| 2015/0051500 | A1 | 2/2015 | Elliott et al. |
| 2015/0112606 | A1* | 4/2015 | He ............ A61B 5/02055 702/19 |
| 2015/0164351 | A1* | 6/2015 | He ............ A61B 5/0285 702/19 |
| 2015/0182132 | A1* | 7/2015 | Harris ............ A61B 5/318 340/870.01 |
| 2015/0366469 | A1* | 12/2015 | Harris ............ A61B 5/0022 600/301 |
| 2015/0374249 | A1 | 12/2015 | Elliott et al. |
| 2016/0058308 | A1* | 3/2016 | Robinson ........ A61B 5/02125 600/479 |
| 2016/0058375 | A1 | 3/2016 | Rothkopf |
| 2016/0106333 | A1* | 4/2016 | Kang ............ A61B 5/021 600/301 |
| 2016/0148531 | A1* | 5/2016 | Bleich ............ A61B 5/486 434/247 |
| 2016/0150978 | A1* | 6/2016 | Yuen ............ A61B 5/0205 600/301 |
| 2016/0213331 | A1 | 7/2016 | Gil et al. |
| 2016/0261974 | A1 | 9/2016 | Arrizza |
| 2016/0345845 | A1* | 12/2016 | Ravid ............ A61B 5/021 |
| 2017/0024555 | A1 | 1/2017 | Flitsch et al. |
| 2017/0071516 | A1* | 3/2017 | Bhagat ............ A61B 5/0261 |
| 2017/0164904 | A1* | 6/2017 | Kirenko ............ G06T 7/254 |
| 2017/0172433 | A1* | 6/2017 | Olivier ............ A61B 5/0002 |
| 2017/0172510 | A1* | 6/2017 | Homyk ............ A61B 5/721 |
| 2017/0209053 | A1 | 7/2017 | Pantelopoulos et al. |
| 2017/0209055 | A1 | 7/2017 | Pantelopoulos et al. |
| 2017/0245769 | A1 | 8/2017 | Niehaus et al. |
| 2017/0251935 | A1 | 9/2017 | Yuen et al. |
| 2017/0281024 | A1* | 10/2017 | Narasimhan ........ A61B 5/681 |
| 2017/0347895 | A1 | 12/2017 | Wei et al. |
| 2018/0078156 | A1 | 3/2018 | Chen et al. |
| 2018/0146869 | A1* | 5/2018 | Zhang ............ A61B 5/7264 |
| 2018/0279965 | A1 | 10/2018 | Pandit et al. |

OTHER PUBLICATIONS

Gibbs et al. "Reducing Motion Artifact in Wearable Bio-Sensors Using MEMS Accelerometers for Active Noise Cancellation", 2005 American Control Conference, Portland, Oregon, United States, Jun. 8-10, 2005.

Junior et al., "Estimation of Blood Pressure and Pulse Transit Time Using Your Smartphone", 2015 Euromicro Conference on Digital System Design, Institute of Electrical and Electronics Engineers, Funchal, Madeira, Portugal, Aug. 26-28, 2015, pp. 173-180.

Nelson et al., "Noninvasive Measurement of Central Vascular Pressures with Arterial Tonometry: Clinical Revival of the Pulse Pressure Waveform?", Mayo Clinic Proceedings, May 2010, vol. 85, pp. 460-472.

Payne et al., "Pulse Transit Time Measured from the ECG: An Unreliable Marker of Beat-to-Beat Blood Pressure", Journal of Applied Physiology, Jan. 2006, vol. 100, pp. 136-141.

U.S. Final Office Action dated Feb. 3, 2021, in U.S. Appl. No. 15/452,047.

U.S. Final Office Action dated Jul. 21. 2020, in U.S. Appl. No. 15/414,425.

U.S. Final Office Action dated Mar. 11, 2020, in U.S. Appl. No. 15/406,501.

U.S. Final Office Action dated Mar. 16, 2020, in U.S. Appl. No. 15/442,559.

U.S. Final Office Action dated May 5, 2020, in U.S. Appl. No. 15/452,047.

U.S. Final Office Action dated Oct. 9, 2020, in U.S. Appl. No. 15/406,501.

U.S. Notice of Allowance dated Dec. 10, 2021, in U.S. Appl. No. 15/414,425.

U.S. Notice of Allowance dated Dec. 9, 2020, in U.S. Appl. No. 15/406,501.

U.S. Office Action dated Apr. 6, 2020, in U.S. Appl. No. 15/414,425.
U.S. Office Action dated May 20, 2020, in U.S. Appl. No. 15/406,501.
U.S. Office Action dated Oct. 1, 2019, in U.S. Appl. No. 15/452,047.
U.S. Office Action dated Sep. 4, 2019, in U.S. Appl. No. 15/442,559.
U.S. Office Action dated Sep. 27, 2019, in U.S. Appl. No. 15/406,501.
U.S. Office Action dated Sep. 30, 2020, in U.S. Appl. No. 15/442,559.

* cited by examiner

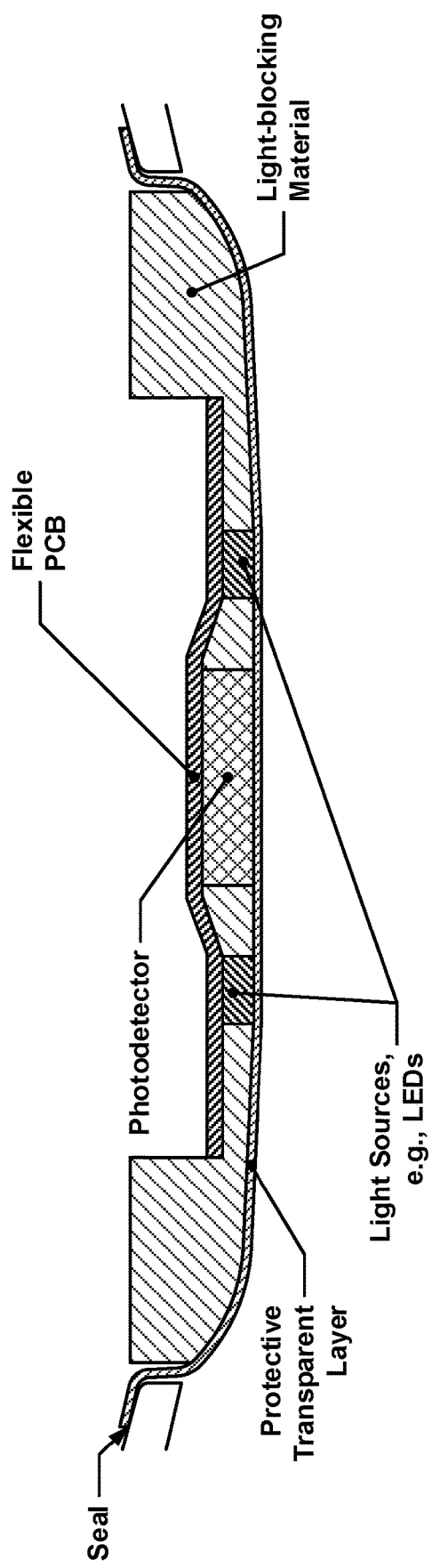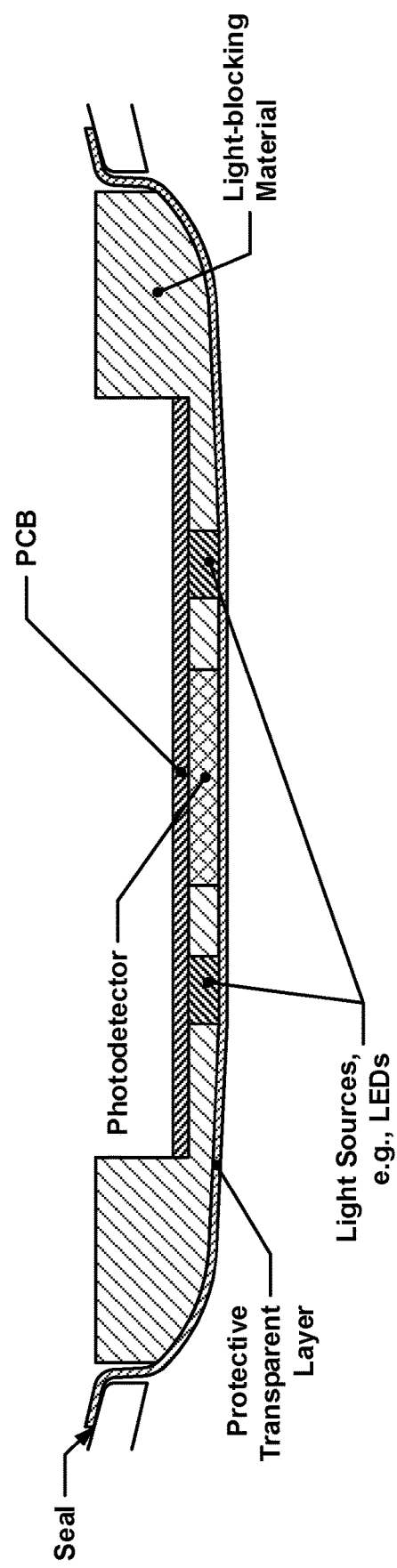
Figure 10A
Figure 10B ic monitoring devices have the ability to perform PWA while accounting for the user's activities, conditions, or status, thereby providing robust and/or customized measurements of arterial stiffness.

PHOTOPLETHYSMOGRAPHY-BASED PULSE WAVE ANALYSIS USING A WEARABLE DEVICE

PRIORITY CLAIM

The present application is a continuation of U.S. application Ser. No. 17/196,983 having a filing date of Mar. 9, 2021 (now U.S. Pat. No. 11,684,281, issued on Jun. 27, 2023), which is a continuation of U.S. application Ser. No. 15/406,501 having a filing date of Jan. 13, 2017 (now U.S. Pat. No. 10,973,422, issued on Apr. 13, 2021), which claims the benefit of U.S. Provisional Application No. 62/286,224 having a filing date of Jan. 22, 2016. Applicant claims priority to and the benefit of each application listed above and incorporates each such application herein by reference in its entirety.

BACKGROUND

This disclosure provides devices and methods for estimating arterial stiffness using pulse wave analysis, particularly with photoplethysmography.

Arteries harden as a result of vascular ageing and other physiological factors such as pathologies and diets. Arterial stiffness indicates cardiovascular dysfunction and is an established independent predictor of cardiovascular risk.

The contraction of the left ventricle pumps blood into the aortic artery, causing blood volume and blood pressure to change in the arteries, forming an arterial pressure wave or pulse wave in the peripheral arteries. Arterial stiffness can be non-invasively estimated by pulse wave analysis (PWA) of blood pressure data obtained by a tonometer, or blood volume data of a photoplethysmogram (PPG) sensor. PWA involves obtaining pulse waveforms from pulse wave data, and extracting and analyzing morphological features of the pulse waveforms. Morphological features of the pulse waveforms, such as augmentation index, reflection index, pulse transit time, are shown to correlate with arterial stiffness.

PWA is conventionally performed at a doctor's office by a medical professional (e.g., tonometer-based PWA), or through a take-home device administered to user for a few days. The administration of the analysis may require stringent procedures or measuring conditions. Conventional hardware such as a tonometer or a finger-based PPG for performing PWA can be cumbersome to use. As a result, PWA data collection and results may be compromised by various extraneous factors in a nonclinical setting. It may be impractical or inconvenient to obtain repeated measurements through a sufficiently long period of time. Therefore, there are needs for devices and methods that allow convenient, noninvasive, and accurate measuring of arterial stiffness.

SUMMARY

Devices and methods are provided for non-invasively measuring arterial stiffness using PWA of PPG data. In some implementations, wearable biometric monitoring devices for measuring arterial stiffness have the ability to automatically and intelligently obtain PPG data under suitable conditions while the user is engaged in activities or exercises, providing good-quality PPG data for PWA while conserving power of the wearable biometric monitoring devices. In some implementations, wearable biometric monitoring devices can remove PPG data variance caused by factors unrelated to arterial stiffness. In some implementations, wearable biometric monitoring devices have the ability to perform PWA while accounting for the user's activities, conditions, or status, thereby providing robust and/or customized measurements of arterial stiffness.

One aspect of the disclosure provides a biometric monitoring device for measuring arterial stiffness. The device include: (a) a wearable fixing structure configured to attach to a user and/or a user's apparel in a manner allowing the user to wear the biometric monitoring device while performing activities; (b) an inertial sensor configured to generate inertial data measuring movement experienced by the biometric monitoring device; (c) a photoplethysmogram ("PPG") sensor to generate PPG sensor data; and (d) one or more processors. The processors are configured to: (i) obtain the inertial data from the inertial sensor, (ii) obtain the PPG sensor data from the PPG sensor, (iii) filter the PPG sensor data using information obtained from the inertial data, and (iv) determine one or more morphological features of a pulse waveform derived from the filtered PPG sensor data, and/or transmit the filtered PPG sensor data to a device configured to determine the one or more morphological features of the pulse waveform from the filtered PPG sensor data, wherein the one or more morphological features are related to arterial stiffness.

In some implementations, the one or more processors are further configured to, before (ii): determine that one or more conditions for collecting pulse waveform data from the user are satisfied; and trigger, based on the determination that the one or more conditions are satisfied, the PPG sensor to obtain the PPG sensor data.

In some implementations, the one or more conditions include the user's activity or location. In some implementations, the one or more processors are configured to determine that the inertial data matches an activity profile. In some implementations, the activity profile is for an activity such as resistance training, aerobic exercising, endurance training, sitting, working, and sleeping. In some implementations, the one or more conditions include the inertial data being indicative of the biometric monitoring device being still for a period of time. In some implementations, triggering the PPG sensor to obtain the PPG sensor data includes increasing a sampling rate in which the PPG sensor operates.

In some implementations, the inertial sensor includes an accelerometer.

In some implementations, the one or more processors are further configured to determine that the inertial data matches an orientation profile.

In some implementations, (ii) is performed based on the one or more processor determining, from the inertial data, that the biometric monitoring device has experienced movement below a movement threshold for a period of time and/or the inertial data matches an orientation profile.

In some implementations, the wearable fixing structure includes a strap for attaching to the user's limb. In some implementations, the wearable fixing structure includes a strap for attaching to the user's wrist. In some implementations, the strap and/or the one or more sensors are configured to permit the PPG sensor to obtain the PPG sensor data from the user's ulnar and/or radial artery.

In some implementations, the biometric monitoring device further includes one or more sensors selected from the group consisting of a temperature sensor, a strain sensor, and a pressure sensor. In some implementations, the one or more processors are further configured to perform wave normalization on the pulse waveform using temperature data from the temperature sensor. In some implementations, the one or more processors are further configured to perform wave normalization on the arterial waveform using pressure data from the strain sensor or the pressure sensor.

In some implementations, the one or more processors are further configured to use the inertial data to reject motion artifact.

In some implementations, the biometric monitoring device further includes an enclosure enclosing the inertial sensor, the PPG sensor, and the one or more processors.

In some implementations, the one or more processors are further configured to trigger repeatedly obtaining the PPG sensor data for determining pulse waveforms, while the user wears the biometric monitoring device.

In some implementations, the one or more processors are configured to trigger obtaining the PPG sensor data for at least X pulse waveforms over a period of at most about Y seconds. In some implementations, the one or more processors are configured to trigger obtaining the PPG sensor data for at least X pulse waveforms every day over a period of at least Y days.

In some implementations, the one or more processors are further configured to determine the user's heart rate using the PPG sensor data and trigger obtaining the PPG sensor data for a number of pulse waveforms, wherein the number of pulse waveforms depends at least partly on the user's heart rate. In some implementations, the number of pulse waveforms increases as the user's heart rate increases.

In some implementations, the one or more processors are further configured to determine the user's respiration rate and trigger obtaining the PPG sensor data for a number of pulse waveforms, wherein the number of pulse waveforms depends at least partly on the user's respiration rate. In some implementations, the number of pulse waveforms increases as the user's respiration rate increases.

In some implementations, the one or more processors are configured to trigger obtaining the PPG sensor data at a schedule based on activity types or locations of the user.

In some implementations, the one or more processors are further configured to analyze the pulse waveform to obtain an estimate of the user's arterial stiffness.

Another aspect of the disclosure provides a method for measuring arterial stiffness of a user. The method employs a biometric monitoring device including one or more processors, a photoplethysmogram (PPG) sensor, and one or more additional biometric sensors. The method involves: (a) determining that one or more conditions for collecting pulse waveform data from the user are satisfied; (b) triggering, based on the determination of (a), the PPG sensor to collect pulse waveform data from the user; and (c) obtaining one or more measurements indicating arterial stiffness from the collected pulse waveform data of the user.

In some implementations, determining that the one or more conditions for collecting pulse waveform data from the user are satisfied includes: obtaining biometric data regarding the user from the one or more additional biometric sensors; and analyzing the biometric data to determine that the one or more conditions for collecting the pulse waveform data from the user are satisfied. In some implementations, the one or more conditions include one or more of the following: a motion level of the user being below a motion threshold, an activity of the user being a specific activity type, a body temperature of the user meeting a criterion, noise in previously obtained pulse waveform data being above a noise threshold, a force indicative of a tightness between the biometric monitoring device and the user meeting a criterion, historical activity data meeting a past activity criterion, a placement of the PPG sensor is determined to be appropriate, an orientation of the device meeting a criterion, and a posture of the user meeting a criterion. In some implementations, the placement of the sensor is determined to be appropriate when the biometric data indicates that the PPG sensor is placed on the user's body near an artery.

In some implementations, the method further includes recording historical activity data of the user. In some implementations, the historical activity data include the amount, time and type of the last activity and the time between the last activity and the time when the pulse waveform data is collected.

In some implementations, the one or more measurements indicating arterial stiffness are selected from the group consisting of: augmentation index, reflection index, stiffness index, acceleration plethysmogram features, and any combinations thereof.

In some implementations, the one or more measurements indicating arterial stiffness are obtained from cross-correlation of pulse waveforms with preexisting templates or decomposition of the pulse waveforms using one or more approximation methods. In some implementations, the one or more approximation methods include curve fitting.

In some implementations, triggering the PPG sensor includes operating the PPG sensor at a sampling rate equal to or higher than about 150 Hz. In some implementations, triggering the PPG sensor includes increasing a sampling rate of the PPG sensor.

In some implementations, the one or more conditions for collecting pulse waveform data includes a motion level of the user being below a motion threshold.

In some implementations, triggering the PPG sensor includes increasing an intensity of light emitted by an LED of the PPG sensor.

In some implementations, triggering the PPG sensor includes sampling from LEDs that are spaced further apart than LEDs used for heart rate or pulse oxygenation.

In some implementations, triggering the PPG sensor includes operating the PPG sensor at a sampling rate equal to or higher than about 150 Hz in two or more intervals distributed in two or more different hours in a period of time.

In some implementations, the biometric monitoring device is configured as a wrist-worn biometric monitoring device. In some implementations, the biometric monitoring device includes one or more PPG sensors disposed on a band configured to be worn around a wrist. In some implementations, the biometric monitoring device includes a plurality of PPG sensors disposed on a band configured to be worn around a wrist. In some implementations, the biometric monitoring device includes a display and one or more PPG sensors, wherein the display and at least one of the PPG sensors are configured to be positioned on substantially opposite sides of a wrist when worn on the wrist.

In some implementations, the one or more additional biometric sensors are selected from the group consisting of: an accelerometer, a gyroscope, an altimeter, a temperature sensor, a force sensor, a pressure sensor, a galvanic skin response sensor, a magnetometer, a GPS sensor, an ambient light sensor, and any combinations thereof.

An additional aspect of the disclosure relates to a method implemented at a biometric monitoring device including one or more processors, a photoplethysmogram (PPG) sensor, and one or more additional biometric sensors, for measuring arterial stiffness of a user. The method includes: operating the PPG sensor to obtain pulse waveform data from the user; operating the one or more additional biometric sensors to obtain biometric data other than PPG data; extracting a plurality of pulse waveforms from the pulse waveform data; normalizing the plurality of pulse waveforms; aggregating the plurality of pulse waveforms; and obtaining one or more measurements indicating arterial stiffness from the aggregate pulse waveform data.

In some implementations, normalizing the pulse waveform data includes scaling the plurality of pulse waveforms to a duration in time or a pulse waveform cycle and an amplitude.

In some implementations, normalizing the pulse waveform data includes adjusting the pulse waveform data for one or more factors determined from the other biometric data. In some implementations, normalizing the pulse waveform data includes: modeling a relationship between (a) one of the one or more factors, and (b) a variable related to the amplitude of the pulse waveform; applying the one factor of the user to the modeled relationship to obtain a normal pulse waveform or features thereof; and scaling the plurality of pulse waveforms or features thereof based on the normal pulse waveform or features thereof. In some implementations, the variable related to the amplitude of the pulse waveform is selected from the group consisting of: blood volume, arterial compliance, blood flow, or blood perfusion.

In some implementations, obtaining one or more measurements indicating arterial stiffness includes applying the one or more factors, as well as the aggregate pulse waveform data, to a model to obtain the one or more measurements.

In some implementations, obtaining one or more measurements indicating arterial stiffness including: (a) selecting a model based on the one or more factors, and (b) applying the aggregate pulse waveform data to the selected model to obtain the one or more measurements indicating arterial stiffness.

In some implementations, the one or more factors are selected from the group consisting of user activity, user posture, device orientation, user body temperature, and sensor pressure.

In some implementations, the method further includes filtering out a motion signal component from the pulse waveform data.

In some implementations, the method further includes removing data of at least one outlier pulse waveform from the normalized pulse waveform data before aggregating the plurality of pulse waveforms.

In some implementations, removing data of at least one outlier pulse waveform includes: obtaining one or more pulse waveform templates, each template being derived from one or more pulse waveforms obtained from the user; identifying the at least one outlier pulse waveform by comparing the user's pulse waveforms to the one or more pulse waveform templates; and removing data of the at least one outlier pulse wave.

In some implementations, a pulse waveform template is obtained from the user when the user is in a condition selected from the group consisting of: sleeping, orienting a wrist wearing the biometric monitoring device in a defined direction, performing an exercise, having recently performed an exercise, having no recent exercises or steps, having no erratic motions, physiological stress, elevated heart rate or low heart rate variability, having not consumed food or drugs recently and any combinations thereof.

In some implementations, removing data of at least one outlier pulse waveform includes determining cross-correlation scores among the plurality of pulse waveforms and removing data of at least one pulse waveform having cross-correlation scores lower than a criterion value. In some implementations, the criterion value is a score at a relative threshold generated from the cross-correlation scores.

In some implementations, the method further includes, prior to obtaining the one or more measurements indicating arterial stiffness, averaging data across multiple pulse waveforms.

In some implementations, the method further includes presenting the one or more measurements indicating arterial stiffness on the biometric monitoring device.

A further aspect of the disclosure relates to another method implemented at a biometric monitoring device including one or more processors, a photoplethysmogram (PPG) sensor, and one or more additional biometric sensors, for evaluating arterial stiffness of a user. The method includes: operating the PPG sensor to obtain pulse waveform data from the user; operating the one or more additional biometric sensors to obtain other biometric data; obtaining one or more measurements of one or more pulse waveform morphological features using the pulse waveform data; obtaining one or more measurements of one or more additional variables derived from the other biometric data; and estimating the arterial stiffness of the user using the one or more measurements of the pulse waveform morphological features and the one or more measurements of the additional variables.

In some implementations, the additional variables are selected from the group consisting of: weight measurement, temperature, respiration measurements, blood pressure measurements, sleep stage, user height, user posture, orientation of the biometric monitoring device, an activity pattern recently detected, and variables derived therefrom.

In some implementations, estimating the arterial stiffness of the user includes applying the one or more measurements of the pulse waveform morphological features to a model, wherein the model relates the pulse waveform morphological features to an arterial stiffness measurement.

In some implementations, the method further includes presenting information indicating the estimated arterial stiffness on the biometric monitoring device.

An additional aspect of the disclosure relates to an additional method implemented at a biometric monitoring device including one or more processors and a photoplethysmogram (PPG) sensor. The method includes: operating the PPG sensor to obtain pulse waveform data from the user; obtaining one or more measurements of pulse waveform morphological features of the user using the pulse waveform data; providing a template of the pulse waveform morphological features; comparing the one or more measurements of pulse waveform morphological features of the user and the pulse waveform morphological features of the template; and determining an arterial stiffness measurement of the user based on one or more comparison results from comparing the pulse waveform morphological features of the user and the template.

In some implementations, the template includes statistics that quantify the pulse waveform morphological features of a plurality of users. In some implementations, the plurality of users and the user belong to the same group determined by clustering. In some implementations, the clustering is based on a weight measurement and/or age of the plurality of users.

In some implementations, determining an arterial stiffness measurement of the user includes applying the comparison results to a model to obtain the arterial stiffness measurement of the user, wherein the model takes the comparison results as inputs and provides a value of an arterial stiffness measurement as an output. In some implementations, the model includes a general linear model, a non-linear model, a regression tree model, or a neural network model.

In some implementations, the template includes pulse waveform morphological features of a plurality of pulse waveforms collected from the user.

In some implementations, providing the template includes building the template using features of a plurality of pulse waveforms obtained from the user.

In some implementations, the method further includes displaying the arterial stiffness measurement of the user on the on the biometric monitoring device.

These and other objects and features of the present disclosure will become more fully apparent from the following description, with reference to the associated drawings and appended claims.

BRIEF DESCRIPTION OF THE DRAWINGS

FIG. 10A provides a cross sectional view of a sensor protrusion of an example portable monitoring device.

FIG. 10B depicts a cross sectional view of a sensor protrusion of an example portable monitoring device; this protrusion is similar to that presented in FIG. 10A with the exception that the light sources and photodetector are placed on a flat and/or rigid PCB.

DETAILED DESCRIPTION

Figure 1:
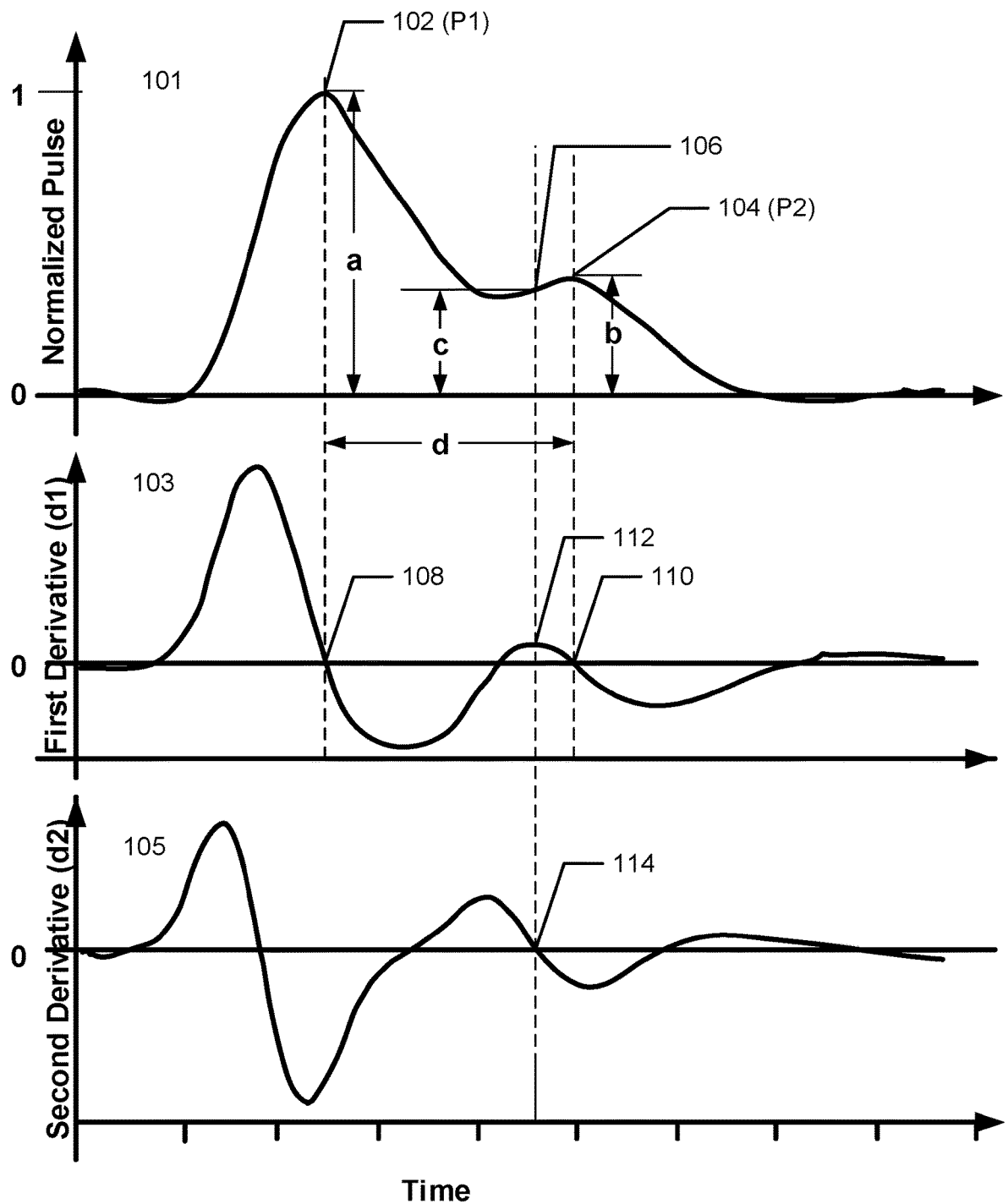
FIG. 1 shows a representation of a pulse waveform that can be obtained from PPG data and the first and second derivatives of the pulse waveform.

Various morphological features of the pulse waveforms are correlated with arterial structures and functions including arterial stiffness. Morphological features of a pulse waveform as used herein include various aspects of the shape of the waveform and information derived therefrom including the slopes of various portions of the waveform, time separation between such portions, amplitudes of such portions, and the like. Morphological features of the pulse waveform also include various aspects of the shape of the derivatives of the waveform including a first derivative, a second derivative, and higher order derivatives. Unless otherwise qualified, any one or more of these features may be used in the analyses described herein.

In some context not specific to the disclosure herein, the term pulse waveform can be interpreted as closely related to the shape of a PPG graph reflecting blood volume change caused by pulsed blood flow, while the term pulse wave may be interpreted as more closely related to the blood volume change caused by pulsed blood flow. However, the two terms are used interchangeably herein unless specified as different. For instance, pulse waveform analysis and pulse wave analysis are used interchangeably herein.

Introduction

PWA involves obtaining and analyzing morphological features of pulse waveforms, which may be obtained from, e.g., PPG data. Morphological features of pulse waveform (or arterial pressure waveform) can provide useful information relating to arterial structure and function, including arterial stiffness. Arterial stiffness is an important indicator of cardiovascular diseases and a useful predictor of cardiovascular risks. Various implementations of this disclosure provide one or more improvements below that are lacking in existing technology for measuring and monitoring arterial stiffness.

Various morphological features of the pulse waveforms are correlated with arterial structures and functions including arterial stiffness. Morphological features of a pulse waveform as used herein include various features of the shape of the waveform and information derived therefrom. Morphological features of the pulse waveform also include various features of the shape of the derivatives of the waveform.

PWA can be performed at a doctor's office by a professional or at home using a take-home device administered to user for a few days when the user is preferably disengaged from other activities. However, performing PWA at a doctor's office presents a number of difficulties and constraints, such as restrictions on when, where, and how often PWA can be performed. In comparison, some embodiments discussed herein provide devices and methods for estimating arterial stiffness using PPG-based PWA that are non-invasive, easy to operate, and suitable for taking measurements over a number of contexts, such as when a user is engaged in activities in nonclinical settings, e.g., exercising or sleeping.

Further, some embodiments can provide wearable biometric monitoring devices that are small, light, portable, and/or non-intrusive, and can be worn during daily activities and exercise. In some embodiments, the wearable biometric monitoring device can be configured as a wrist-worn device, and equipped with a rechargeable or non-rechargeable battery capable of powering the device to operate for hours, days, weeks, or months per charge. Such configuration and function of the biometric monitoring device allows repeated PPG data collection and PWA over a long time and during many different activities and conditions. Examples of such biometric monitoring devices are presented in FIGS. 7, 8, 9, and 13. In some applications, long-term trending and personalized models can be created to provide features related to a user's physiology.

In some implementations, the wearable biometric monitoring device integrates multiple biometric sensors including a PPG sensor, which sensors are enclosed in a housing of a wearable device. Using biometric data obtained from one or more biometric sensors other than the PPG sensor, the device can provide robust arterial stiffness measurements using PPG-based pulse waveform data under different conditions by canceling noise and controlling factors irrelevant to arterial stiffness measurements. The robustness of the arterial stiffness measurements of the device allows the device to be used in nonclinical settings when the user is engaged in daily activities or exercises, without requiring the administration by a professional.

The robustness and the convenience of the wearable biometric monitoring devices are conducive to measuring arterial stiffness by different types of users (e.g., a user type may be determined by age and/or weight measurement such as weight, body-mass-index (BMI), body fat percentage, and the like) or under different conditions (e.g., skin temperature of the user, pressure between the PPG sensor and the user's skin contact area, currently engaged activity, and recently completed activity). To improve the usefulness of the arterial stiffness information to the different types of users under different conditions, some implementations of the biometric monitoring device can perform PWA that are normalized or tailored for a specific user type or condition. In some implementations, different user types have different values or ranges of values of PWA measurements associated with a condition of interest. For instance, a 5% increase of the augmentation index of a pulse waveform for a first type of user may have a more severe impact than for a second type of user. In some implementations, the biometric monitoring device will alarm the first type of user for such an increase, but will not alarm the second type of user. In another example, if a user belongs to a first group, the user's pulse waveform can be normalized relative to the first group. Then the morphological features of the normalized pulse waveforms are compared to a template of the first group. Group-specific measurements of arterial stiffness can be obtained from the comparison. In another example, algorithms for determining arterial stiffness may differ depending on the group to which the user belongs. For example, the transfer function mapping pulse morphological features to arterial stiffness may be different for a group consisting of users above 60 years old as compared to the group of users younger than 60 years old.

Some embodiments of the biometric monitoring device discussed herein can perform PWA that are normalized or customized for a specific user condition. For instance, in some implementations, the wearable biometric monitoring device includes one or more of accelerometers or inertial sensors, skin temperature sensors, and force sensors. Using the accelerometer signal or inertial data, frequency components or periodic components in PPG signal corresponding to those in accelerometer signal or inertial data can be filtered out from the PPG signal before measuring arterial stiffness. Moreover, skin temperature can affect perfusion of peripheral arteries and measurement of skin temperature allows for appropriate normalization of pulse waveform data before determining morphological features of pulse waveforms or arterial stiffness measurements. Furthermore, a force sensor can give an indication of band tightness which allows for non-linearly normalizing features based on the changing compliance of the arteries due to the variable sensor contact force.

Such flexible capabilities allow the biometric monitoring device to provide individualized and customized measurements of arterial stiffness that are indicative of an individual user's health when the user is under a specific condition or of a specific user type.

In a wearable biometric monitoring device with a form factor that is easy and comfortable to use, the battery powering the biometric monitoring device has limited bulk (mass and volume) and limited capacity. In some implementations, the wearable biometric monitoring device can determine one or more conditions when the PPG sensor should be triggered to collect PPG data and perform pulse waveform analysis. For example, in some implementations, the wearable biometric monitoring device includes an inertial sensor and it triggers its PPG sensor to obtain data for pulse waveform analysis if it detects that the user is relatively still or engaged in a specific activity (e.g., sleeping or sitting). The device can determine the user's activity using the inertial data. For instance, it detects or infers that the user is relatively still when inertial data is indicative of the biometric monitoring device have been still for a period of time. When the one or more conditions are not met, in some implementations, the device discontinues the PPG sensor's collection of data for pulse waveform analysis to conserve energy. In some implementations, the inertial sensor includes one or more accelerometers.

For higher fidelity of the pulse waveform, PPG signal can be sampled at a high rate (>25 Hz e.g. 100 Hz) and/or oversampled at an even higher rate and then averaged to reduce the noise of a waveform at a given sampling rate (e.g. 100 Hz). This can provide better representation of the wave's morphological details by reducing noise and increasing time resolution. The improved representation enables the detection of subtle changes to a user's pulse morphology and the detection of subtle morphological features, such as the dicrotic notch in a pulse waveform. In some implementations, when the device determines a condition for collecting PPG data is not met, the sampling rate or light intensity of a light source of the PPG sensor can be reduced to perform other functions such as heart rate measurement or skin proximity detection. By operating the PPG sensor in different modes under different conditions, the wearable biometric monitoring device can achieve utilities while preserving battery power.

Pulse Wave Analysis and Arterial Stiffness Measurements

Various implementations of the disclosure provide devices and methods for performing pulse wave analysis (PWA) on PPG data to obtain morphological features of pulse waveforms and obtain measurements and estimates of arterial stiffness using the obtained morphological features.

FIG. 1 shows, in the top panel, a representation of a pulse waveform that can be obtained from PPG data. The horizontal axis represents time, and the vertical axis represents normalized pulse pressure or signal related to pulse pressure. For instance, voltage of a sensor may be mapped to blood volume, which can then be mapped to blood pressure. Various morphological features of the pulse waveforms are correlated with arterial structures and functions including arterial stiffness. Note that the waveform shown in FIG. 1 is a normalized waveform in the Y axis. All of the techniques described herein may also be used on a non Y-normalized pulse waveform. All of the techniques described here may also be used on an X-normalized (or time-normalized) pulse waveform where the length of each pulse is scaled to 1 or some normal value. There are various ways to normalize signal. Any single normalization technique or any combination of normalization techniques may be employed to derive features for an arterial stiffness measurement. Some of the morphological features of the pulse waveform that may be obtained in various implementations of the disclosure are described next.

The pulse waveform 101 shown in the top panel, as an example, has two distinct peaks 102 and 102, with P1 (102) on the left being higher than P2 (104) on the right. P1 (102) is caused by the ejection of blood from the left ventricle, corresponding to early systolic pressure. P2 (104) is caused by a reflection wave, corresponding to late systolic pressure. It has been shown that ageing may cause arterial walls to harden, which can give rise to a more pronounced reflection wave.

Pulse waveforms observed at the peripheral arteries have different shapes and morphological features than those observed at or near the aortic artery. For instance, in some samples under some conditions, a waveform observed at a peripheral artery is more likely to have two distinct peaks, where a waveform observed near the aortic artery are more likely to have two peaks merged into a left shoulder and a right shoulder, with the right shoulder sometimes being higher than the left shoulder in some cases. The example shown here is more representative of a pulse waveform observed at a peripheral artery, such as at the wrist.

The base of the waveform near zero corresponds to diastolic pressure. The height of the early systolic pressure (P1) relative to the diastolic pressure is labeled as "a" in the figure, which is also known as the pulse pressure. The height of the late systolic pressure (P2) relative to the diastolic pressure is labeled as "b" in the figure, which is also known as the augmentation pressure. The ratio b/a is known as the augmentation index, or peripheral augmentation index for a peripheral pulse wave. Augmentation index correlates positively with arterial stiffness. Augmentation index is a sensitive marker of arterial status and a predictor of adverse cardiovascular events in a variety of patient populations. It has been shown that higher augmentation index is associated with target organ damage. As shown in some studies, augmentation index can distinguish between the effects of different vasoactive medications while upper arm blood pressure and pulse wave velocity do not.

The time difference between P1 and P2, labeled as "d," indicates the time difference between the peak of the ejection wave and the peak of the reflection wave. It is known as reflection transit time, which can correspond to pulse transit time in some measurements. Pulse transit time and pulse wave velocity have been shown to correlate with blood pressure and arterial stiffness.

An inflection point at the upstroke of the second peak provides a morphological feature with a pressure of "c", which may be used to obtain a reflection index in some cases of PWA. As with augmentation index, reflection index has a positive correlation with arterial stiffness. Similarly to the time measurement from P1 (102) to P2 (104) being equal to "d", a time between P1 and inflection point 106 or P2 and inflection point 106 can be used in an algorithm to determine arterial stiffness.

The middle panel of FIG. 1 shows the first derivative of the pulse waveform 103 in the top panel. The bottom panel of FIG. 1 shows the second derivative 105. It is illustrated here that morphological features of the derivatives of a pulse waveform may be used to identify relevant morphological features in the pulse waveform. For instance, the positive-to-negative zero crossing points 108 and 110 of the first derivative corresponds to the local maxima P1 and P2 (102 and 104) in the pulse waveform. The second positive-to-negative zero crossing point 114 of the second derivative corresponds to the local maxima of the first derivative 112 and the inflection point of the pulse waveform 106.

The above mentioned morphological features are relevant for arterial stiffness measurements. Examples of other useful morphological features include but are not limited to: ejection duration, heart rate, pressure at first shoulder, pressure at second shoulder, pressure at end systole, augmented pressure, mean diastolic pressure, mean arterial pressure, mean systolic pressure, tension time index, diastolic time index, subendocardial variability ratio, maximum rate of rise, reference age, acceleration features (e.g., those determined from the derivatives), and stiffness index. It is to be appreciated that some implementations may measure one or more of the pressure measurements just listed via voltage or volume signals generated by a PPG sensor (or PPG sensors), instead of pressure signals obtained from a pressure sensor. The voltage or volume signals obtained via a PPG sensor may be normalized. To illustrate, voltage values generated by a PPG sensor may be mapped to volume values, which, in turn, may be non-linearly mapped to pressure values. As such, the morphological features of pressure described above may be indicated by voltage or volume signals generated by a PPG sensor.

Figure 2:
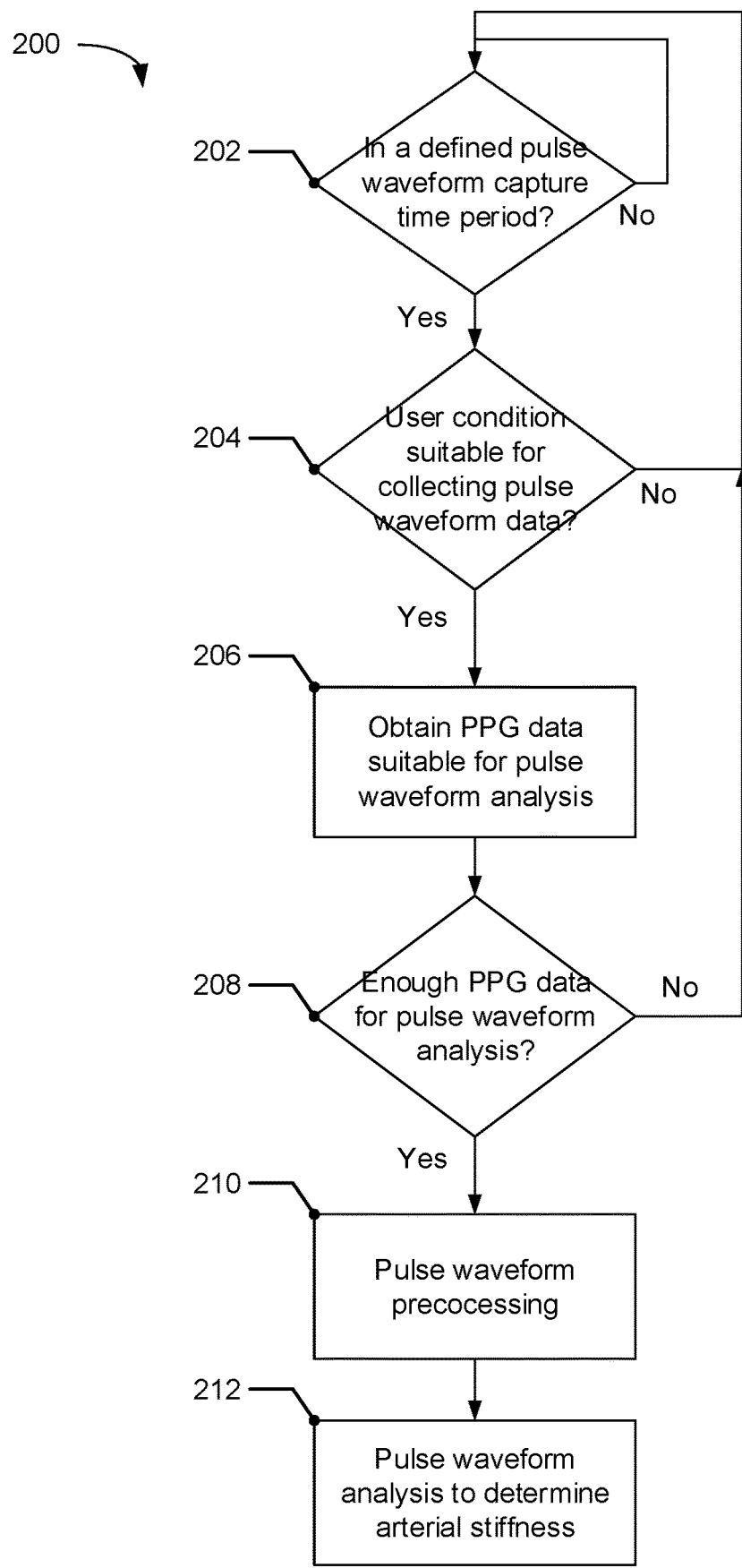
FIG. 2 shows a flow chart illustrating a process 200 for determining arterial stiffness implemented by a wearable biometric monitoring device in some implementations.

One aspect of the disclosure provides a wearable biometric monitoring device that is capable of intelligently determining one or more conditions and obtaining PPG data suitable for PWA if the one or more conditions are satisfied. The obtained PPG data may be preprocessed to obtain pulse waveforms in, e.g., a standard or normalized format, which are then used to perform PWA to determine arterial stiffness. FIG. 2 shows a flow chart illustrating a process 200 for determining arterial stiffness implemented by a wearable biometric monitoring device in some implementations. The process 200 starts by determining whether the current time is in a defined pulse waveform capture time period. For instance, the defined data capturing may be a specific time of day, a specific day of the week, a specific time from a defined time, or a specific time since the last data capture session, etc. This allows the biometric monitoring device to obtain PPG data based on a schedule or time considerations. The schedule may be based on the user's history (e.g., typical times of day or the week when the user is not engaged in strenuous activity), a processor's available bandwidth for performing PWA, and the like. If the current time is not within a defined capture time period, the device does not trigger PPG data collection and wait for the next time interval to examine the condition again. See decision block 202.

However, if it is determined that the current time is in a defined time period for obtaining PPG data for PWA, the process further determine whether one or more user conditions suitable for collecting PPG data to obtain pulse waveforms are satisfied. See decision block 204. If the one or more conditions are not satisfied, the process loops back to checking whether the next instance of time is in the defined pulse waveform capturing time period. If the one or more conditions are satisfied, the process proceeds to trigger the PPG sensor to obtain PPG data in a manner that is suitable for generating pulse waveform data for PWA. See block 206.

Although decision block 202 and decision block 204 are shown sequentially, they may be processed in reversed order, in alternative, or in conjunction. Indeed, unless specified otherwise, the sequence of many blocks in the flow charts herein is generally illustrative and can be reordered.

In some implementations, triggering the PPG sensor to collect pulse waveform data requires activating a light source of the PPG sensor to emit light pulses in a particular frequency and intensity. Because PWA requires extracting morphological features from pulse waveforms, it is desirable to have high sampling rate and sufficient signal strength. In various implementations, the sampling rate is at least about 25 Hz, 50 Hz, 100 Hz, 150 Hz, 200 Hz, or 400 Hz. In some implementations, the PPG sensor operates at a lower sampling frequency (e.g., less than about 25 Hz) before entering pulse waveform data collection, and increases sampling rate when triggered to collect pulse waveform data. In some implementations, triggering the PPG sensor includes sampling from one or more LEDs that are spaced further apart than the LEDs which are used for other purposes (e.g. heart rate measurement). Using LEDs that are spaced further apart may improve the PPG signal for pulse waveform analysis and/or cause the PPG sensor to sample a volume of tissue that is deeper than closely spaced LEDs. Additionally, in some implementations, triggering the PPG sensor includes using an LED with different wavelength, e.g. red or infrared, compared to the LED used to acquire heart rate data.

In some implementations, the one or more conditions for triggering the PPG sensor include motion of the user. If the user's motion level is below a criterion value (e.g., a motion threshold), the biometric monitoring device can use motion data from a motion/inertia sensor to determine that the user is in a condition suitable for collecting PPG data for PWA. In other words, if the user is relatively still, the biometric monitoring device will trigger the PPG sensor of the device to collect pulse waveform data. In these implementations, the biometric monitoring device includes one or more of the motion sensors described herein.

In some implementations, the one or more conditions for triggering the PPG sensor include activity type the user is engaged in. For instance, in some implementation, the biometric monitoring device triggers PPG data collection after determining that the user is sleeping, exercising, or working. In these implementations, the biometric monitoring device can use one or more of the biometric sensors described herein after to determine that the user is sleeping. For instance, the biometric monitoring device may use motion data, pulse waveform data, respiration rate data, etc. to determine that the user is sleeping.

In some implementations, the one or more conditions for triggering the PPG sensor include the pressure between the device and the user's body or user's skin contact area. The biometric monitoring device can determine to trigger the PPG sensor when the pressure between the device and the user's body meets a criterion. The biometric monitoring device includes a pressure sensor that can sense the pressure between the user and the device. In various implementations, the pressure sensor may be one or more of the following: a force sensor, force sensitive resistor, mechanical sensor, load sensor, load cell, strain gauge, piezo sensor, membrane potentiometer, or any other suitable pressure sensor. If the pressure is too high or too low for generating useful pulse waveform data, the biometric monitoring device may elect to not trigger the PPG sensor to collect pulse waveform data. In some implementations, the biometric monitoring device may present information to the user indicating that a condition for collecting PPG data for PWA is not met, so that the user may correct the condition of the device to allow PPG data collection.

Other user conditions for triggering the PPG sensor to collect pulse waveform data include but are not limited to: body temperature, body position (e.g., arm orientation), noise in previously obtained pulse waveform data being above a noise threshold, historical activity data meeting a past activity criterion, a placement of the PPG sensor is determined to be appropriate, hydration level, activities currently engaged in, activities recently completed, diet, moisture level, an orientation of the device meeting a criterion, a posture of the user meeting a criterion. In some implementation, the placement of the sensor is determined to be appropriate when the biometric data indicates that the PPG sensor is placed on the user's body near an artery. In some implementations, past activity criteria include but are not limited to, for instance, a lack of vigorous activity in the past X (e.g., 30) minutes, step rate in the last X (e.g., 30) minutes never exceeding a step threshold (e.g. 120 steps per minute), and the last X (e.g., 10) minutes consisting of sedentary activity.

In these implementations, the biometric monitoring device includes one or more biometric sensors described herein after, and is configured to use biometric data obtained from the sensors to determine whether one or more of the conditions are satisfied.

In some implementations, the biometric monitoring device can collect motion data and record historical activity data of the user. In some implementations, the historical activity data include the amount, time and type of the last activity. In some implementations, the biometric monitoring device records the time between the last activity and the time when pulse waveform data is collected.

In some implementations, the device automatically triggers obtaining the PPG sensor data for at least about X (e.g., 3) pulse waveforms over a period of Y (e.g., 60) seconds. In some implementations, the device automatically triggers obtaining the PPG sensor data for at least 1 pulse waveform every day over a period of at least 2 days. In some implementations, the device automatically triggers the PPG sensor to operate at the higher sampling rate (e.g., 25 Hz or faster, 50 Hz or faster, 100 Hz or faster, 150 Hz or faster, or 200 Hz or faster) in two or more intervals distributed in two or more different hours in a period of time (e.g., 24 hours). The PPG sensor operates at the lower sampling rate (e.g., slower than 25 Hz) in at least some intervals of in the period of times.

In some implementations, the biometric monitoring device can determine the user's heart rate using the PPG sensor data and trigger obtaining the PPG sensor data for a number of pulse waveforms, wherein the number of pulse waveforms depends at least partly on the user's heart rate. In some implementations, the number of pulse waveforms increases as the user's heart rate increases.

In some implementations, the biometric monitoring device can determine the user's respiration rate and trigger obtaining the PPG sensor data for a number of pulse waveforms, wherein the number of pulse waveforms depends at least partly on the user's respiration rate. In some implementations, the number of pulse waveforms increases as the user's respiration rate increases.

After the PPG sensor has collected data for one or more waveforms, process XC00 determines whether enough PPG data for PWA has been collected. For instance, some implementations use PPG data that is sufficient for obtaining at least a few high-quality pulse waveforms. For instance, some implementations collect PPG data sufficient to generate at least about 2, 10, 20, 50, or 100 waveforms in a data collection period. See block 208. If not, the process loops back to an earlier decision block, e.g., block 202. If enough PPG data has been collected, the biometric monitoring device preprocesses PPG data for PWA. See block 210. After PPG data has been preprocessed, such as by a process 300 shown in FIG. 3, PWA is performed to obtain one or more morphological features for determining arterial stiffness. See block 212. In some implementations, the biometric monitoring device presents the one or more morphological features to a user. In some implementations, the biometric monitoring device can apply the one or more morphological features to a model to predict or estimate arterial stiffness, such as in a process shown in FIG. 5.

In some implementations, the biometric monitoring device obtains additional variables that are selected from the group consisting of: weight measurement (e.g., BMI), temperature, respiration measurements, blood pressure measurements, sleep stage, user height, orientation of the biometric monitoring device, an activity pattern recently detected, and variables derived therefrom. In some implementations, the biometric monitoring device can apply the one or more of the additional variables to the model to predict or estimate arterial stiffness.

In some implementations, the biometric monitoring device displays information indicating the estimated arterial stiffness on the biometric monitoring device. Such display may be visual and/or auditory.

In some implementations, one or more measurements indicating arterial stiffness are obtained from cross-correlation of pulse waveforms with preexisting templates or decomposition of the pulse waveforms using one or more approximation methods. In some implementations, the one or more approximation methods include curve fitting.

In some implementations, process 200 is implemented by biometric monitoring device having: (a) a wearable fixing structure configured to attach to a user and/or a user's apparel in a manner allowing the user to wear the biometric monitoring device while performing activities; (b) an inertial sensor configured to generate inertial data measuring movement experienced by the biometric monitoring device; (c) a photoplethysmogram ("PPG") sensor to generate PPG sensor data; and (d) one or more processors. The processors are configured to determine one or more morphological features of a pulse waveform from PPG sensor data collected through the PPG sensor, and/or transmit the PPG sensor data to a device configured to determine the one or more morphological features of the pulse waveform from the PPG sensor data, wherein the one or more morphological features are related to arterial stiffness.

In some implementations, the processors are configured to: (i) obtain the inertial data from the inertial sensor, (ii) obtain the PPG sensor data from the PPG sensor, (iii) filter the PPG sensor data using information obtained from the inertial data, and (iv) determine one or more morphological features of a pulse waveform derived from the filtered PPG sensor data, and/or transmit the filtered PPG sensor data to a device configured to determine the one or more morphological features of the pulse waveform from the filtered PPG sensor data. In some implementations, the one or more processors are further configured to, before (ii): determine that one or more conditions for collecting pulse waveform data from the user are satisfied; and trigger, based on the determination that the one or more conditions are satisfied, the PPG sensor to obtain the PPG sensor data.

In some implementations, one or more activities are applied to a model to predict or estimate arterial stiffness. The activities may include one or more activities selected from the group consisting of exercising, working, and sleeping.

In some implementations, the one or more conditions for triggering PPG data collection include the user's activity or location.

In some implementations, the one or more processors are configured to determine the user's activity from the inertial data, which may be implemented by comparing the inertial data to data of an activity profile. In some implementations, the inertial sensor includes an accelerometer. Activity profiles may be created for various activities, such as resistance training, aerobic exercising, endurance training, sitting, working, and sleeping.

In some implementations, the one or more processors are configured to determine a biometric feature, e.g., a step count, of the one or more activities of the user.

In some implementations, the wearable fixing structure includes a strap for attaching to the user's limb or a strap for attaching to the user's wrist. In some implementations, the strap and/or the one or more sensors are configured to permit the PPG sensor to obtain the PPG sensor data from the user's ulnar and/or radial artery. For example, the strap may be configured so that one or more PPG sensors align to the user's ulnar and/or radial artery. In some embodiments, the strap includes multiple PPG sensors, offset from one another around the length of the strap. In this way, a single strap design may be appropriate for many users, with some users having a first PPG aligned with their ulnar and/or radial artery and other users having a second PPG aligned with their ulnar and/or radial artery. For example, see FIG. 13A.

In some implementations, the wearable fixing structure includes a location sensor, a temperature sensor, a strain sensor, and/or a pressure sensor. In some implementations, the one or more processors of the biometric monitoring device are further configured to use the inertial data to reject motion artifact.

In some implementations, the one or more processors of the biometric monitoring device are configured to trigger obtaining the PPG sensor data at a schedule based on activity types or locations of the user.

Figure 3:
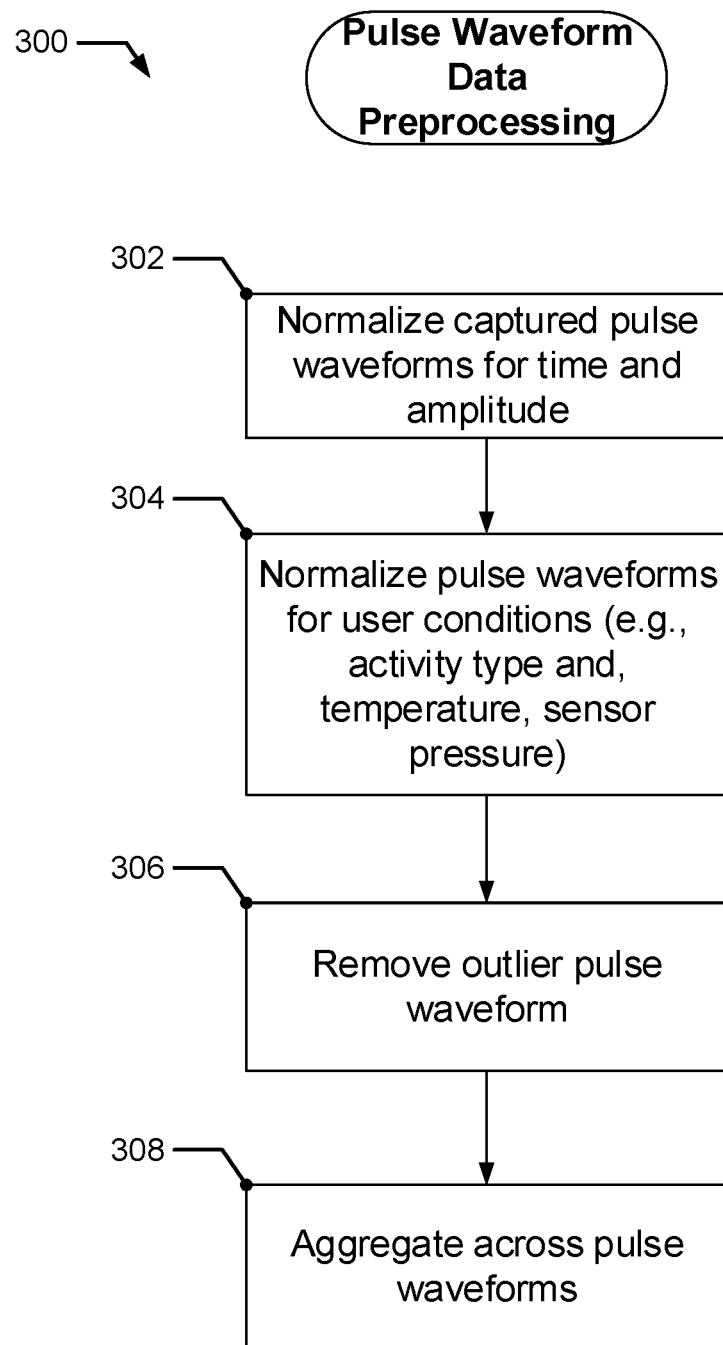
FIG. 3 shows a process flow chart for preprocessing pulse waveform data that can be performed by biometric monitoring device according to some implementations.
Figure 4:
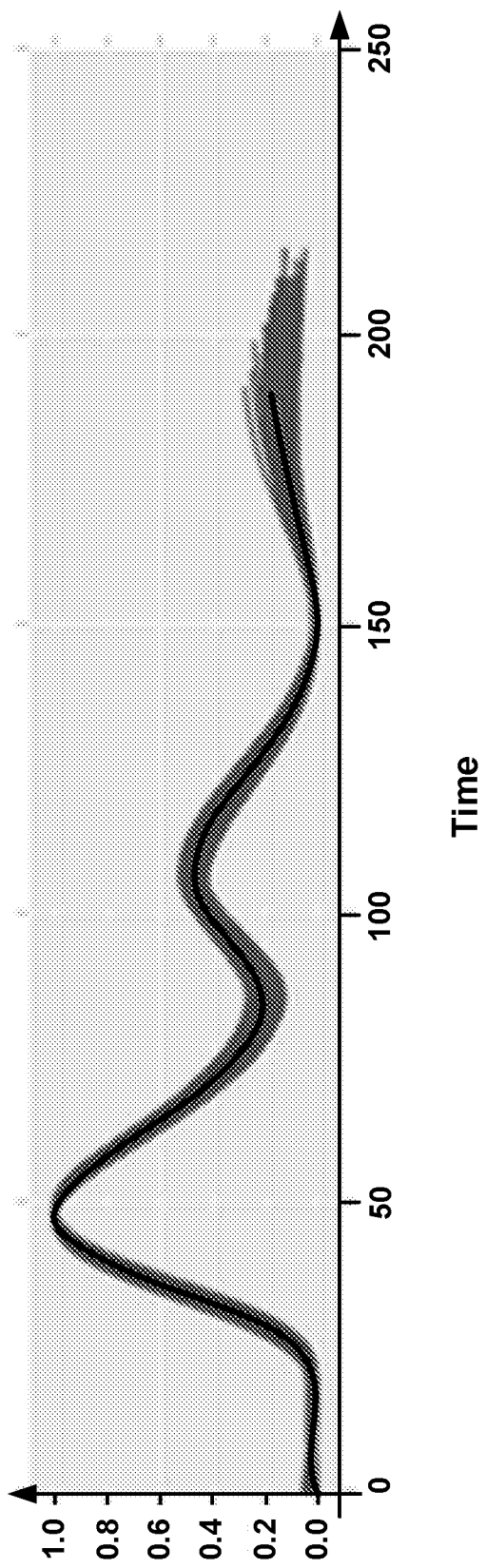
FIG. 4 shows example of multiple y and/or x normalized pulse waveforms (gray) being combined into a more reliable pulse waveform (black).

FIG. 3 shows a process flow chart for preprocessing pulse waveform data that can be performed by biometric monitoring device according to some implementations. Process 300 starts by normalizing pulse waveforms by linearly scaling individual waveforms on a time dimension (x-axis) and on an amplitude dimension (y-axis) so that the minima and maxima on each dimension align across different waveforms. See block 302. After this normalization operation, each waveform has an equal duration and amplitude range. FIG. 4 shows example of multiple y and/or x normalized pulse waveforms (gray) being combined into a more reliable pulse waveform (black).

In some implementations, the relationships can be determined or modeled between the user conditions or related variables and one of a) blood volume, b) arterial compliance, and/or c) blood flow/perfusion. Knowing the relationships (for example, arterial compliance non-linearly decreases with finger skin temp), one can normalize the PWA features or the pulse morphology through a transfer function. The normalized features can then be fed to arterial stiffness models for estimating arterial stiffness.

Process 300 further involves normalizing pulse waveforms for one or more user conditions, such as activity type, temperature, and sensor pressure. See block 304. Other user conditions that may be normalized include but are not limited to: orthostatic state (e.g. sitting, lying down, standing), time of day, day of week, hydrostatic pressure changes, average heart rate. In some implementations, to normalize for a condition variable, the relation between the condition variable and pulse waveform morphology is first established from training waveforms. Then the established relation is applied to scale a test waveform having a specific value of a condition variable. In some implementations, the training waveforms are obtained from the same individual being tested. In other implementations, the training waveforms include waveforms obtained from one or more individuals different from the tested individual. In other implementations, other methods for normalizing for conditions may be employed. For instance, scaling may be non-linear if there is a non-linear relationship between a factor and waveform morphology.

In some implementations, normalizing the pulse waveform data involves: modeling a relationship between (a) one of the one or more factors, and (b) a variable related to the amplitude of the pulse waveform; applying the one factor of the user to the modeled relationship to obtain a normal pulse waveform or features thereof; and scaling the plurality of pulse waveforms or features thereof based on the normal pulse waveform or features thereof. In some implementations, the variable related to the amplitude of the pulse waveform is selected from blood volume, arterial compliance, blood flow, or blood perfusion.

Process 300 further involves removing outlier pulse waveform. In some implementations, pulse waveforms are correlated. Then the waveforms having correlation scores below a relative criterion are considered outliers, which may be removed from downstream PWA. See block 306. In some implementations, pulse waveforms from the same individual being tested are cross correlated. In other implementations, pulse waveforms from more than one individual may be cross correlated to identify outlier waveforms.

After outlier waveforms are removed, data of multiple pulse waveforms can be combined to provide more representative and less noisy pulse waveform data, which can in turn provide more reliable estimates of pulse waveform morphological features and arterial stiffness. See block 308. Note that non-normalized waveforms corresponding to the non-outlier waveforms may be aggregated as well or in place of aggregating the normalized pulse waveforms. In some implementations, some pulse waveform morphological features are obtained from normalized waveforms, and other pulse waveform morphological features are obtained from un-normalized waveforms.

In some implementations, in addition to or instead of normalizing for the user conditions, one or more of the user conditions may be provided as input variables to a model that relates input variables to arterial stiffness, where the model also includes input variables obtained from pulse waveform. As such, the arterial stiffness estimated by the model accounts for different user conditions. For instance, one may use temperature, sensor pressure, posture (e.g., Euler angles), user activity, etc., as parameters or features in the model (e.g., neural network, etc.). Therefore, some implementations obtain one or more measurements indicating arterial stiffness by applying the one or more factors, as well as the pulse waveform data, to a model to obtain the one or more measurements In some implementations, user conditions or related measurements can be used to identify which one of a plurality of trained models should be used to estimate arterial stiffness. For instance, one may apply one model for sitting and another for standing, one for very high skin temperature and one for very low temperature, etc. In such implementations, a decision tree may be used to decide which particular model to use to estimate arterial stiffness. Some implementations obtain one or more measurements indicating arterial stiffness by (a) selecting a model based on the one or more factors, and (b) applying aggregate pulse waveform data to the selected model to obtain the one or more measurements indicating arterial stiffness.

Figure 5:
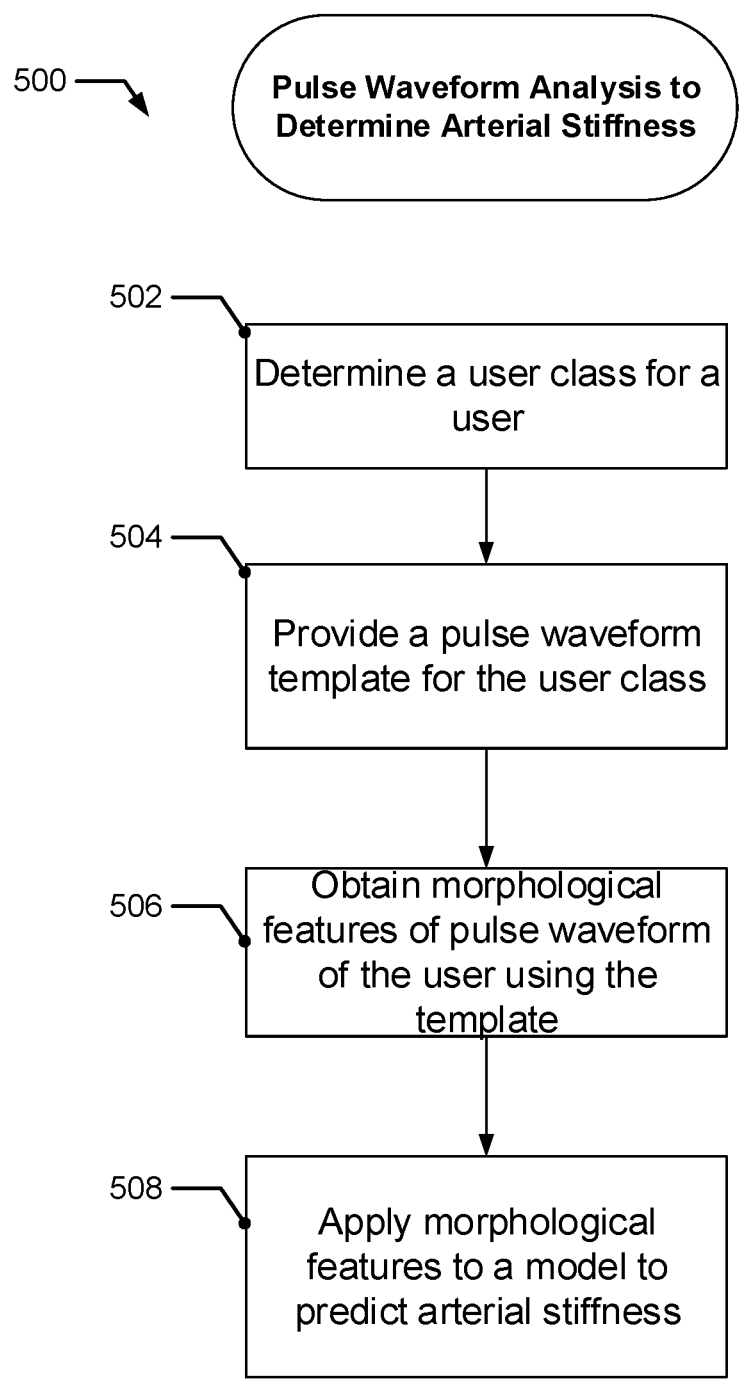
FIG. 5 illustrates a process for performing PWA to determine arterial stiffness.
Figure 6:
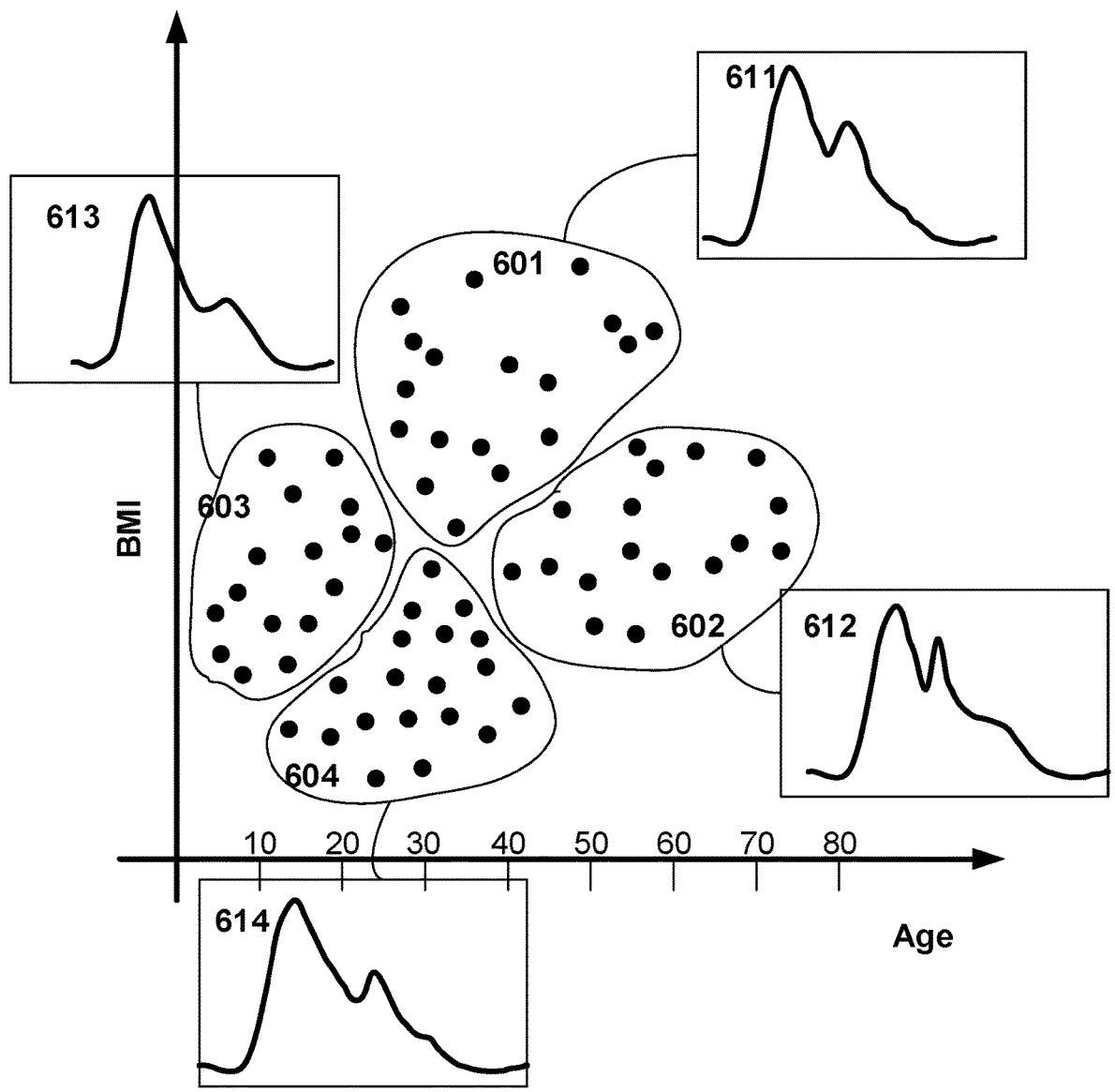
FIG. 6 shows four pulse waveform templates for the four clusters with different morphological features.

FIG. 5 illustrates a process for performing PWA to determine arterial stiffness. Process 500 involves determining the class for a user. The user class may be defined by one or more variables that co-vary with the measurement of arterial stiffness through PWA. Among such variables, the user class may be defined by variables that affect or covary with PPG signal but not with the arterial stiffness, which may help to rule out factors unrelated to arterial stiffness. For instance, the user may be placed into a class based on BMI and age. Other variables co-varying with the measurement of arterial stiffness though PWA may also be used to define the user class. Such variables include but are not limited to: gender, height, weight, ethnicity blood pressure, body fat percentage, other health or disease condition, etc. See Block 502. Process 500 involves providing a pulse waveform template for the user class. See Block 504. In some implementations, a user class includes individuals in a group obtained by one or more clustering techniques. For instance, one or more clustering techniques may be applied to obtain four clusters (601-604) of individuals shown in FIG. 6. The clustering techniques may employ connectivity models, centroid models, distribution models, density models, group models, and graph models. The clustering algorithm may include K-means algorithm, partitioning around medoid, hierarchical clustering, etc. The user class template is obtained from pulse waveforms of the individuals in the class. FIG. 6 shows four pulse waveform templates (611-614) for the four clusters (601-604) with different morphological features. In some implementations, data preprocessing techniques described above are applied to obtain the user class template.

Process 500 continues by obtaining morphological features of pulse waveform of the user using the template of the user class. See Block 506. In some implementations, the morphological features of the user may be obtained as difference values between the user's waveform and the template waveform, which are also referred to as comparison results hereinafter. In other implementations, the morphological features of the user may be normalized relative to the template, and then features are obtained from the normalized waveform.

In some implementations, the process involves determining an arterial stiffness measurement of the user. In some implementations, the process involves applying the comparison results to a model to obtain the arterial stiffness measurement of the user, wherein the model takes the comparison results as inputs and provides a value of an arterial stiffness measurement as an output. See block 508. In some implementations, the model includes a general linear model, a non-linear model, a neural network model, or a regression tree.

Device Configuration

This disclosure is directed at biometric monitoring devices (which may also be referred to herein and in any references incorporated by reference as "biometric tracking devices," "personal health monitoring devices," "portable monitoring devices," "portable biometric monitoring devices," "biometric monitoring devices," or the like), which may be generally described as wearable devices, typically of a small size, that are designed to be worn relatively continuously by a person. When worn, such biometric monitoring devices gather data regarding activities performed by the wearer or the wearer's physiological state. Such data may include data representative of the ambient environment around the wearer or the wearer's interaction with the environment, e.g., motion data regarding the wearer's movements, ambient light, ambient noise, air quality, etc., as well as physiological data obtained by measuring various physiological characteristics of the wearer, e.g., heart rate, perspiration levels, etc.

Biometric monitoring devices, as mentioned above, are typically small in size so as to be unobtrusive for the wearer. Fitbit offers several varieties of biometric monitoring devices that are all quite small and very light, e.g., the Fitbit Flex™ is a wristband with an insertable biometric monitoring device that is about 0.5" wide by 1.3" long by 0.25" thick. Biometric monitoring devices are typically designed to be able to be worn without discomfort for long periods of time and to not interfere with normal daily activity.

In some cases, a biometric monitoring device may leverage other devices external to the biometric monitoring device, e.g., an external pulse waveform monitor or heart rate monitor in the form of an EKG sensor on a chest strap may be used to obtain pulse waveform data or a GPS receiver in a smartphone may be used to obtain position data. In such cases, the biometric monitoring device may communicate with these external devices using wired or wireless communications connections. The concepts disclosed and discussed herein may be applied to both stand-alone biometric monitoring devices as well as biometric monitoring devices that leverage sensors or functionality provided in external devices, e.g., external sensors, sensors or functionality provided by smartphones, etc.

In general, the concepts discussed herein may be implemented in stand-alone biometric monitoring devices as well as, when appropriate, biometric monitoring devices that leverage external devices.

It is to be understood that while the concepts and discussion included herein are presented in the context of biometric monitoring devices, these concepts may also be applied in other contexts as well if the appropriate hardware is available. For example, many modern smartphones include motion sensors, such as accelerometers, that are normally included in biometric monitoring devices, and the concepts discussed herein may, if appropriate hardware is available in a device, be implemented in that device. In effect, this may be viewed as turning the smartphone into some form of biometric monitoring device (although one that is larger than a typical biometric monitoring device and that may not be worn in the same manner). Such implementations are also to be understood to be within the scope of this disclosure.

The functionality discussed herein may be provided using a number of different approaches. For example, in some implementations a processor may be controlled by computer-executable instructions stored in memory so as to provide functionality such as is described herein. In other implementations, such functionality may be provided in the form of an electrical circuit. In yet other implementations, such functionality may be provided by a processor or processors controlled by computer-executable instructions stored in a memory coupled with one or more specially-designed electrical circuits. Various examples of hardware that may be used to implement the concepts outlined herein include, but are not limited to, application specific integrated circuits (ASICs), field-programmable gate arrays (FPGAs), and general-purpose microprocessors coupled with memory that stores executable instructions for controlling the general-purpose microprocessors.

Standalone biometric monitoring devices may be provided in a number of form factors and may be designed to be worn in a variety of ways. In some implementations, a biometric monitoring device may be designed to be insertable into a wearable case or into multiple, different wearable cases, e.g., a wristband case, a belt-clip case, a pendant case, a case configured to be attached to a piece of exercise equipment such as a bicycle, etc. Such implementations are described in more detail in, for example, U.S. patent application Ser. No. 14/029,764, filed Sep. 17, 2013, which is hereby incorporated by reference for such purpose. In other implementations, a biometric monitoring device may be designed to be worn in only one manner, e.g., a biometric monitoring device that is integrated into a wristband in a non-removable manner may be intended to be worn only on a person's wrist (or perhaps ankle).

Figure 7:
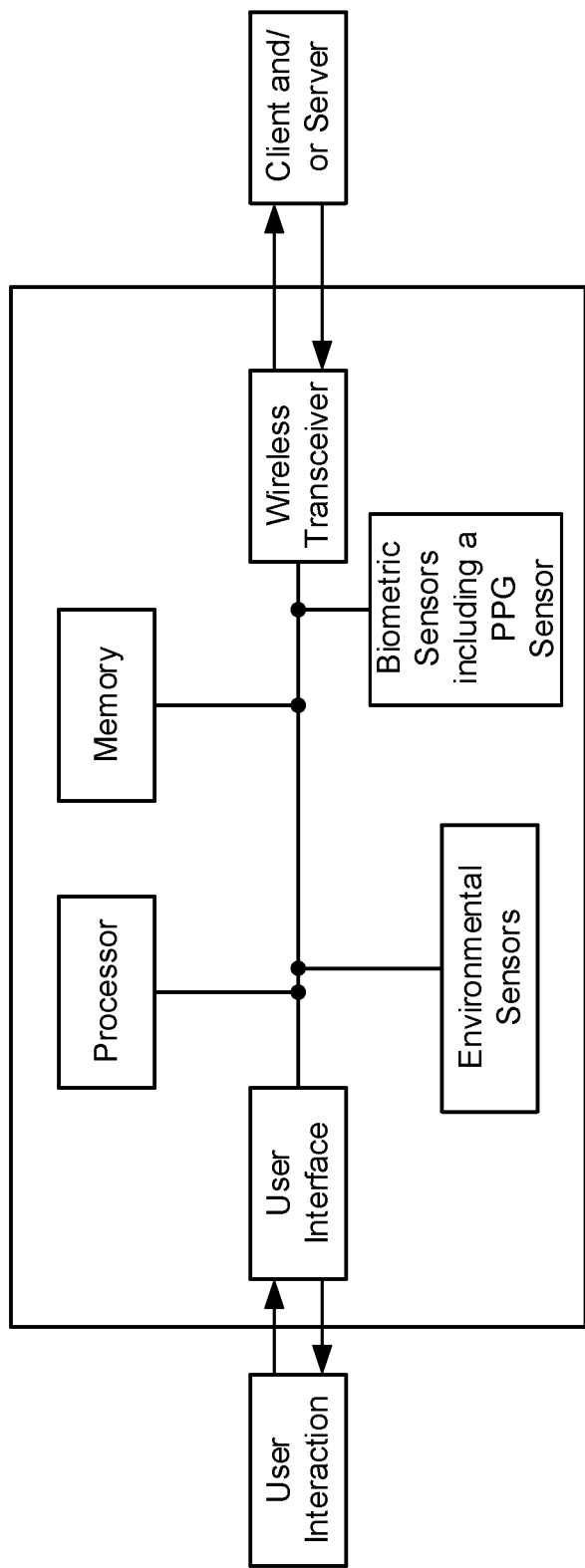
FIG. 7 illustrates an example portable monitoring device which enables user interaction via a user interface.

Portable biometric monitoring devices according to embodiments and implementations described herein may have shapes and sizes adapted for coupling to (e.g., secured to, worn, borne by, etc.) the body or clothing of a user. An example of a wearable biometric monitoring device is shown in FIG. 7; the example portable monitoring device may have a user interface, processor, biometric sensor(s), memory, environmental sensor(s) and/or a wireless transceiver which may communicate with a client and/or server. In various implementations, the biometric sensors include a PPG sensor for generating PWA data.

Figure 8:
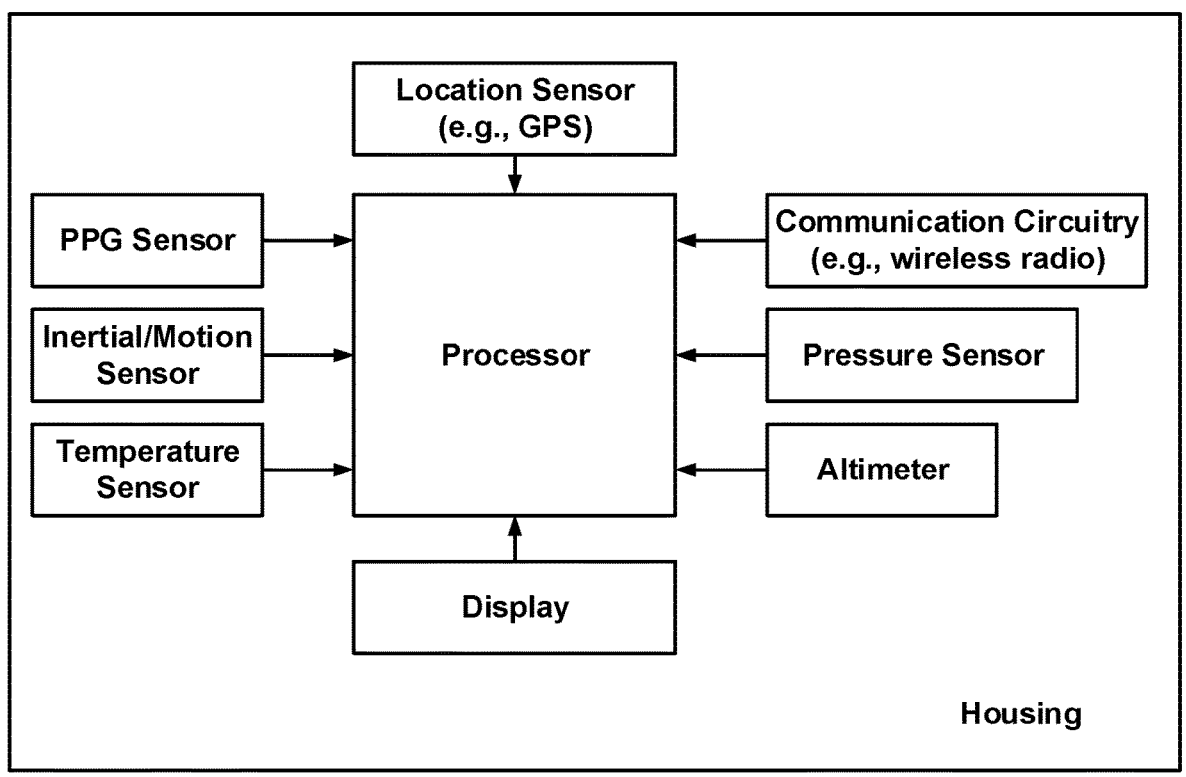
FIG. 8 is a block diagram showing components of a biometric monitoring device in such an implementation.

In some implementations, the wearable biometric monitoring device integrates a plurality of biometric sensors. FIG. 8 is a block diagram showing components of a biometric monitoring device in such an implementation. The biometric monitoring device includes a processor, a display element, communication circuitry, and a plurality of biometric sensors that are communicatively linked and contained in a housing structure. In some implementations, instead of enclosed in a housing, one or more of the sensors may be integrated into auxiliary structure connected to the housing structure. For example, the PPG sensor may be integrated into a wristband that is attached to a housing, providing a device with a form similar to a wrist-watch that can be worn on the wrist. See FIG. 13A. The plurality of the biometric sensors in the example illustrated in FIG. 8 includes a PPG sensor, an inertial or motion sensor, a temperature sensor, a pressure sensor, and optionally an altimeter.

In some implementations, the PPG sensor is configured to collect data for deriving pulse waveforms under operational conditions as described above in association with pulse wave analysis. In some implementations, the PPG sensor can have additional operation modes for collecting data for other biometric measurements such as heartbeat, skin proximity, and skin color.

The wearable biometric monitoring device illustrated here also includes an inertial sensor or a motion sensor that can be used to detect motion or the lack of motion of a user wearing the device. In some implementations, the device can use the motion information to remove motion noise from PDG data used for PWA. In some implementations, the device can use the motion information to determine activities of the user, which activity information can be used in PWA. The inertial sensor can also be used, either alone or in combination with other sensors, the position or orientation of the user's body part to which the device is attached (e.g., the orientation or position of the user's wrist or arm). In some implementations, such information may be used to calibrate the PPG and/or taken into account in PWA.

The wearable biometric monitoring device also includes a temperature sensor that can be used to measure the user's skin temperature, which can be used to normalize PPG data or accounted for in PWA.

The wearable biometric monitoring device also includes a pressure sensor that can be used to measure the pressure between the sensor and the user's tissue, which can affect the features and dynamics of the pulse wave. In some implementations, the measured pressure can be used to normalize PPG data or accounted for in PWA. The pressure sensor may include one or more of the following or combinations thereof: a force sensor, a force sensitive resistor, a mechanical sensor, a load sensor, a load cell, a strain gauge, a piezo sensor, or a membrane potentiometer.

The wearable biometric monitoring device also includes an optional location sensor and an optional altimeter. These sensors are optional in some implementations so they all illustrated by dashed lines.

Figure 9A:
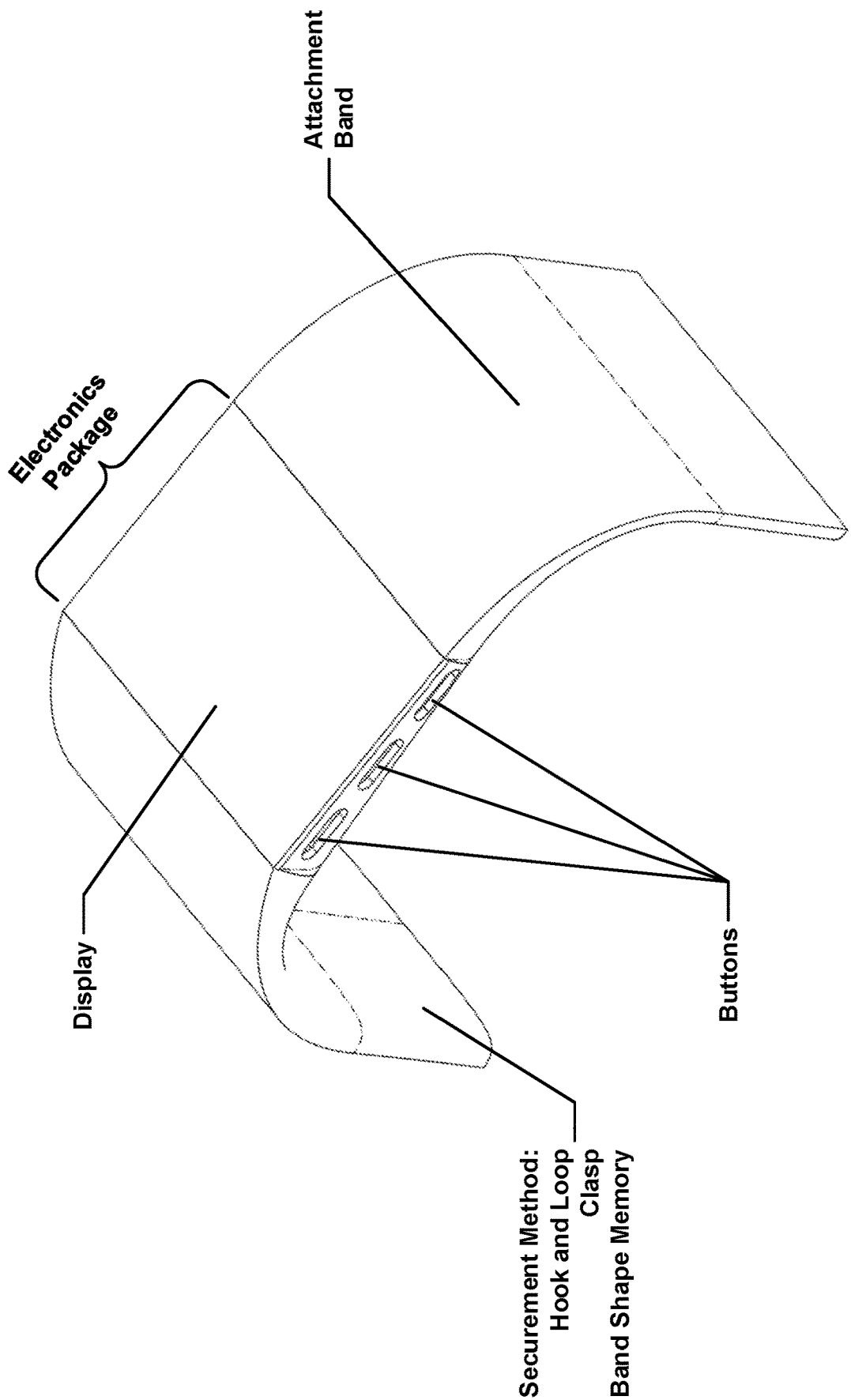
FIG. 9A illustrates an example portable monitoring device which may be secured to the user through the use of a band.
Figure 9B:
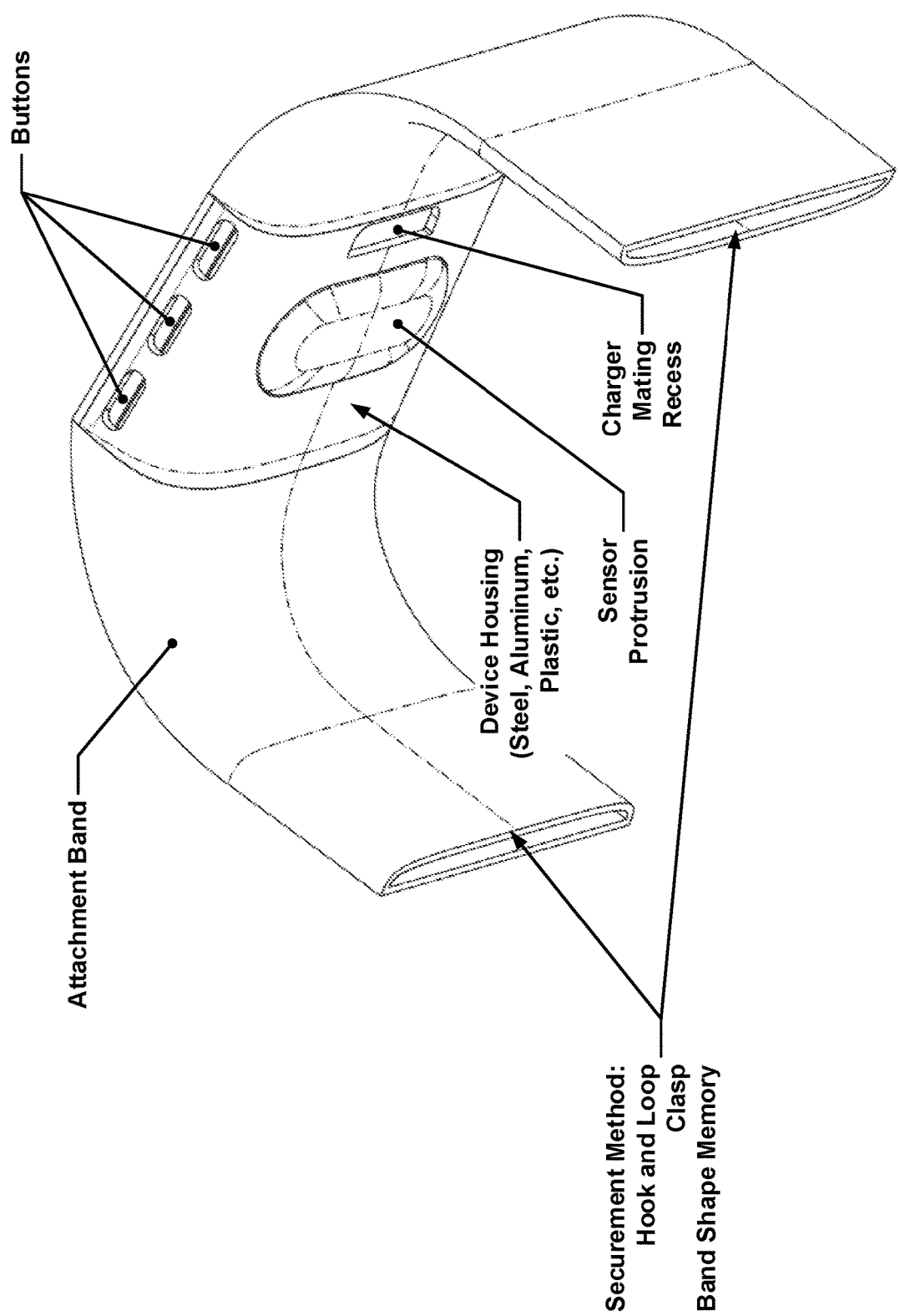
FIG. 9B provides a view of the example portable monitoring device of FIG. 9A which shows the skin-facing portion of the device.
Figure 9C:
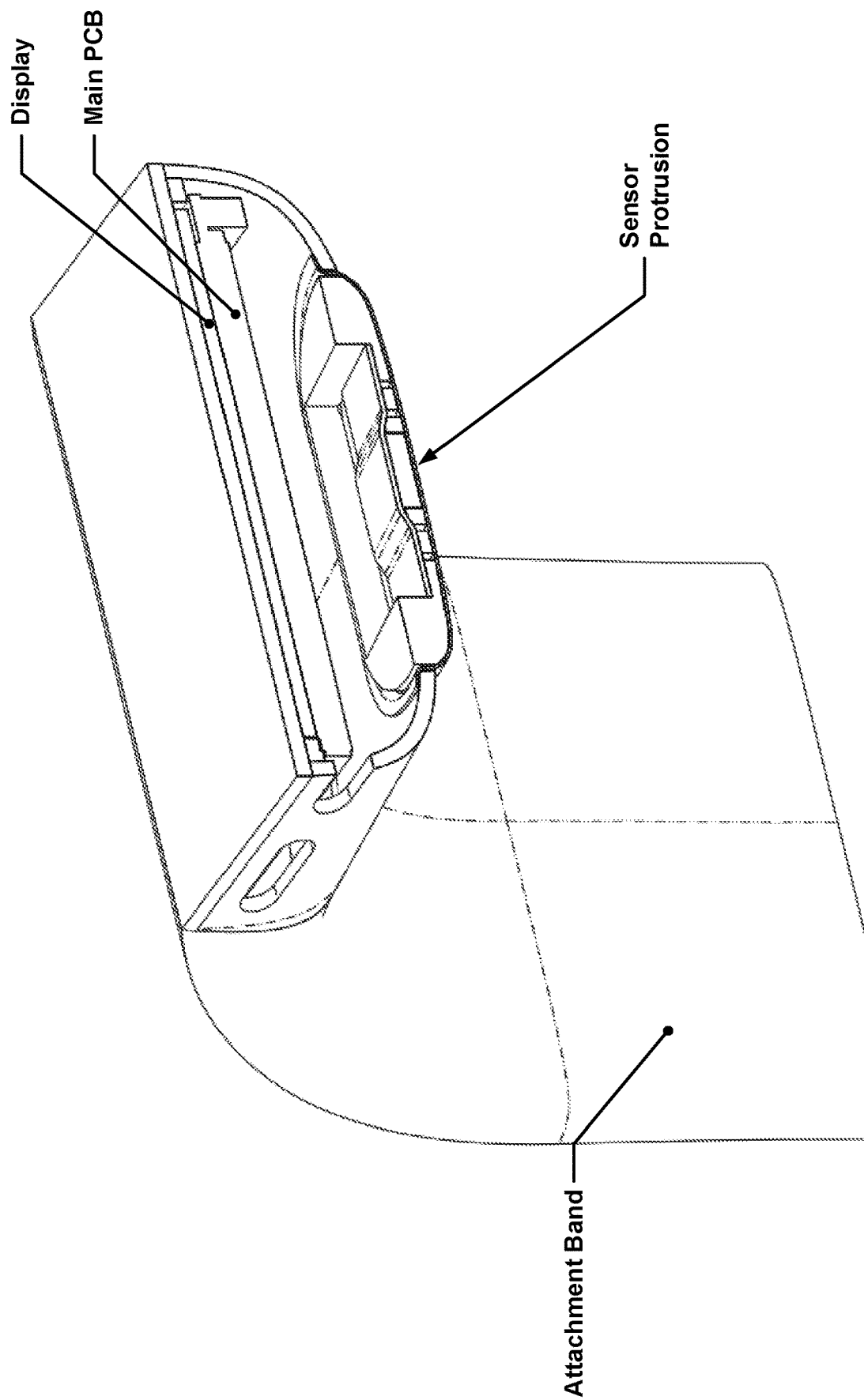
FIG. 9C provides a cross-sectional view of the portable monitoring device of FIG. 9A.

An example of a wrist-worn portable biometric monitoring device is shown in FIGS. 9A through 9C. This device may have a display, button(s), electronics package, and/or an attachment band. The attachment band may be secured to the user through the use of hooks and loops (e.g., Velcro), a clasp, and/or a band having memory of its shape, e.g., through the use of a spring metal band. In FIG. 9B, a sensor protrusion and recess for mating a charger and/or data transmission cable can be seen. In FIG. 9C, a cross-section through the electronics package is shown. Of note are the sensor protrusion, main PCB board, and display.

Portable biometric monitoring devices may collect one or more types of physiological and/or environmental data from embedded sensors and/or external devices and communicate or relay such information to other devices, including devices capable of serving as an Internet-accessible data sources, thus permitting the collected data to be viewed, for example, using a web browser or network-based application. For example, while the user is wearing a biometric monitoring device, the biometric monitoring device may calculate and store the user's step count using one or more biometric sensors. The biometric monitoring device may then transmit data representative of the user's step count to an account on a web service (e.g., www.fitbit.com), computer, mobile phone, or health station where the data may be stored, processed, and visualized by the user. Indeed, the biometric monitoring device may measure or calculate a plurality of other physiological metrics in addition to, or in place of, the user's step count. These include, but are not limited to, energy expenditure, e.g., calorie burn, floors climbed and/or descended, heart rate, heart rate variability, heart rate recovery, location and/or heading, e.g., through GPS, GLONASS, or a similar system, elevation, ambulatory speed and/or distance traveled, swimming lap count, swimming stroke type and count detected, bicycle distance and/or speed, blood pressure, blood glucose, skin conduction, skin and/or body temperature, muscle state measured via electromyography, brain activity as measured by electroencephalography, weight, body fat, caloric intake, nutritional intake from food, medication intake, sleep periods, e.g., clock time, sleep phases, sleep quality and/or duration, pH levels, hydration levels, respiration rate, and other physiological metrics. The biometric monitoring device may also measure or calculate metrics related to the environment around the user such as barometric pressure, weather conditions (e.g., temperature, humidity, pollen count, air quality, rain/snow conditions, wind speed), light exposure (e.g., ambient light, UV light exposure, time and/or duration spent in darkness), noise exposure, radiation exposure, and magnetic field. Furthermore, the biometric monitoring device or the system collating the data streams from the biometric monitoring device may calculate metrics derived from such data. For example, the device or system may calculate the user's stress and/or relaxation levels through a combination of heart rate variability, skin conduction, noise pollution, and sleep quality. In another example, the device or system may determine the efficacy of a medical intervention, e.g., medication, through the combination of medication intake, sleep data, and/or activity data. In yet another example, the biometric monitoring device or system may determine the efficacy of an allergy medication through the combination of pollen data, medication intake, sleep and/or activity data. These examples are provided for illustration only and are not intended to be limiting or exhaustive. Further embodiments and implementations of sensor devices may be found in U.S. Pat. No. 9,042,971, titled "Biometric Monitoring Device with Pulse waveform measurement or heart rate measurement Activated by a Single User Gesture" and filed on Jan. 13, 2014, U.S. Pat. No. 9,044,149, titled "Pulse waveform data Collection" and filed on May 29, 2014, U.S. Pat. No. 8,948,832, titled "Wearable Pulse waveform monitor or heart rate monitor" and filed on May 30, 2014, U.S. patent application Ser. No. 13/156,304, titled "Portable Biometric Monitoring Devices and Methods of Operating Same" filed on Jun. 8, 2011 and U.S. Patent Application 61/680,230, titled "Fitbit Tracker" filed Aug. 6, 2012, which are hereby incorporated herein by reference in their entireties.

Physiological Sensors

Biometric monitoring devices as discussed herein may use one, some or all of the following sensors to acquire physiological data, including, but not limited to, the physiological data outlined in the table below. All combinations and permutations of physiological sensors and/or physiological data are intended to fall within the scope of this disclosure. Biometric monitoring devices may include but are not limited to types of one, some, or all of the sensors specified below for the acquisition of corresponding physiological data; indeed, other type(s) of sensors may also or alternatively be employed to acquire the corresponding physiological data, and such other types of sensors are also intended to fall within the scope of the present disclosure. Additionally, the biometric monitoring device may derive the physiological data from the corresponding sensor output data, but is not limited to the number or types of physiological data that it could derive from said sensor.

| Physiological Sensors | Physiological data acquired |
|---|---|
| Optical Reflectometer | Heart Rate, Heart Rate Variability |
| Example Sensors: | SpO₂ (Saturation of Peripheral Oxygen) |
| Light emitter and receiver | Respiration |
| Multi or single LED and | Stress |
| photo diode arrangement | Blood pressure |
| Wavelength tuned for | Arterial Stiffness |
| specific physiological | Blood glucose levels |
| signals | Blood volume |
| Synchronous detection/ | Heart rate recovery |
| amplitude modulation | Cardiac health |
| Motion Detector | Activity level detection |
| Example Sensors: | Sitting/standing detection |
| Inertial sensors, Gyroscopic | Fall detection |
| sensors, and/or Accelerometers | |
| GPS | |
| Skin Temperature | Stress |
| EMG (electromyographic sensor) | Muscle tension |
| EKG or ECG (electrocardiographic sensor) | Heart Rate |
| Example Sensors: | Heart Rate Variability |
| Single-lead ECG or EKG | Heart Rate Recovery |
| Dual-lead ECG or EKG | Stress |
| | Cardiac health |
| Magnetometer | Activity level based on rotation |
| Laser Doppler | |
| Power Meter | |
| Ultrasonic Sensor | Blood flow |
| Audio Sensor | Heart Rate |
| | Heart Rate Variability |
| | Heart Rate Recovery |
| | Laugh detection |
| | Respiration |
| | Respiration type e.g., snoring, breathing, breathing problems (such as sleep apnea) |
| | User's voice |
| Strain gauge | Heart Rate |
| Example: | Heart Rate Variability |
| In a wrist band | Stress |
| Wet/Immersion Sensor | Stress |
| Example Sensor: | Swimming detection |
| Galvanic skin response | Shower detection |

In one example embodiment, the biometric monitoring device may include an optical sensor to detect, sense, sample and/or generate data that may be used to determine information representative of, for example, stress (or level thereof), blood pressure, and/or heart rate of a user. (See, for example, FIGS. 9A through 10C and 18A through KKG). In such embodiments, the biometric monitoring device may include an optical sensor having one or more light sources (LED, laser, etc.) to emit or output light into the user's body, as well as light detectors (photodiodes, phototransistors, etc.) to sample, measure and/or detect a response or reflection of such light from the user's body and provide data used to determine data that is representative of stress (or level thereof), blood pressure, and/or heart rate of a user (e.g., such as by using photoplethysmography).

In one example embodiment, a user's pulse waveform measurement or heart rate measurement may be triggered by criteria determined by one or more sensors (or processing circuitry connected to them). For instance, when data from a motion sensor(s) indicates a period of stillness or of little motion, the biometric monitoring device may trigger, acquire, and/or obtain a pulse waveform measurement or heart rate measurement or data. (See, for example, FIGS. 16, 19A, and 19B).

Figure 19A:
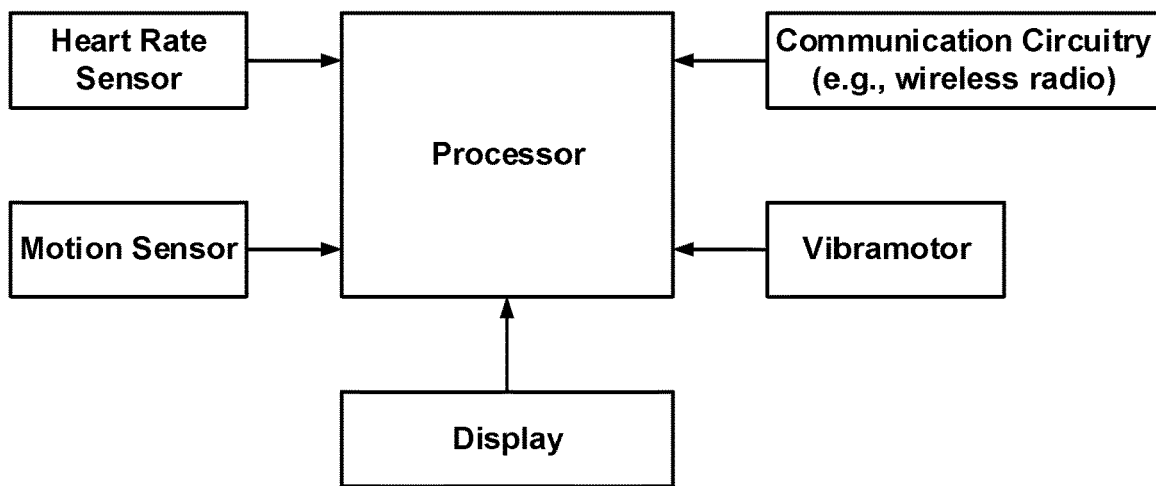
FIG. 19A is a schematic diagram of an example of a portable biometric monitoring device having a heart rate or PPG sensor, motion sensor, display, vibromotor, and communication circuitry which is connected to a processor.

FIG. 19A illustrates an example of a portable biometric monitoring device having a heart rate or PPG sensor, motion sensor, display, vibromotor, and communication circuitry which is connected to a processor.

Figure 19B:
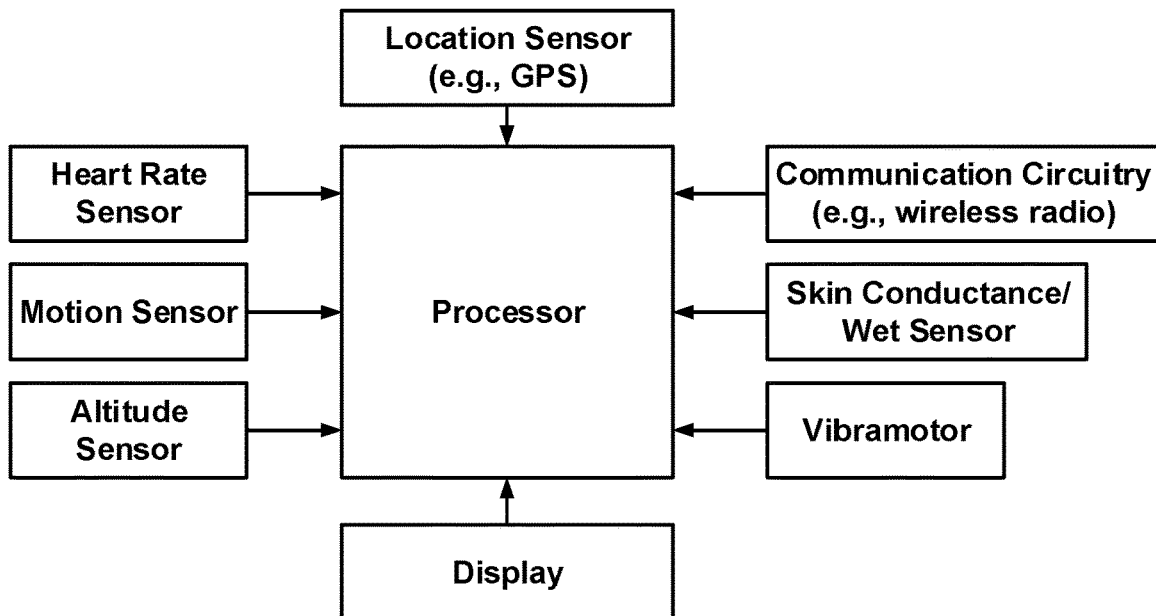
FIG. 19B is a schematic diagram of an example of a portable biometric monitoring device having a heart rate or PPG sensor, motion sensor, display, vibromotor, location sensor, altitude sensor, skin conductance/wet sensor and communication circuitry which is connected to a processor.

FIG. 19B illustrates an example of a portable biometric monitoring device having a heart rate or PPG sensor, motion sensor, display, vibromotor, location sensor, altitude sensor, skin conductance/wet sensor and communication circuitry which is connected to a processor.

In one embodiment, when the motion sensor(s) indicate user activity or motion (for example, motion that is not suitable or optimum to trigger, acquire, and/or obtain desired pulse waveform measurement or heart rate measurement or data (for example, data used to determine a user's resting heart rate)), the biometric monitoring device and/or the sensor(s) employed to acquire and/or obtain a desired pulse waveform measurement or heart rate measurement or data may be placed in, or remain in, a low power state. Since pulse waveform measurement or heart rate measurements taken during motion may be less reliable and may be corrupted by motion artifacts, it may be desirable to decrease the frequency with which pulse waveform data samples are collected (thus decreasing power usage) when the biometric monitoring device is in motion.

In another embodiment, a biometric monitoring device may employ data (for example, from one or more motion sensors) indicative of user activity or motion to adjust or modify characteristics of triggering, acquiring, and/or obtaining desired pulse waveform measurement or heart rate measurements or data (for example, to improve robustness to motion artifact). For instance, if the biometric monitoring device receives data indicative of user activity or motion, the biometric monitoring device may adjust or modify the sampling rate and/or resolution mode of sensors used to acquire pulse waveform data (for example, where the amount of user motion exceeds a certain threshold, the biometric monitoring device may increase the sampling rate and/or increase the sampling resolution mode of sensors employed to acquire pulse waveform measurement or heart rate measurement or data.) Moreover, the biometric monitoring device may adjust or modify the sampling rate and/or resolution mode of the motion sensor(s) during such periods of user activity or motion (for example, periods where the amount of user motion exceeds a certain threshold). In this way, when the biometric monitoring device determines or detects such user activity or motion, the biometric monitoring device may place the motion sensor(s) into a higher sampling rate and/or higher sampling resolution mode to, for example, enable more accurate adaptive filtering of the heart rate signal. (See, for example, FIG. 16).

Figure 16:
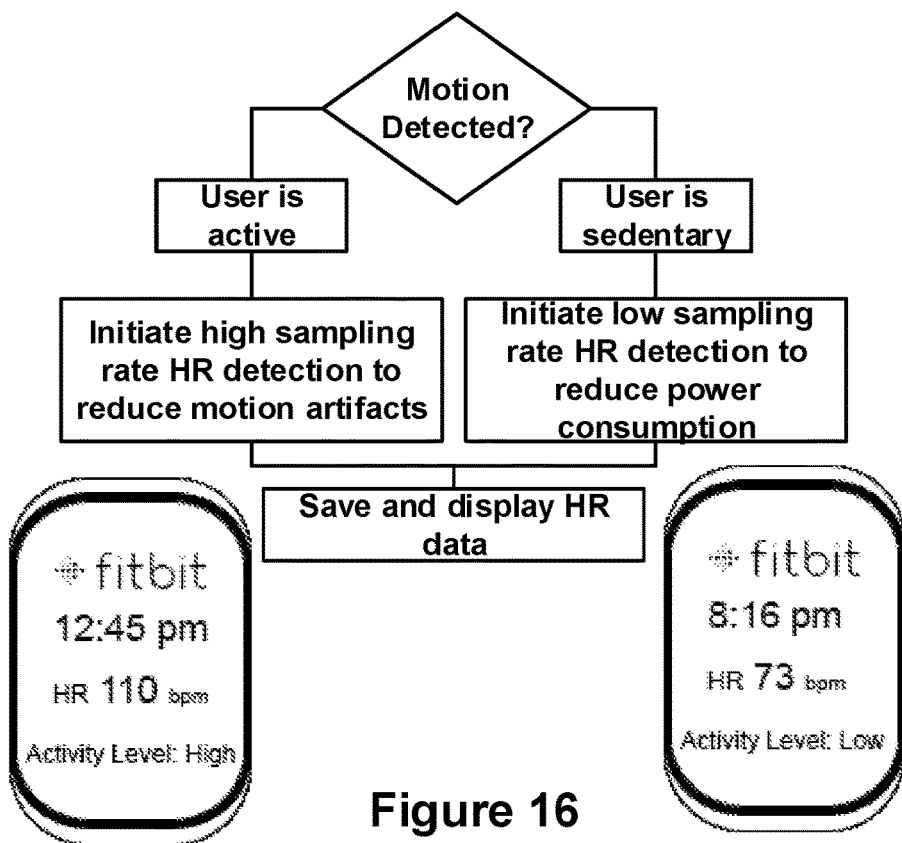
FIG. 16 illustrates an example of a portable biometric monitoring device that changes how it detects a user's heart rate based on how much movement the biometric monitoring device is experiencing.

FIG. 16 illustrates an example of a portable biometric monitoring device that changes how it detects a user's heart rate based on how much movement the biometric monitoring device is experiencing. In the case where there is motion detected (e.g., through the use of an accelerometer), the user may be considered by the biometric monitoring device to be "active" and high-sampling-rate heart rate detection may occur to reduce motion artifacts in the pulse waveform measurement or heart rate measurement. This data may be saved and/or displayed. In the case that the user is determined by the biometric monitoring device to not be moving (or to be relatively sedentary), low-sampling-rate heart rate detection (which does not consume as much power) may be adequate to measure a heart rate and may thus be used.

Notably, where a biometric monitoring device employs optical techniques to acquire pulse waveform measurement or heart rate measurements or data, e.g., by using photoplethysmography, a motion signal may be employed to determine or establish a particular approach or technique to data acquisition or measurement by the heart rate or pulse wave sensor (e.g., synchronous detection rather than a non-amplitude-modulated approach) and/or analysis thereof. (See, for example, FIG. 18E). In this way, the data which is indicative of the amount of user motion or activity may cause the biometric monitoring device to establish or adjust the type or technique of data acquisition or measurement used by an optical pulse waveform sensor or sensors.

For example, in one embodiment, a biometric monitoring device (or heart-rate measurement technique as disclosed herein may adjust and/or reduce the sampling rate of optical heart rate sampling when motion detector circuitry detects or determines that the biometric monitoring device wearer's motion is below a threshold (for example, if the biometric monitoring device determines the user is sedentary or asleep). (See, for example, FIG. 16). In this way, the biometric monitoring device may control its power consumption. For example, the biometric monitoring device may reduce power consumption by reducing the sensor sampling rate—for instance, the biometric monitoring device may sample the heart rate (via the pulse waveform sensor) once every 10 minutes, or 10 seconds out of every 1 minute. Notably, the biometric monitoring device may, in addition thereto or in lieu thereof, control power consumption via controlling data processing circuitry analysis and/or data analysis techniques in accordance with motion detection. As such, the motion of the user may impact the heart rate or pulse waveform data acquisition parameters and/or data analysis or processing thereof.

Motion Artifact Suppression in Pulse Waveform Sensors

As discussed above, the raw heart rate signal measured by a PPG sensor may be improved by using one or more algorithms to remove motion artifacts. Movement of the user (for determining motion artifacts) may be measured using sensors including, but not limited to, accelerometers, gyroscopes, proximity detectors, magnetometers, etc. The goal of such algorithms is to remove components os the PPG signal attributable to movement (movement artifacts) using the movement signal captured from the other sensors as a guide. In one embodiment the movement artifacts in the PPG signal may be removed using an adaptive filter based on a hybrid Kalman filter and a least mean square filter or a recursive least squares filter. The heart rate may then be extracted from the cleaned/filtered signal using a peak counting algorithm or a power spectral density estimation algorithm. Alternatively, a Kalman filter or particle filter may be used to remove such movement artifacts.

Another approach that may be used to calculate the heart rate frequency is to create a model of the heart rate signal as $Y=Y_{dc}+\Sigma a_k*\cos k\theta+b_k*\sin k\theta$, where k is the order of harmonic components, and $\theta$ is a model parameter for heart rate. This model may then be fit to the signal using either an extended Kalman filter or a particle filter. This model exploits the fact that the signal is not sinusoidal so contains power both at the fundamental harmonic as well as multiple additional harmonics.

Alternately, the signal may be modeled as $Y=Y_{dc}+\Sigma a_k*\sin(k*w_{motion}t+\theta)+\Sigma b_k*\sin(k*w_{HR}t+\emptyset)$, where $w_{motion}$ is estimated directly from the accelerometer signal (or another motion sensor signal).

Sedentary, Sleep, and Active Classified Metrics

In yet another example embodiment, the biometric monitoring device may employ sensors to calculate heart rate variability when the device determines the user to be sedentary or asleep. Here, the biometric monitoring device may operate the sensors in a higher-rate sampling mode (relative to non-sedentary periods or periods of user activity that exceed a predetermined threshold) to calculate heart rate variability. The biometric monitoring device (or an external device) may employ heart rate variability as an indicator of cardiac health or stress.

Indeed, in some embodiments, the biometric monitoring device may measure and/or determine the user's stress level and/or cardiac health when the user is sedentary and/or asleep (for example, as detected and/or determined by the biometric monitoring device). Some embodiments of a biometric monitoring device of the present disclosure may determine the user's stress level, health state (e.g., risk, onset, or progression of fever or cold), and/or cardiac health using sensor data that is indicative of the heart rate variability, galvanic skin response, skin temperature, body temperature, and/or heart rate. In this way, processing circuitry of the biometric monitoring device may determine and/or track the user's "baseline" stress levels over time and/or cardiac "health" over time. In another embodiment, the device may measure a physiologic parameter of the user during one or more periods where the user is motionless (or the user's motion is below a predetermined threshold), such as when the user is sitting, lying down, asleep, or in a sleep stage (e.g., deep sleep). Such data may also be employed by the biometric monitoring device as a "baseline" for stress-related parameters, health-related parameters (e.g., risk or onset of fever or cold), cardiac health, heart rate variability, galvanic skin response, skin temperature, body temperature and/or heart rate.

Sleep Monitoring

In some embodiments, the biometric monitoring device may automatically detect or determine when the user is attempting to go to sleep, is entering sleep, is asleep, and/or is awoken from a period of sleep. In such embodiments, the biometric monitoring device may employ physiological sensors to acquire data and the data processing circuitry of the biometric monitoring device may correlate a combination of heart rate, heart rate variability, respiration rate, galvanic skin response, motion, skin temperature, and/or body temperature data collected from sensors of the biometric monitoring device to detect or determine if the user is attempting to go to sleep, is entering sleep, is asleep, and/or is awoken from a period of sleep. In response, the biometric monitoring device may, for example, acquire physiological data (of the types, and in the manners, as described herein) and/or determine physiological conditions of the user (of the types, and in the manners, as described herein). For example, a decrease or cessation of user motion combined with a reduction in user heart rate and/or a change in heart rate variability may indicate that the user has fallen asleep. Subsequent changes in heart rate variability and galvanic skin response may then be used by the biometric monitoring device to determine transitions of the user's sleep state between two or more stages of sleep (for example, into lighter and/or deeper stages of sleep). Motion by the user and/or an elevated heart rate and/or a change in heart rate variability may be used by the biometric monitoring device to determine that the user has awoken.

Real-time, windowed, or batch processing to may be used to determine the transitions between wake, sleep, and sleep stages. For instance, a decrease in heart rate may be measured in a time window where the heart rate is elevated at the start of the window and reduced in the middle (and/or end) of the window. The awake and sleep stages may be classified by a hidden Markov model using changes in motion signal (e.g., decreasing motion intensity), heart rate, heart rate variability, skin temperature, galvanic skin response, and/or ambient light levels. The transition points may be determined through a changepoint algorithm (e.g., Bayesian changepoint analysis). The transition between awake and sleep may be determined by observing periods where the user's heart rate decreases over a predetermined time duration by at least a certain threshold but within a predetermined margin of the user's resting heart rate (that is observed as, for example, the minimum heart rate of the user while sleeping). Similarly, the transition between sleep and awake may be determined by observing an increase in the user's heart rate above a predetermined threshold of the user's resting heart rate.

In some embodiments, the biometric monitoring device may be one component of a system for monitoring sleep, where the system includes a secondary device configured to communicate with the biometric monitoring device and adapted to be placed near the sleeper (e.g., an alarm clock). The secondary device may, in some implementations, have a shape and mechanical and/or magnetic interface to accept the biometric monitoring device for safe keeping, communication, and/or charging. However, the secondary device may also be generic to the biometric monitoring device, e.g., a smartphone that is not specifically designed to physically interface with the biometric monitoring device. The communication between the biometric monitoring device and the secondary device may be provided through wired communication interfaces or through wireless communication interfaces and protocols such as Bluetooth (including, for example, Bluetooth 4.0 and Bluetooth Low Energy protocols), RFID, NFC, or WLAN. The secondary device may include sensors to assist in sleep monitoring or environmental monitoring such as, for example, sensors that measure ambient light, noise and/or sound (e.g., to detect snoring), temperature, humidity, and air quality (pollen, dust, $CO_2$, etc.). In one embodiment, the secondary device may communicate with an external service such as www.fitbit.com or a server (e.g., a personal computer). Communication with the secondary device may be achieved through wired (e.g., Ethernet, USB) or wireless (e.g., WLAN, Bluetooth, RFID, NFC, cellular) circuitry and protocols to transfer data to and/or from the secondary device. The secondary device may also act as a relay to transfer data to and/or from the biometric monitoring device to and/or from an external service such as www.fitbit.com or other service (e.g., data such as news, social network updates, email, calendar notifications) or server (e.g., personal computer, mobile phone, tablet). Calculation of the user's sleep data may be performed on one or both devices or an external service (e.g., a cloud server) using data from one or both devices.

The secondary device may be equipped with a display to display data obtained by the secondary device or data transferred to it by the biometric monitoring device, the external service, or a combination of data from the biometric monitoring device, the secondary device, and/or the external service. For example, the secondary device may display data indicative of the user's heart rate, total steps for the day, activity and/or sleep goal achievement, the day's weather (measured by the secondary device or reported for a location by an external service), etc. In another example, the secondary device may display data related to the ranking of the user relative to other users, such as total weekly step count. In yet another embodiment, the biometric monitoring device may be equipped with a display to display data obtained by the biometric monitoring device, the secondary device, the external service, or a combination of the three sources. In embodiments where the first device is equipped with a wakeup alarm (e.g., vibramotor, speaker), the secondary device may act as a backup alarm (e.g., using an audio speaker). The secondary device may also have an interface (e.g., display and buttons or touch screen) to create, delete, modify, or enable alarms on the first and/or the secondary device.

Sensor-Based Standby Mode

In another embodiment, the biometric monitoring device may automatically detect or determine whether it is or is not attached to, disposed on, and/or being worn by a user. In response to detecting or determining that the biometric monitoring device is not attached to, disposed on, and/or being worn by a user, the biometric monitoring device (or selected portions thereof) may implement or be placed in a low power mode of operation—for example, the optical pulse waveform sensor and/or circuitry may be placed in a lower power or sleep mode. For example, in one embodiment, the biometric monitoring device may include one or more light detectors (photodiodes, phototransistors, etc.). If, at a given light intensity setting (for example, with respect to the light emitted by a light source that is part of the biometric monitoring device), one or more light detectors provides a low return signal, the biometric monitoring device may interpret the data as indicative of the device not being worn. Upon such a determination, the device may reduce its power consumption—for example, by "disabling" or adjusting the operating conditions of the stress and/or heart rate detection sensors and/or circuitry in addition to other device circuitry or displays (for example, by reducing the duty cycle of or disabling the light source(s) and/or detector(s), turning off the device display, and/or disabling or attenuating associated circuitry or portions thereof). In addition, the biometric monitoring device may periodically determine (e.g., once per second) if the operating conditions of the stress and/or heart rate detection sensors and/or associated circuitry should be restored to a normal operating condition (for example, light source(s), detector(s) and/or associated circuitry should return to a normal operating mode for heart rate detection). In another embodiment, the biometric monitoring device may restore the operating conditions of the stress and/or heart rate detection sensors and/or associated circuitry upon detection of a triggerable event—for example, upon detecting motion of the device (for example, based on data from one or more motion sensor(s)) and/or detecting a user input via the user interface (for example, a tap, bump or swipe interaction with the biometric monitoring device). In some related embodiments, the biometric monitoring device may, for power saving purposes, reduce its default rate of pulse waveform measurement or heart rate measurement collection to, for instance, one measurement per minute while the user is not highly active and the user may have the option of putting the device into a mode of operation to generate measurements on demand or at a faster rate (e.g., once per second), for instance, by pushing a button.

Optical Sensor(s)

In one embodiment, the optical sensors (sources and/or detectors) may be disposed on an interior or skin-side of the biometric monitoring device (i.e., a side of the biometric monitoring device that contacts, touches, and/or faces the skin of the user (hereinafter "skin-side"). (See, for example, FIGS. 9A through 10C). In another embodiment, the optical sensors may be disposed on one or more sides of the device, including the skin-side and one or more sides of the device that face or are exposed to the ambient environment (environmental side). (See, for example, FIGS. 13A through 14).

Optical sensors such as PPG sensors may be used to obtain data that can be analyzed to obtain pulse waveforms or heartbeat waveform. The data used for obtaining pulse waveform for PWA may be collected under different operational mode than data used for heartbeat analysis. For example, PWA data in some implementations require higher sampling frequency. Furthermore, pulse wave analysis may require morphological features that are necessary in heartbeat analysis.

Figure 13A:
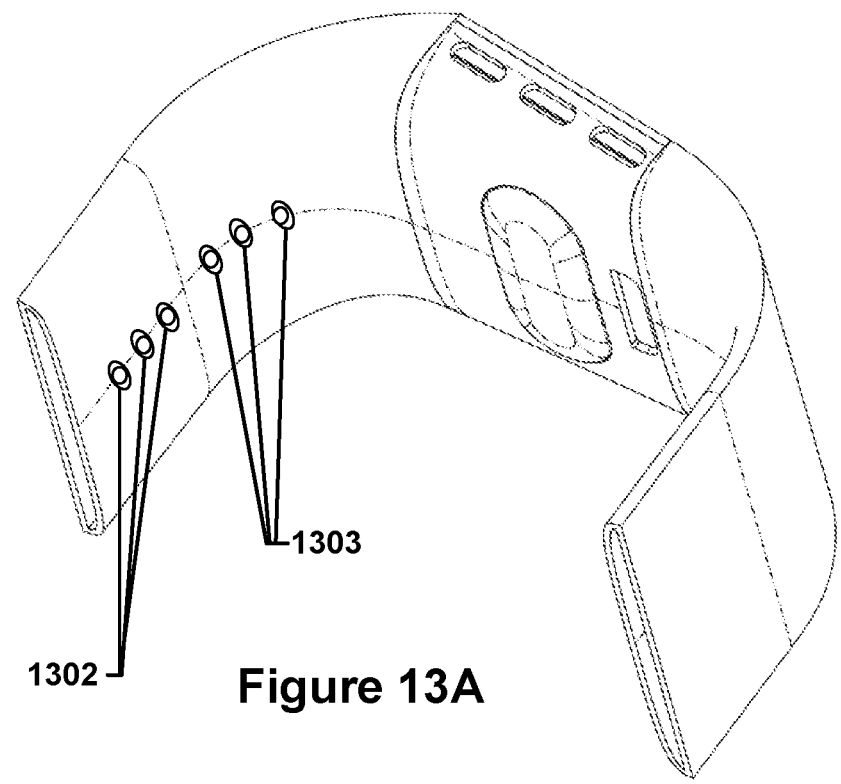
FIG. 13A illustrates an example of a portable monitoring device having a band; optical sensors and light emitters may be placed on the band.

FIG. 13A illustrates an example of a portable monitoring device having a band; optical sensors and light emitters may be placed on the band.

Figure 13B:
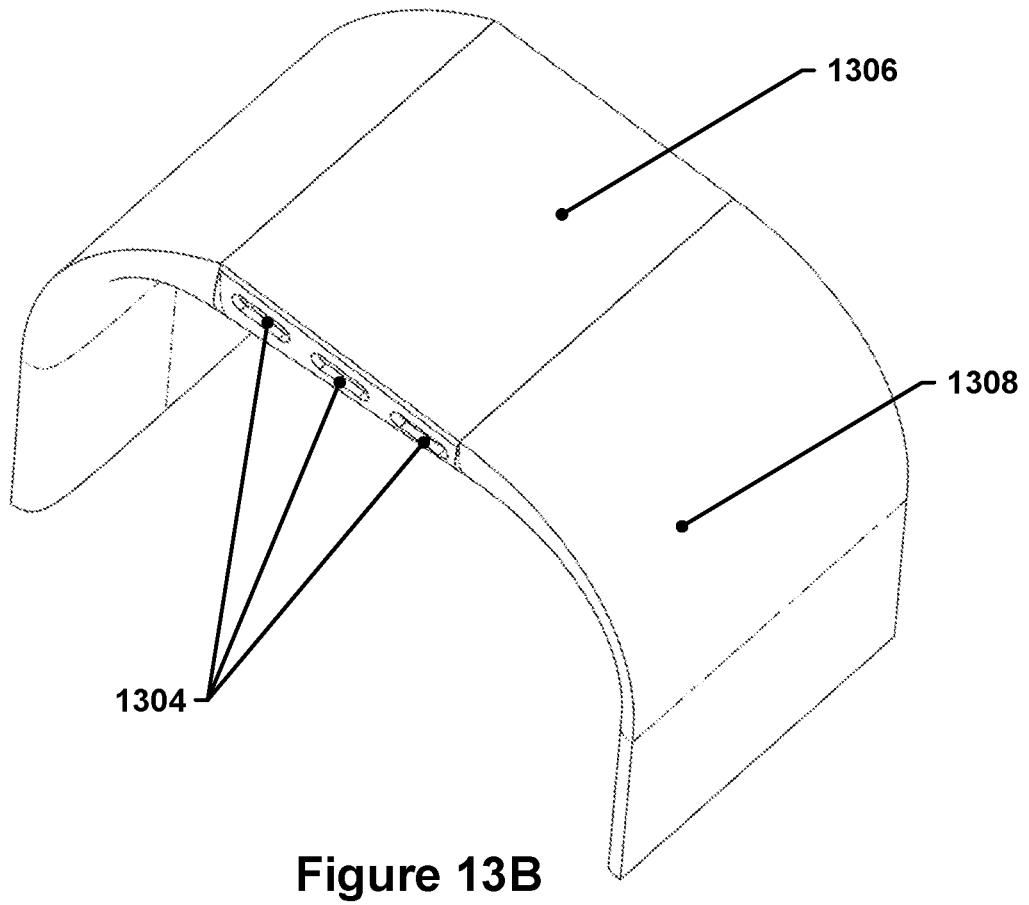
FIG. 13B illustrates an example of a portable biometric monitoring device having a display and wristband. Additionally, optical PPG (e.g., heart rate) detection sensors and/or emitters may be located on the side of the biometric monitoring device. In one embodiment, these may be located in side-mounted buttons.

FIG. 13B illustrates an example of a portable biometric monitoring device having a display and wristband. Additionally, optical PPG (e.g., heart rate) detection sensors and/or emitters may be located on the side of the biometric monitoring device. In one embodiment, these may be located in side-mounted buttons.

Figure 14:
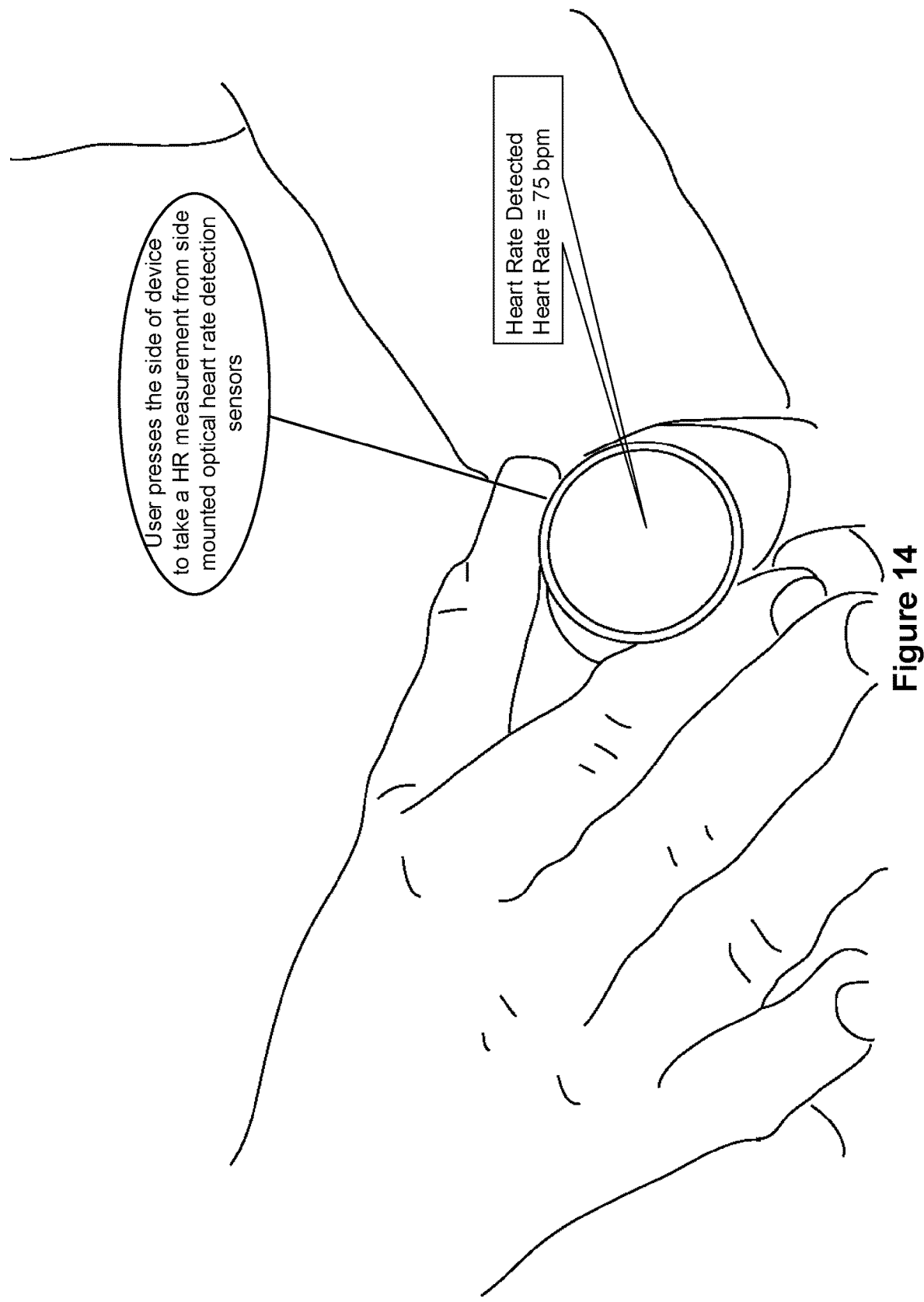
FIG. 14 depicts a user pressing the side of a portable biometric monitoring device to take a heart rate measurement from a side-mounted optical heart rate detection sensor. The display of the biometric monitoring device may show whether or not the heart rate has been detected and/or display the user's heart rate.

FIG. 14 depicts a user pressing the side of a portable biometric monitoring device to take a pulse waveform measurement or heart rate measurement from a side-mounted optical heart rate detection sensor. The display of the biometric monitoring device may show whether or not the heart rate has been detected and/or display the user's heart rate.

Notably, the data from such optical sensors may be representative of physiological data and/or environmental data. Indeed, in one embodiment, the optical sensors provide, acquire and/or detect information from multiple sides of the biometric monitoring device whether or not the sensors are disposed on one or more of the multiple sides. For example, the optical sensors may obtain data related to the ambient light conditions of the environment.

Where optical sensors are disposed or arranged on the skin-side of the biometric monitoring device, in operation, a light source in the biometric monitoring device may emit light upon the skin of the user and, in response, a light detector in the biometric monitoring device may sample, acquire, and/or detect corresponding reflected and/or emitted light from the skin (and from inside the body). The one or more light sources and light detectors may be arranged in an array or pattern that enhances or optimizes the signal-to-noise ratio and/or serves to reduce or minimize power consumption by the light sources and light detectors. These optical sensors may sample, acquire and/or detect physiological data which may then be processed or analyzed (for example, by resident processing circuitry) to obtain data that is representative of, for example, a user's heart rate, respiration, heart rate variability, oxygen saturation ($SpO_2$), blood volume, blood glucose, skin moisture, and/or skin pigmentation level.

The light source(s) may emit light having one or more wavelengths that are specific or directed to a type of physiological data to be collected. Similarly, the optical detectors may sample, measure and/or detect one or more wavelengths that are also specific or directed to a type of physiological data to be collected and/or a physiological parameter (of the user) to be assessed or determined. For instance, in one embodiment, a light source emitting light having a wavelength in the green spectrum (for example, an LED that emits light having wavelengths corresponding to the green spectrum) and a photodiode positioned to sample, measure, and/or detect a response or reflection corresponding with such light may provide data that may be used to determine or detect heart rate. In contrast, a light source emitting light having a wavelength in the red spectrum (for example, an LED that emits light having wavelengths corresponding to the red spectrum) and a light source emitting light having a wavelength in the infrared spectrum (for example, an LED that emits light having wavelengths corresponding to the IR spectrum) and photodiode positioned to sample, measure and/or detect a response or reflection of such light may provide data used to determine or detect $SpO_2$.

Indeed, in some embodiments, the color or wavelength of the light emitted by the light source, e.g., an LED (or set of LEDs), may be modified, adjusted, and/or controlled in accordance with a predetermined type of physiological data being acquired or conditions of operation. Here, the wavelength of the light emitted by the light source may be adjusted and/or controlled to optimize and/or enhance the "quality" of the physiological data obtained and/or sampled by the detector. For example, the color of the light emitted by the LED may be switched from infrared to green when the user's skin temperature or the ambient temperature is cool in order to enhance the signal corresponding to cardiac activity. (See, for example, FIG. 18D).

The biometric monitoring device, in some embodiments, may include a window (for example, a window that is, to casual inspection, opaque) in the housing to facilitate optical transmission between the optical sensors and the user. Here, the window may permit light (for example, of a selected wavelength) to be emitted by, for example, one or more LEDs, onto the skin of the user and a response or reflection of that light to pass back through the window to be sampled, measured, and/or detected by, for example, one or more photodiodes. In one embodiment, the circuitry related to emitting and receiving light may be disposed in the interior of the device housing and underneath or behind a plastic or glass layer (for example, painted with infrared ink) or an infrared lens or filter that permits infrared light to pass but not light in the human visual spectrum. In this way, the light transmissivity of the window may be invisible to the human eye.

The biometric monitoring device may employ light pipes or other light-transmissive structures to facilitate transmission of light from the light sources to the user's body and skin. (See, for example, FIGS. 11A through 12). In this regard, in some embodiments, light may be directed from the light source to the skin of the user through such light pipes or other light-transmissive structures. Scattered light from the user's body may be directed back to the optical circuitry in the biometric monitoring device through the same or similar structures. Indeed, the light-transmissive structures may employ a material and/or optical design to facilitate low light loss (for example, the light-transmissive structures may include a lens to facilitate light collection, and portions of the light-transmissive structures may be coated with or adjacent to reflective materials to promote internal reflection of light within the light-transmissive structures) thereby improving the signal-to-noise-ratio of the photo detector and/or facilitating reduced power consumption of the light source(s) and/or light detectors. In some embodiments, the light pipes or other light-transmissive structures may include a material that selectively transmits light having one or more specific or predetermined wavelengths with higher efficiency than others, thereby acting as a bandpass filter. Such a bandpass filter may be tuned to improve the signal of a specific physiological data type. For example, in one embodiment, an In-Mold-Labeling or "IML" light-transmissive structure may be implemented wherein the light-transmissive structure uses a material with predetermined or desired optical characteristics to create a specific bandpass characteristic, for example, so as to pass infrared light with greater efficiency than light of other wavelengths (for example, light having a wavelength in human visible spectrum). In another embodiment, a biometric monitoring device may employ a light-transmissive structure having an optically opaque portion (including certain optical properties) and an optically-transparent portion (including optical properties different from the optically-opaque portion). Such a light-transmissive structure may be provided via a double-shot or two-step molding process wherein optically opaque material and optically transparent material are separately injected into a mold. A biometric monitoring device implementing such a light-transmissive structure may include different light transmissivity properties for different wavelengths depending on the direction of light travel through the light-transmissive structure. For example, in one embodiment, the optically-opaque material may be reflective to a specific wavelength range so as to more efficiently transport light from the user's body back to the light detector (which may be of a different wavelength(s) relative to the wavelength(s) of the emitted light).

In another embodiment, reflective structures may be placed in the field of view of the light emitter(s) and/or light detector(s). For example, the sides of holes that channel light from light emitter(s) to a user's skin and/or from the user's skin to light detector(s) (or through which light-transmissive structures that perform such channeling travel) may be covered in a reflective material (e.g., chromed) to facilitate light transmission. The reflective material may increase the efficiency with which the light is transported to the skin from the light source(s) and then from the skin back into the detector(s). The reflectively-coated hole may be filled in with an optical epoxy or other transparent material to prevent liquid from entering the device body while still allowing light to be transmitted with low transmission loss.

In another embodiment that implements light-transmissive structures (for example, structures created or formed through IML), such light-transmissive structures may include a mask consisting of an opaque material that limits the aperture of one, some, or all of the light source(s) and/or detector(s). In this way, the light-transmissive structures may selectively "define" a preferential volume of the user's body that light is emitted into and/or detected from. Notably, other mask configurations may be employed or implemented in connection with the concepts described and/or illustrated herein; all such masking configurations to, for example, improve the photoplethysmography signal and which are implemented in connection with the concepts described and/or illustrated herein are intended to fall within the scope of the present disclosure.

In another embodiment, the light emitter(s) and/or detector(s) may be configured to transmit light through a hole or series of holes in the device exterior. This hole or series of holes may be filled in with light-transmissive epoxy (e.g. optical epoxy). The epoxy may form a light pipe that allows light to be transmitted from the light emitter(s) to the skin and from the skin back into the light detector(s). This technique also has the advantage that the epoxy may form a watertight seal, preventing water, sweat or other liquid from entering the device body though the hole(s) on the device exterior that allow the light emitter(s) and detector(s) to transmit to, and receive light from, the biometric monitoring device body exterior. An epoxy with a high thermal conductivity may be used to help prevent the light source(s) (e.g., LED's) from overheating.

In any of the light-transmissive structures described herein, the exposed surfaces of the optics (light-transmissive structures) or device body may include a hard coat paint, hard coat dip, or optical coatings (such as anti-reflection, scratch resistance, anti-fog, and/or wavelength band block (such as ultraviolet light blocking) coatings). Such characteristics or materials may improve the operation, accuracy and/or longevity of the biometric monitoring device.

Figure 11A:
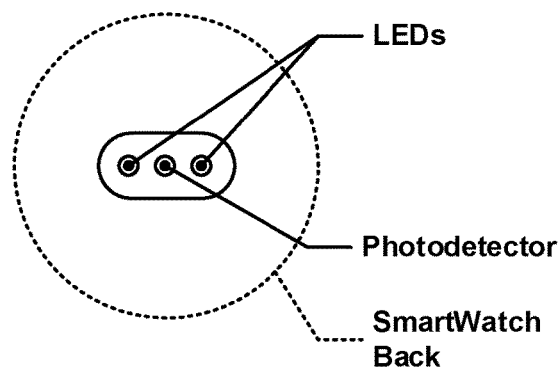
FIG. 11A illustrates an example of one potential PPG light source and photodetector geometry.

FIG. 11A illustrates an example of one potential PPG light source and photodetector geometry. In this embodiment, two light sources are placed on either side of a photodetector. These three devices are located in a protrusion on the back of a wristband-type biometric monitoring device (the side which faces the skin of the user).

Figure 11B:
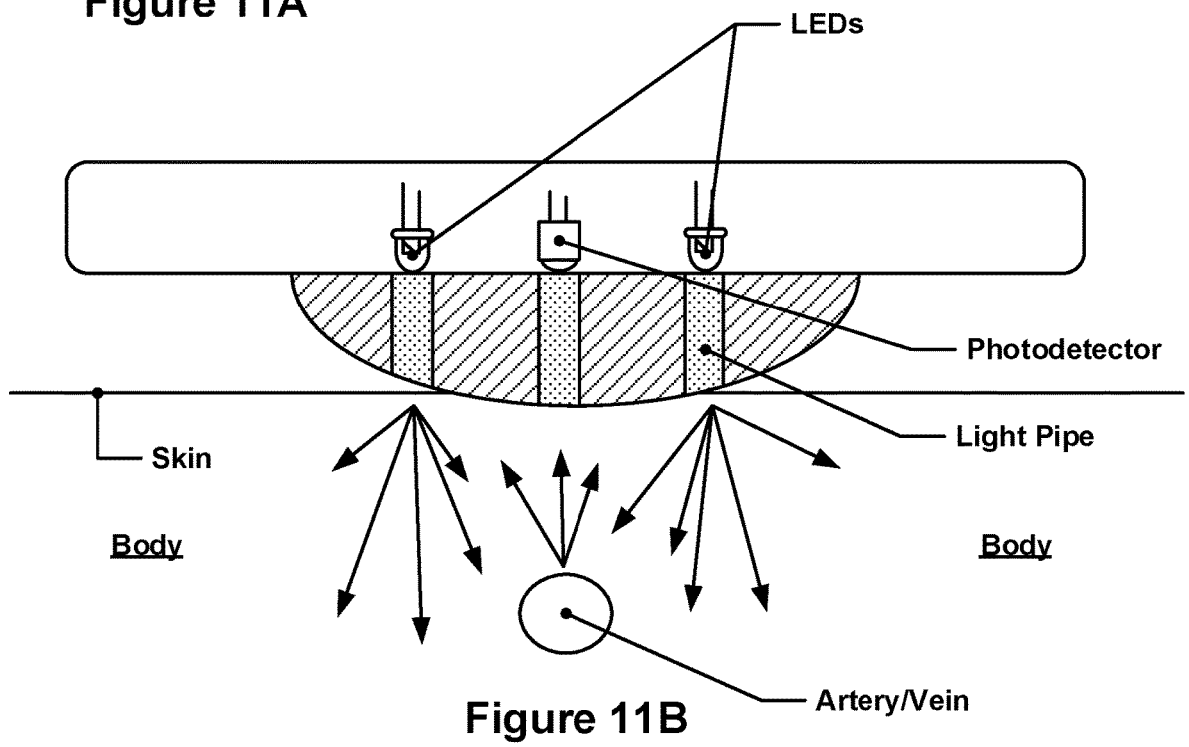
FIGS. 11B and 11C illustrate examples of a PPG sensor having a photodetector and two LED light sources.
Figure 11C:
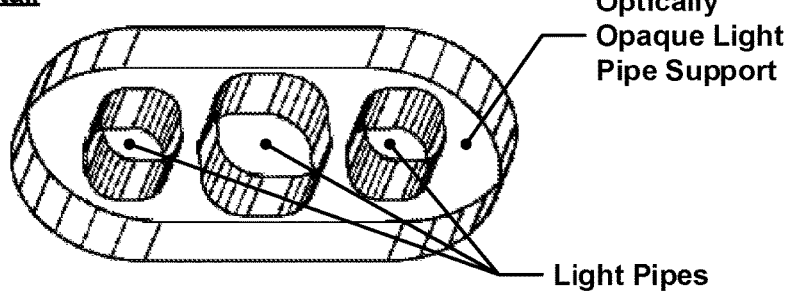

FIGS. 11B and 11C illustrate examples of a PPG sensor having a photodetector and two LED light sources. These components are placed in a biometric monitoring device that has a protrusion on the back side. Light pipes optically connect the LEDs and photodetector with the surface of the user's skin. Beneath the skin, the light from the light sources scatters off of blood in the body, some of which may be scattered or reflected back into the photodetector.

Figure 12:
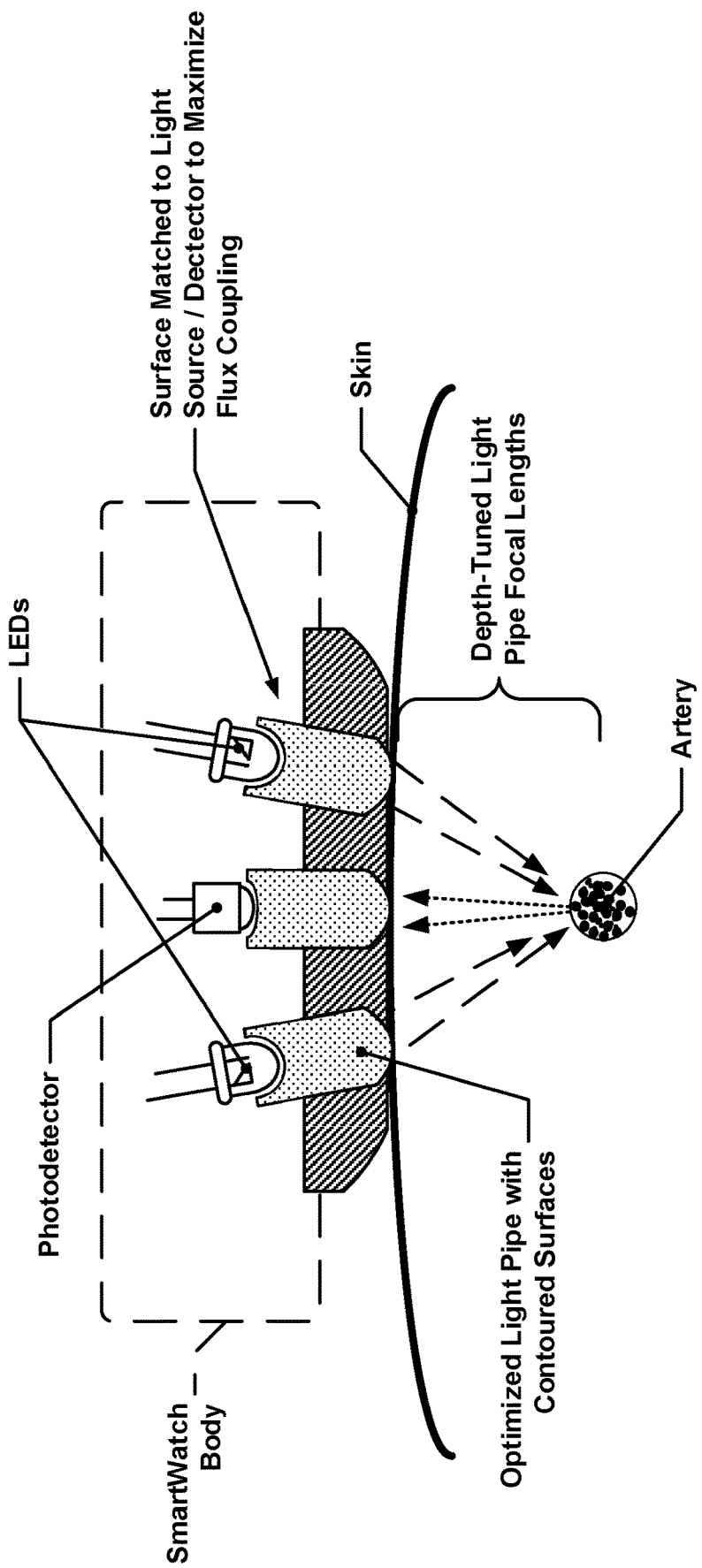
FIG. 12 Illustrates an example of an optimized PPG detector that has a protrusion with curved sides so as not to discomfort the user.

FIG. 12 Illustrates an example of a biometric monitoring device with an optimized PPG detector that has a protrusion with curved sides so as not to discomfort the user. Additionally, the surface of light pipes that optically couple the photodetector and the LEDs to the wearer's skin are contoured to maximize light flux coupling between the LEDs and photodetectors and the light pipes. The ends of the light pipes that face the user's skin are also contoured. This contour may focus or defocus light to optimize the PPG signal. For example, the contour may focus emitted light to a certain depth and location that coincides with an area where blood flow is likely to occur. The vertex of these foci may overlap or be very close together so that the photodetector receives the maximum possible amount of scattered light.

In some embodiments, the biometric monitoring device may include a concave or convex shape, e.g., a lens, on the skin-side of the device, to focus light towards a specific volume at a specific depth in the skin and increase the efficiency of light collected from that point into the photodetector. (See, for example, FIGS. 11A through 12). Where such a biometric monitoring device also employs light pipes to selectively and controllably route light, it may be advantageous to shape the end of the light pipe with a degree of cylindricity, e.g., the end of the light pipe may be a be a cylindrical surface (or portion thereof) defined by a cylinder axis that is nominally parallel to the skin-side (for example, rather than use an axially-symmetric lens). For example, in a wristband-style biometric monitoring device, such a cylindrical lens may be oriented such that the cylinder axis is nominally parallel to the wearer's forearm, which may have the effect of limiting the amount of light that enters such a lens from directions parallel to the person's forearm and increasing the amount of light that enters such a lens from directions perpendicular to the person's forearm—since ambient light is more likely to reach the sensor detection area from directions that are not occluded by the straps of the biometric monitoring device, i.e., along the user's forearm axis, than from directions that are occluded by the straps, i.e., perpendicular to the user's forearm. Such a configuration may improve the signal-to-noise-ratio by increasing the efficiency of light transferred from the emitter onto or into the skin of the user while decreasing "stray" light from being detected or collected by the photodetector. In this way, the signal sampled, measured and/or detected by the photodetector consists less of stray light and more of the user's skin/body response to such emitted light (signal or data that is representative of the response to the emitted light).

In another embodiment, light-transmissive epoxy may be molded into a concave or convex shape so as to provide beneficial optical properties to sensors as well. For example, during the application of light transmissive epoxy, the top of the light-transmissive structure that is formed by the epoxy may be shaped into a concave surface so that light couples more effectively into the light-transmissive structure.

In one embodiment, the components of the optical sensor may be positioned on the skin-side of the device and arranged or positioned to reduce or minimize the distance between (i) the light source(s) and/or the associated detector (s) and (ii) the skin of the user. See, for example, FIG. 10A, which provides a cross-sectional view of a sensor protrusion of an example portable monitoring device. In FIG. 10A, two light sources (e.g., LEDs) are placed on either side of a photodetector to enable PPG sensing. A light-blocking material is placed between the light sources and the photodetector to prevent any light from the light sources from reaching photodetector without first exiting the body of the biometric monitoring device. A flexible transparent layer may be placed on the lower surface of the sensor protrusion to form a seal. This transparent layer may serve other functions such as preventing liquid from entering the device where the light sources or photodetectors are placed. This transparent layer may be formed through in-mold labeling or "IML". The light sources and photodetector may be placed on a flexible PCB.

Such a configuration may improve the efficiency of light flux coupling between the components of the optical sensor and the user's body. For example, in one embodiment, the light source(s) and/or associated detector(s) may be disposed on a flexible or pliable substrate that may flex, allowing the skin-side of the biometric monitoring device, which may be made from a compliant material, to conform (for example, without additional processing) or be capable of being shaped (or compliant) to conform to the shape of the body part (for example, the user's wrist, arm, ankle, and/or leg) to which the biometric monitoring device is coupled to or attached during normal operation so that the light source(s) and/or associated detector(s) are/is close to the skin of the user (i.e., with little to no gap between the skin-side of the device and the adjacent surface of the skin of the user. Sec, for example, FIG. 13A. In one embodiment, the light source(s) and/or associated detector(s) may be disposed on a Flat Flex Cable or "FFC" or flexible PCB. In this embodiment, the flexible or pliable substrate (for example, an FFC or flexible PCB) may connect to a second substrate (for example, PCB) within the device having other components disposed thereon (for example, the data processing circuitry). Optical components of differing heights may be mounted to different "fingers" of flexible substrate and pressed or secured to the housing surface such that the optical components are flush to the housing surface. In one embodiment, the second substrate may be a relatively inflexible or non-pliable substrate, fixed within the device, having other circuitry and components (passive and/or active) disposed thereon.

FIG. 10B depicts a cross-sectional view of a sensor protrusion of an example portable monitoring device; this protrusion is similar to that presented in FIG. 10A with the exception that the light sources and photodetector are placed on a flat and/or rigid PCB.

Figure 10C:
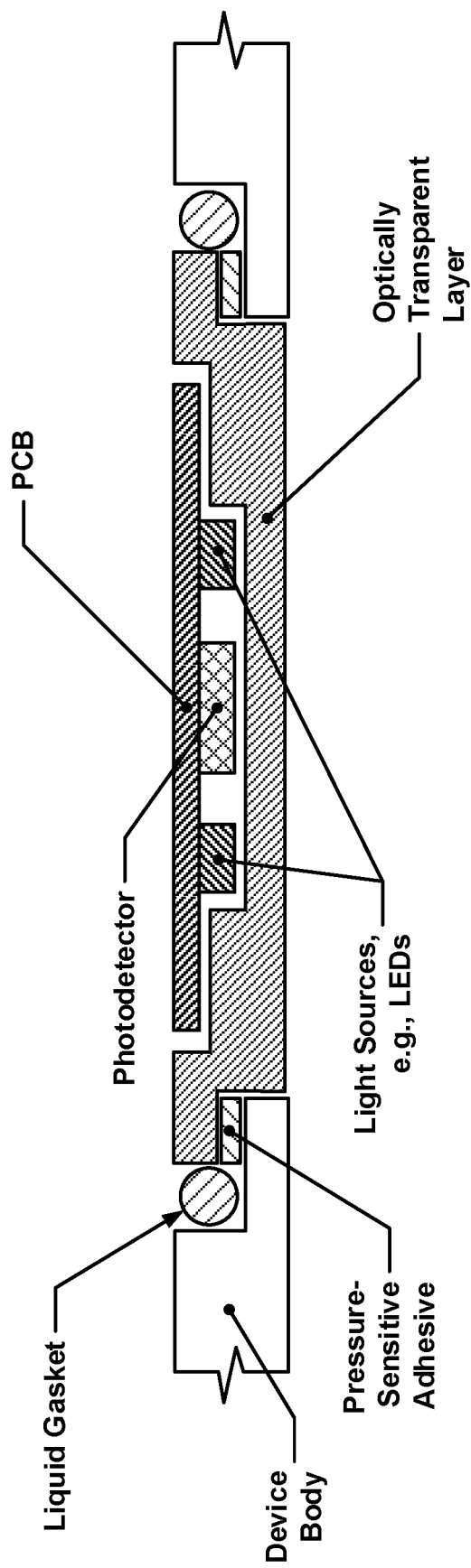
FIG. 10C provides another cross-sectional view of an example PPG sensor implementation.

FIG. 10C provides another cross-sectional view of an example PPG sensor implementation. Of note in this PPG sensor is the lack of a protrusion. Additionally, a liquid gasket and/or a pressure sensitive adhesive are used to prevent liquid from entering the biometric monitoring device body.

Some embodiments of biometric monitoring devices may be adapted to be worn or carried on the body of a user. In some embodiments including the optical pulse waveform monitor or heart rate monitor, the device may be a wrist-worn or arm-mounted accessory such as a watch or bracelet. (See, for example, FIGS. 9A through 14). In one embodiment, optical elements of the optical pulse waveform monitor or heart rate monitor may be located on the interior or skin-side of the biometric monitoring device, for example, facing the top of the wrist (i.e., the optical pulse waveform monitor or heart rate monitor may be adjacent to and facing the wrist) when the biometric monitoring device is worn on the wrist. (See, for example, FIGS. 9A through 10C).

In another embodiment, the optical pulse waveform monitor or heart rate monitor may be located on one or more external or environmental side surfaces of the biometric monitoring device. (See, for example, FIGS. 13B and 14). In such embodiments, the user may touch an optical window (behind which optical elements of the optical pulse waveform monitor or heart rate monitor are located) with a finger on the opposing hand to initiate a pulse waveform measurement or heart rate measurement (and/or other metrics related to heart rate such as heart rate variability) and/or collect data which may be used to determine the user's heart rate (and/or other metrics related to heart rate). (See, for example, FIG. 13B). In one embodiment, the biometric monitoring device may trigger or initiate the measurement(s) by detecting a (sudden) drop in incident light on the photodiode—for example, when the user's finger is placed over the optical window. In addition thereto, or in lieu thereof, a pulse waveform measurement or heart rate measurement (or other such metric) may be trigged by an IR-based proximity detector and/or capacitive touch/proximity detector (which may be separate from other detectors). Such IR-based proximity detector and/or capacitive touch/proximity detector may be disposed in or on and/or functionally, electrically and/or physically coupled to the optical window to detect or determine the presence of, for example, the user's finger.

In yet another embodiment, the biometric monitoring device may include a button that, when depressed, triggers or initiates pulse waveform measurement or heart rate measurement (and/or other metrics related to heart rate). The button may be disposed in close proximity to the optical window to facilitate the user pressing the button while the finger is disposed on the optical window. (See, for example, FIG. 14). In one embodiment, the optical window may be embedded in a push button. Thus, when the user presses the button, it may trigger a measurement of the finger that depresses the button. Indeed, the button may be given a shape and/or resistance to pressing that enhances or optimizes a pressure profile of the button against the finger to provide a high signal-to-noise-ratio during measurement or data acquisition. In other embodiments (not illustrated), the biometric monitoring device may take the form of a clip, a smooth object, a pendant, an anklet, a belt, etc. that is adapted to be worn on the body, clipped or mounted to an article of clothing, deposited in clothing (e.g., in a pocket), or deposited in an accessory (e.g., handbag).

In one specific embodiment, the biometric monitoring device may include a protrusion on the skin- or interior side of the device. (See, FIGS. 9A through 13A). When coupled to the user, the protrusion may engage the skin with more force than the surrounding device body. In this embodiment, an optical window or light transmissive structure (both of which are discussed in detail above) may form or be incorporated in a portion of the protrusion. The light emitter(s) and/or detector(s) of the optical sensor may be disposed or arranged in the protrusion near the window or light transmissive structure. (See, for example, FIGS. 9B and 13A). As such, when attached to the user's body, the window portion of the protrusion of the biometric monitoring device may engage the user's skin with more force than the surrounding device body—thereby providing a more secure physical coupling between the user's skin and the optical window. That is, the protrusion may cause sustained contact between the biometric monitoring device and the user's skin that may reduce the amount of stray light measured by the photodetector, decrease relative motion between the biometric monitoring device and the user, and/or provide improved local pressure to the user's skin; all of which may increase the quality of the cardiac signal of interest. Notably, the protrusion may contain other sensors that benefit from close proximity and/or secure contact to the user's skin. These may be included in addition to or in lieu of a pulse waveform sensor and include sensors such as a skin temperature sensor (e.g., noncontact thermopile that utilizes the optical window or thermistor joined with thermal epoxy to the outer surface of the protrusion), pulse oximeter, blood pressure sensor, EMG, or galvanic skin response (GSR) sensor.

In addition thereto, or in lieu thereof, a portion of the skin-side of the biometric monitoring device may include a friction enhancing mechanism or material. For example, the skin-side of the biometric monitoring device may include a plurality of raised or depressed regions or portions (for example, small bumps, ridges, grooves, and/or divots). Moreover, a friction enhancing material (for example, a gel-like material such as silicone or other elastomeric material) may be disposed on the skin-side. Indeed, a device back made out of gel may also provide friction while also improving user comfort and preventing stray light from entering. As noted above, a friction-enhancing mechanism or material may be used alone or in conjunction with the biometric monitoring device having a protrusion as described herein. In this regard, the biometric monitoring device may include a plurality of raised or depressed regions portions (for example, small bumps, ridges, grooves, and/or divots) in or on the protrusion portion of the device. Indeed, such raised or depressed regions portions may be incorporated/embedded into or on a window portion of the protrusion. In addition thereto, or in lieu thereof, the protrusion portion may consist of or be coated with a friction enhancing material (for example, a gel-like material such as silicone). Notably, the use of a protrusion and/or friction may improve measurement accuracy of data acquisition corresponding to certain parameters (e.g., heart rate, heart rate variability, galvanic skin response, skin temperature, skin coloration, heat flux, blood pressure, blood glucose, etc.) by reducing motion of the biometric monitoring device (and thus of the sensor) relative to the user's skin during operation, especially while the user is in motion.

Some or all of the interior or skin-side housing of the biometric monitoring device may also consist of a metal material (for example, steel, stainless steel, aluminum, magnesium, or titanium). Such a configuration may provide a structural rigidity. (See, for example, FIG. 9B). In such an embodiment, the device body may be designed to be hypoallergenic through the use of a hypoallergenic "nickel-free" stainless steel. Notably, it may be advantageous to employ (at least in certain locations) a type of metal that is at least somewhat ferrous (for example, a grade of stainless steel that is ferrous). In such embodiments, the biometric monitoring device (where it includes a rechargeable energy source (for example, rechargeable battery)) may interconnect with a charger via a connector that secures itself to the biometric monitoring device using magnets that couple to the ferrous material. In addition, biometric monitoring device may also engage a dock or dock station, using such magnetic properties, to facilitate data transfer. Moreover, such a housing may provide enhanced electromagnetic shielding that would enhance the integrity and reliability of the optical pulse waveform sensor and the pulse waveform data acquisition process/operation. Furthermore, a skin temperature sensor may be physically and thermally coupled, for example, with thermal epoxy, to the metal body to sense the temperature of the user. In embodiments including a protrusion, the sensor may be positioned near or in the protrusion to provide secure contact and localized thermal coupling to the user's skin.

In a preferred embodiment, one or more components of the optical sensor (which may, in one embodiment, be located in a protrusion, and/or in another embodiment, may be disposed or placed flush to the surface of the biometric monitoring device) are attached, fixed, included, and/or secured to the biometric monitoring device via a liquid-tight seal (i.e., a method/mechanism that prevents liquid ingress into the body of the biometric monitoring device). For example, in one embodiment, a device back made out of a metal such as, but not limited to, stainless steel, aluminum, magnesium, or titanium, or from a rigid plastic may provide a structure that is stiff enough to maintain the structural integrity of the device while accommodating a watertight seal for the sensor package. (See, for example, FIGS. 9B through 10C).

In a preferred embodiment, a package or module of the optical sensor may be connected to the device with a pressure-sensitive adhesive and a liquid gasket. See, for example, FIG. 10C, which provides another cross-sectional view of a PPG sensor implementation. Of note in this PPG sensor is the lack of a protrusion. Additionally, a liquid gasket and/or a pressure sensitive adhesive are used to prevent liquid from entering the device body. Screws, rivets or the like may also be used, for example, if a stronger or more durable connection is required between the optical sensor package/module and the device body. Notably, the present embodiments may also use watertight glues, hydrophobic membranes such as Gore-Tex, o-rings, sealant, grease, or epoxy to secure or attach the optical sensor package/module to the biometric monitoring device body.

As discussed above, the biometric monitoring device may include a material disposed on the skin- or interior side that includes high reflectivity characteristics—for example, polished stainless steel, reflective paint, and polished plastic. In this way, light scattered off the skin-side of the device may be reflected back into the skin in order to, for example, improve the signal-to-noise-ratio of an optical pulse waveform sensor. Indeed, this effectively increases the input light signal as compared with a device body back that is non-reflective (or less reflective). Notably, in one embodiment, the color of the skin or interior side of the biometric monitoring device may be selected to provide certain optical characteristics (for example, reflect certain or predetermined wavelengths of light), in order to improve the signal with respect to certain physiological data types. For example, where the skin- or interior side of the biometric monitoring is green, the measurements of the heart rate may be enhanced due to the preferential emission of a wavelength of the light corresponding to the green spectrum. Where the skin- or interior side of the biometric monitoring is red, the measurements of the $SpO_2$ may be enhanced due to the emission preferential of a wavelength of the light corresponding to the red spectrum. In one embodiment, the color of the skin- or interior side of the biometric monitoring may be modified, adjusted and/or controlled in accordance with a predetermined type of physiological data being acquired.

Figure 18A:
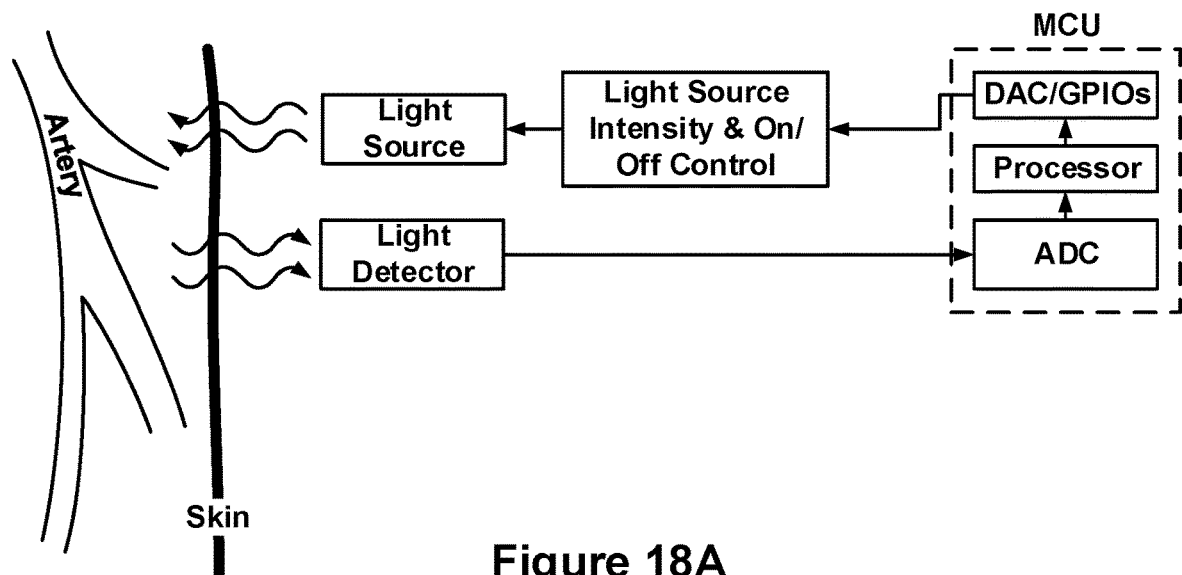
FIG. 18A illustrates an example block diagram of a PPG sensor which has a light source, light detector, ADC, processor, DAC/GPIOs, and light source intensity and on/off control.

FIG. 18A depicts an example schematic block diagram of an optical pulse waveform sensor where light is emitted from a light source toward the user's skin and the reflection of such light from the skin/internal body of the user is sensed by a light detector, the signal from which is subsequently digitized by an analog to digital converter (ADC). The intensity of the light source may be modified (e.g., through a light source intensity control module) to maintain a desirable reflected signal intensity. For example, the light source intensity may be reduced to avoid saturation of the output signal from the light detector. As another example, the light source intensity may be increased to maintain the output signal from the light detector within a desired range of output values. Notably, active control of the system may be achieved through linear or nonlinear control methods such as proportional-integral-derivative (PID) control, fixed step control, predictive control, neural networks, hysteresis, and the like, and may also employ information derived from other sensors in the device such as motion, galvanic skin response, etc. FIG. 18A is provided for illustration and does not limit the implementation of such a system to, for instance, an ADC integrated within a MCU, or the use of a MCU for that matter. Other possible implementations include the use of one or more internal or external ADCs, FPGAs, ASICs, etc.

Figure 18B:
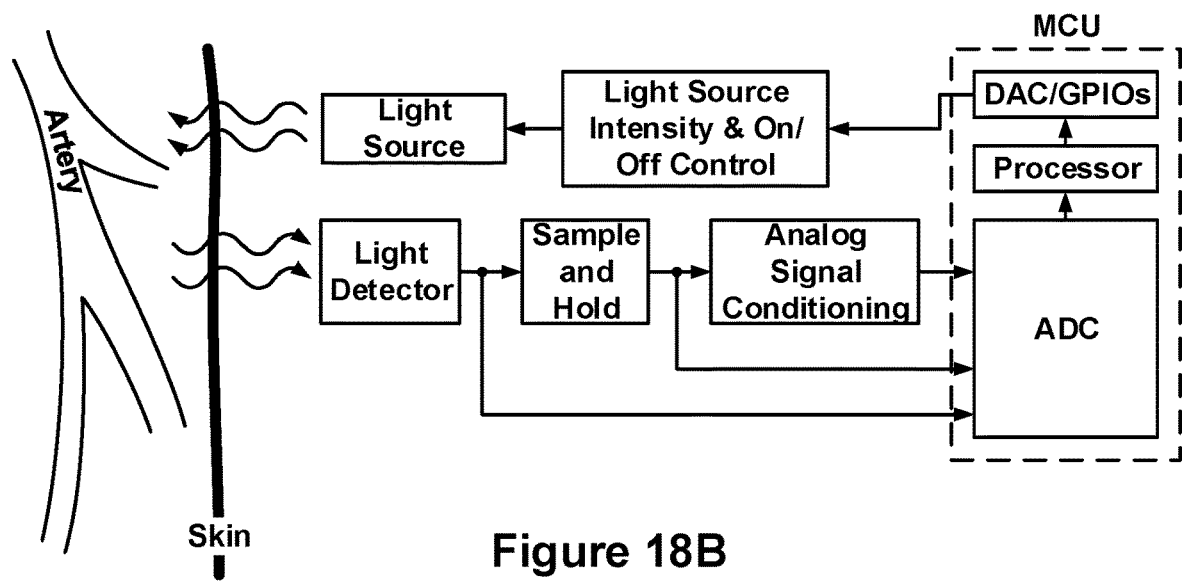
FIG. 18B illustrates an example block diagram of a PPG sensor that is similar to that of FIG. 18A which additionally uses a sample-and-hold circuit as well as analog signal conditioning.

In another embodiment, system with an optical pulse waveform sensor may incorporate the use of a sample-and-hold circuit (or equivalent) to maintain the output of the light detector while the light source is turned off or attenuated to save power. In embodiments where relative changes in the light detector output are of primary importance (e.g., pulse waveform measurement or heart rate measurement), the sample-and-hold circuit may not have to maintain an accurate copy of the output of the light detector. In such cases, the sample-and-hold may be reduced to, for example, a diode (e.g., Schottky diode) and capacitor. The output of the sample-and-hold circuit may be presented to an analog signal conditioning circuit (e.g., a Sallen-Key bandpass filter, level shifter, and/or gain circuit) to condition and amplify the signal within frequency bands of interest (e.g., 0.1 Hz to 10 Hz for cardiac or respiratory function), which may then be digitized by the ADC. See, for example, FIG. 18B.

Figure 18C:
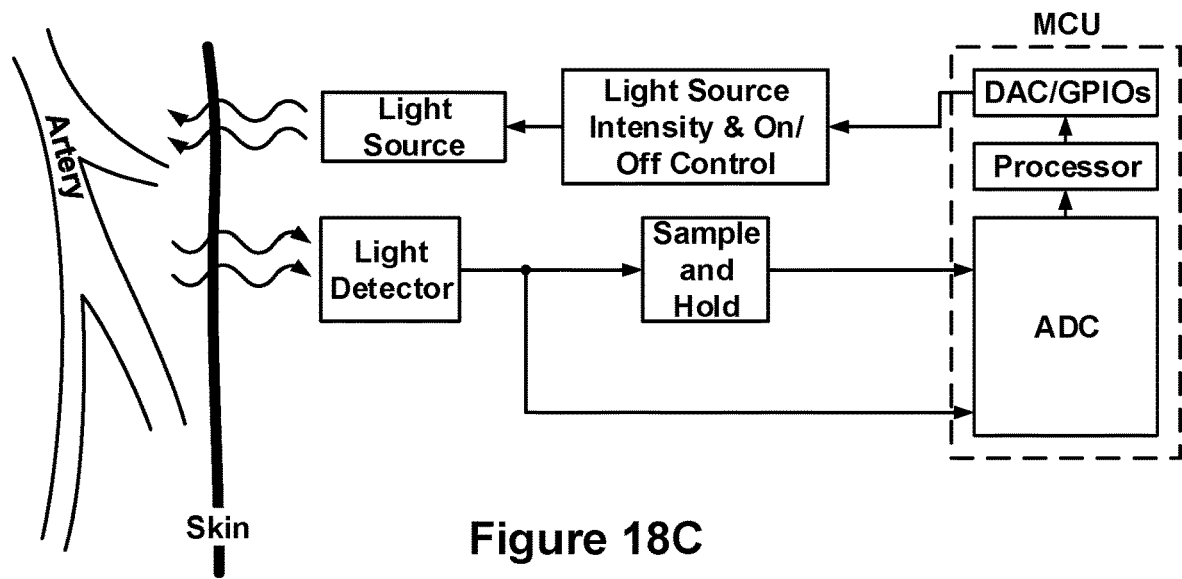
FIG. 18C illustrates an example block diagram of a PPG sensor that is similar to that of FIG. 18A which additionally uses a sample-and-hold circuit.
Figure 18D:
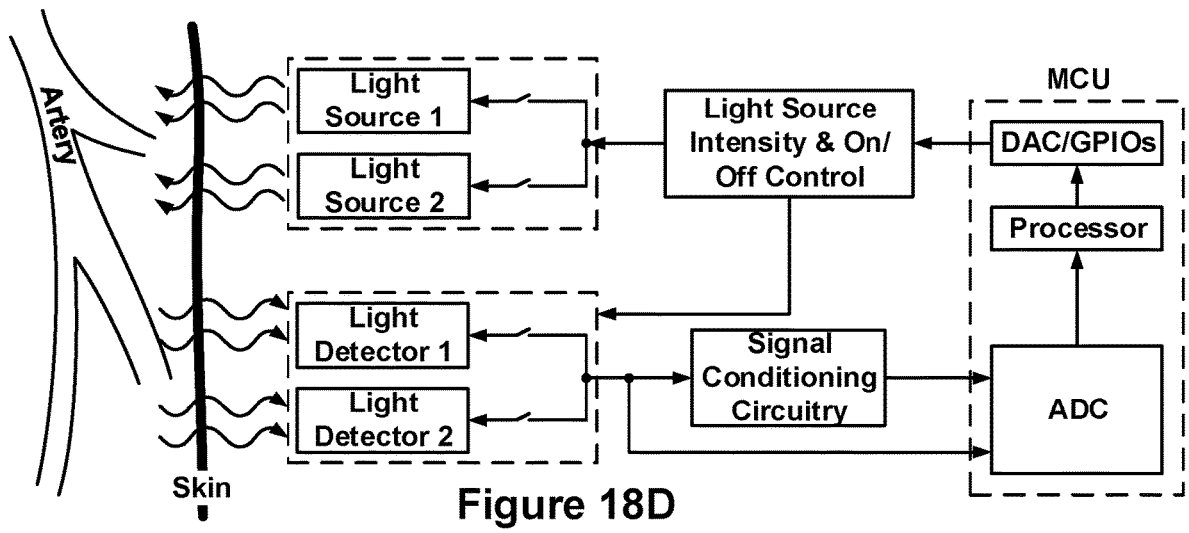
FIG. 18D illustrates an example block diagram of a a PPG sensor having multiple switchable light sources and detectors, light source intensity/on and off control, and signal conditioning circuitry.
Figure 18E:
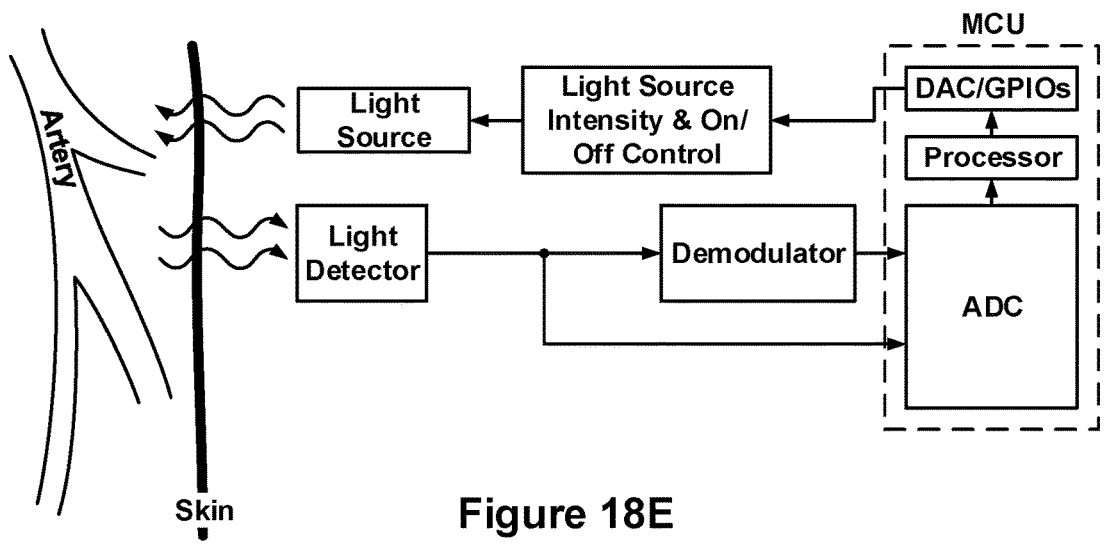
FIG. 18E illustrates an example block diagram of a PPG sensor which uses synchronous detection. To perform this type of PPG detection, it has a demodulator.

In operation, circuit topologies such as those already described herein (e.g. a sample-and-hold circuit) remove the DC and low frequency components of the signal and help resolve the AC component related to heart rate and/or respiration. The embodiment may also include the analog signal conditioning circuitry for variable gain settings that can be controlled to provide a suitable signal (e.g., not saturated). The performance characteristics (e.g., slew rate and/or gain bandwidth product) and power consumption of the light source, light detector, and/or sample-and-hold may be significantly higher than the analog signal conditioning circuit to enable fast duty cycling of the light source. In some embodiments, the power provided to the light source and light detector may be controlled separately from the power provided to the analog signal conditioning circuit to provide additional power savings. Alternatively or additionally, the circuitry can use functionality such as an enable, disable and/or shutdown to achieve power savings. In another embodiment, the output of the light detector and/or sample-and-hold circuit may be sampled by an ADC in addition to or in lieu of the analog signal conditioning circuit to control the light intensity of the light source or to measure the physiologic parameters of interest when, for example, the analog signal conditioning circuit is not yet stable after a change to the light intensity setting. Notably, because the physiologic signal of interest is typically small relative to the inherent resolution of the ADC, in some embodiments, the reference voltages and/or gain of the ADC may be adjusted to enhance signal quality and/or the ADC may be oversampled. In yet another embodiment, the device may digitize the output of only the sample-and-hold circuit by, for example, oversampling, adjusting the reference voltages and/or gain of the ADC, or using a high resolution ADC. See, for example, FIG. 18C.

PPG DC Offset Removal Techniques

Figure 18F:
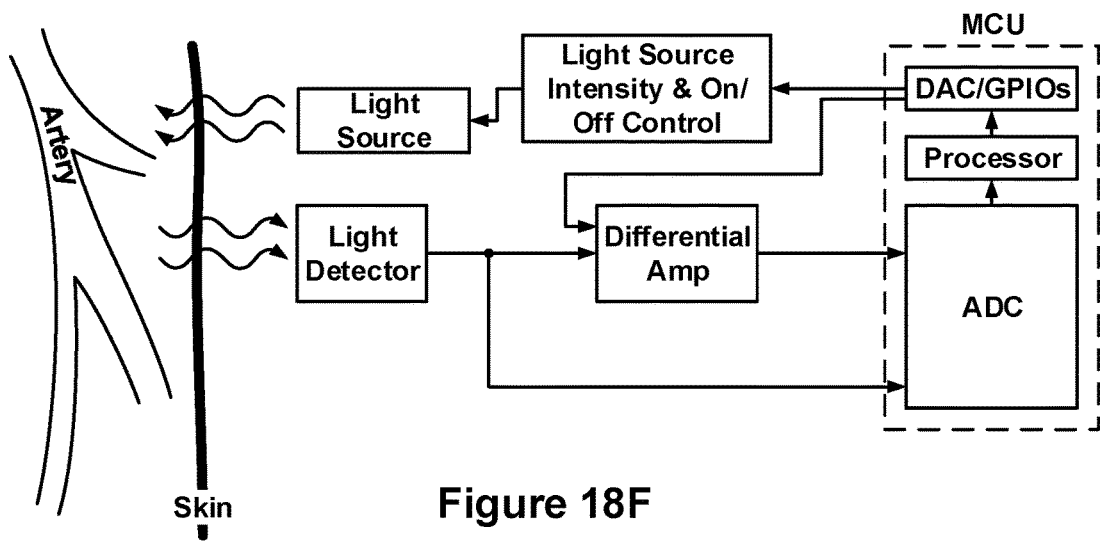
FIG. 18F illustrates an example block diagram of a PPG sensor which, in addition to the features of the sensor illustrated in FIG. 18A, has a differential amplifier.

In another embodiment, the sensor device may incorporate a differential amplifier to amplify the relative changes in the output of the light detector. See, for example, FIG. 18F. In some embodiments, a digital average or digital low-pass filtered signal may be subtracted from the output of the light detector. This modified signal may then be amplified before it is digitized by the ADC. In another embodiment, an analog average or analog low-pass filtered signal may be subtracted from the output of the light detector through, for example, the use of a sample-and-hold circuit and analog signal conditioning circuitry. The power provided to the light source, light detector, and differential amplifier may be controlled separately from the power provided to the analog signal conditioning circuit to improve power savings.

In another embodiment, a signal (voltage or current, depending on the specific sensor implementation) may be subtracted from the raw PPG signal to remove any bias in the raw PPG signal and therefore increase the gain or amplification of the PPG signal that contains heart rate (or other circulatory parameters such as heart rate variability) information. This signal may be set to a default value in the factory, to a value based on the user's specific skin reflectivity, absorption, and/or color, and/or may change depending on feedback from an ambient light sensor, or depending on analytics of the PPG signal itself. For example, if the PPG signal is determined to have a large DC offset, a constant voltage may be subtracted from the PPG signal to remove the DC offset and enable a larger gain, therefore improving the PPG signal quality. The DC offset in this example may result from ambient light (for example from the sun or from indoor lighting) reaching the photodetector from or reflected light from the PPG light source.

In another embodiment, a differential amplifier may be used to measure the difference between current and previous samples rather than the magnitude of each signal. Since the magnitude of each sample is typically much greater than the difference between each sample, a larger gain can be applied to each measurement, therefore improving the PPG signal quality. The signal may then be integrated to obtain the original time domain signal.

In another embodiment, the light detector module may incorporate a transimpedance amplifier stage with variable gain. Such a configuration may avoid or minimize saturation from bright ambient light and/or bright emitted light from the light source. For example, the gain of the transimpedance amplifier may be automatically reduced with a variable resistor and/or multiplexed set of resistors in the negative feedback path of the transimpedance amplifier. In some embodiments, the device may incorporate little to no optical shielding from ambient light by amplitude-modulating the intensity of the light source and then demodulating the output of the light detector (e.g., synchronous detection). See, for instance, FIG. 18E. In other aspects, if the ambient light is of sufficient brightness to obtain a heart rate signal, the light source may be reduced in brightness and/or turned off completely.

Figure 18G:
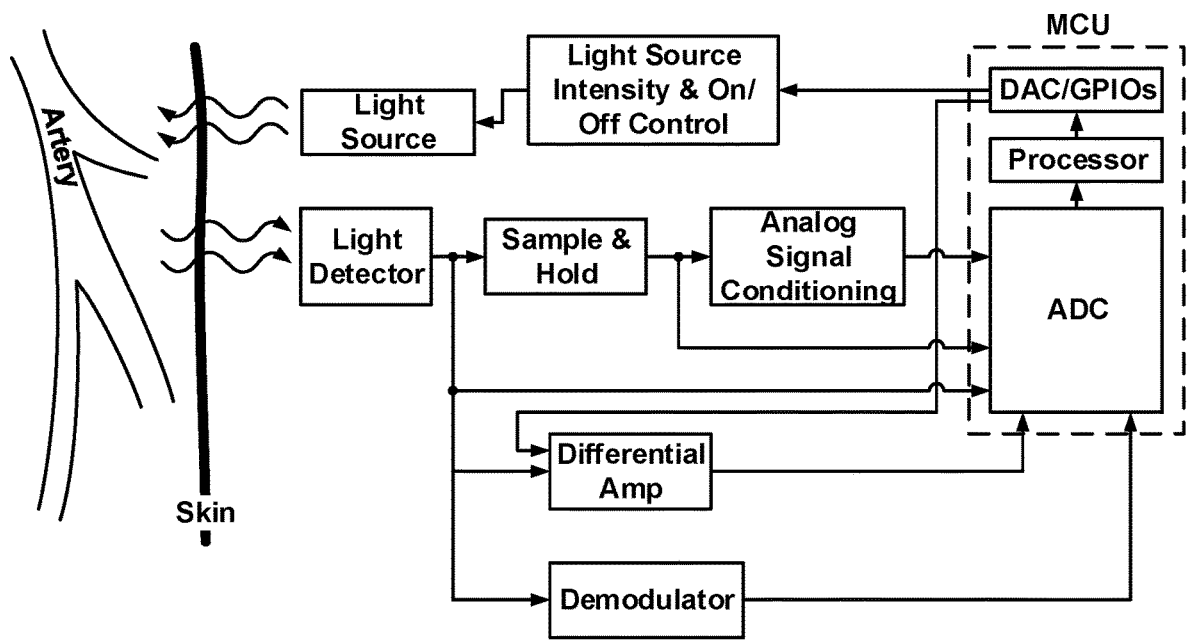
FIG. 18G illustrates an example block diagram of a PPG sensor which has the features of the PPG sensors shown in FIGS. 18A-18F.

In yet another embodiment, the aforementioned processing techniques may be used in combination to optically measure physiological parameters of the user. See, for example, FIG. 18G. This topology may allow the system to operate in a low power measurement state and circuit topology when applicable and adapt to a higher power measurement state and circuit topology as necessary. For instance, the system may measure the physiologic parameter (e.g., heart rate) of interest using analog signal-conditioning circuitry while the user is immobile or sedentary to reduce power consumption, but switch to oversampled sampling of the light detector output directly while the user is active.

In embodiments where the biometric monitoring device includes a pulse waveform monitor or heart rate monitor, processing of the signal to obtain pulse waveform measurement or heart rate measurements may include filtering and/or signal conditioning such as band-pass filtering (e.g., Butterworth filter). To counteract large transients that may occur in the signal and/or to improve convergence of said filtering, nonlinear approaches may be employed such as neural networks or slew rate limiting. Data from the sensors on the device such as motion, galvanic skin response, skin temperature, etc., may be used to adjust the signal conditioning methods employed. Under certain operating conditions, the heart rate of the user may be measured by counting the number of signal peaks within a time window or by utilizing the fundamental frequency or second harmonic of the signal (e.g., through a fast Fourier transform (FFT)). In other cases, such as pulse waveform data acquired while the user is in motion, FFTs may be performed on the signal and spectral peaks extracted, which may then be subsequently processed by a multiple-target tracker which starts, continues, merges, and deletes tracks of the spectra. In some embodiments, a similar set of operations may be performed on the motion signal and the output may be used to do activity discrimination (e.g., sedentary, walking, running, sleeping, lying down, sitting, biking, typing, elliptical, weight training) which is used to assist the multiple-target tracker. For instance, it may be determined that the user was stationary and has begun to move. This information may be used to preferentially bias the track continuation toward increasing frequencies. Similarly, the activity discriminator may determine that the user has stopped running or is running slower and this information may be used to preferentially bias the track continuation toward decreasing frequencies. Tracking may be achieved with single-scan or multi-scan, multiple-target tracker topologies such as joint probabilistic data association trackers, multiple-hypothesis tracking, nearest neighbor, etc. Estimation and prediction in the tracker may be done through Kalman filters, spline regression, particle filters, interacting multiple model filters, etc. A track selector module may use the output tracks from the multiple-spectra tracker and estimate the user's heart rate. The estimate may be taken as the maximum likelihood track, a weight sum of the tracks against their probabilities of being the heart rate, etc. The activity discriminator may furthermore influence the selection and/or fusion to get the heart rate estimate. For instance, if the user is sleeping, sitting, lying down, or sedentary, a prior probability may be skewed toward heart rates in the 40-80 bpm range; whereas if the user is running, jogging, or doing other vigorous exercise, a prior probability may be skewed toward elevated heart rates in the 90-180 bpm range. The influence of the activity discriminator may be based on the speed of the user.

The estimate may be shifted toward (or wholly obtained by) the fundamental frequency of the signal when the user is not moving. The track that corresponds to the user's heart rate may be selected based on criteria that are indicative of changes in activity; for instance, if the user begins to walk from being stationary, the track that illustrates a shift toward higher frequency may be preferentially chosen.

The acquisition of a good heart rate signal may be indicated to the user through a display on the biometric monitoring device or another device in wired or wireless communication with the biometric monitoring device (e.g., a Bluetooth Low Energy-equipped mobile phone). In some embodiments, the biometric monitoring device may include a signal-strength indicator that is represented by the pulsing of an LED viewable by the user. The pulsing may be timed or correlated to be coincident with the user's heartbeat. The intensity, pulsing rate and/or color of the LED may be modified or adjusted to suggest signal strength. For example, a brighter LED intensity may represent a stronger signal or in an RGB LED configuration, a green colored LED may represent a stronger signal.

In some embodiments, the strength of the heart rate signal may be determined by the energy (e.g., squared sum) of the signal in a frequency band of, for instance, 0.5 Hz to 4 Hz. In other embodiments, the biometric monitoring device may have a strain gauge, pressure sensor, force sensor, or other contact-indicating sensor that may be incorporated or constructed into the housing and/or in the band (in those embodiments where the biometric monitoring device is attached to or mounted with a band like a watch, bracelet, and/or armband—which may then be secured to the user). A signal quality metric (e.g. heart rate signal quality) may be calculated based on data from these contact sensors either alone or in combination with data from the heart rate signal.

In another embodiment, the biometric monitoring device may monitor heart rate optically through an array of photodetectors such as a grid of photodiodes or a CCD camera. Motion of the optical device with respect to the skin may be tracked through feature-tracking of the skin and/or adaptive motion correction using an accelerometer and gyroscope. The detector array may be in contact with the skin or offset at a small distance away from the skin. The detector array and its associated optics may be actively controlled (e.g., with a motor) to maintain a stabilized image of the target and acquire a heart rate signal. This optomechanical stabilization may be achieved using information from motion sensors (e.g., a gyroscope) or image features. In one embodiment, the biometric monitoring device may implement relative motion cancellation using a coherent or incoherent light source to illuminate the skin and a photodetector array with each photodetector associated with comparators for comparing the intensity between neighboring detectors—obtaining a so-called speckle pattern which may be tracked using a variety of image tracking techniques such as optical flow, template matching, edge tracking, etc. In this embodiment, the light source used for motion tracking may be different than the light source used in the optical pulse waveform monitor or heart rate monitor.

In another embodiment, the biometric monitoring device may consist of a plurality of photodetectors and photoemitters distributed along a surface of the device that touches the user's skin (i.e., the skin-side of the biometric monitoring device). (See, for example, FIGS. 9A through 13A). In the example of a bracelet, for instance, there may be a plurality of photodetectors and photoemitters placed at various sites along the circumference of the interior of the band. (See, for example, FIG. 13A). A heart rate signal-quality metric associated with each site may be calculated to determine the best or set of best sites for estimating the user's heart rate. Subsequently, some of the sites may be disabled or turned off to, for example, reduce power consumption. The device may periodically check the heart rate signal quality at some or all of the sites to enhance, monitor and/or optimize signal and/or power efficiency.

In another embodiment, a biometric monitoring device may include a pulse waveform monitor or heart rate monitoring system including a plurality of sensors such as optical, acoustic, pressure, electrical (e.g., ECG or EKG), and motion and fuse the information from two or more of these sensors to provide an estimate of heart rate and/or mitigate noise induced from motion.

In addition to pulse waveform monitor or heart rate monitoring (or other biometric monitoring), or in lieu thereof, the biometric monitoring device, in some embodiments, may include optical sensors to track or detect time and duration of ultraviolet light exposure, total outdoor light exposure, the type of light source and duration and intensity of that light source (fluorescent light exposure, incandescent bulb light exposure, halogen, etc.), exposure to television (based on light type and flicker rate), whether the user is indoors or outdoors, time of day and location based on light conditions. In one embodiment, the ultraviolet detection sensor may consist of a reverse biased LED emitter driven as a light detector. The photocurrent produced by this detector may be characterized by, for instance, measuring the time it takes for the LED's capacitance (or alternately a parallel capacitor) to discharge.

All of the optical sensors discussed herein may be used in conjunction with other sensors to improve detection of the data described above or be used to augment detection of other types of physiological or environmental data.

Where the biometric monitoring device includes an audio or passive acoustic sensor, the device may contain one or more passive acoustic sensors that detect sound and pressure and that can include, but are not limited to, microphones, piezo films, etc. The acoustic sensors may be disposed on one or more sides of the device, including the side that touches or faces the skin (skin-side) and the sides that face the environment (environmental sides).

Skin-side acoustic or audio sensors may detect any type of sound transmitted through the body and such sensors may be arranged in an array or pattern that optimizes both the signal-to-noise-ratio and power consumption of such sensors. These sensors may detect respiration (e.g., by listening to the lung), respiratory sounds (e.g., breathing, snoring) and problems (e.g., sleep apnea, etc.), heart rate (listening to the heart beat), user's voice (via sound transmitted from the vocal cords throughout the body).

The biometric monitoring devices of the present disclosure may also include galvanic skin-response (GSR) circuitry to measure the response of the user's skin to emotional and physical stimuli or physiological changes (e.g., the transition of sleep stage). In some embodiments, the biometric monitoring device may be a wrist- or arm-mounted device incorporating a band made of conductive rubber or fabric so that the galvanic skin response electrodes may be hidden in the band. Because the galvanic skin response circuitry may be subjected to changing temperatures and environmental conditions, it may also include circuitry to enable automatic calibration, such as two or more switchable reference resistors in parallel or in series with the human skin/electrode path that allows real-time measurement of known resistors to characterize the response of the galvanic skin response circuit. The reference resistors may be switched into and out of the measurement path such that they are measured independently and/or simultaneously with the resistance of the human skin.

Biometric Feedback

Some embodiments of biometric monitoring devices may provide feedback to the user based on one or more biometric signals. In one embodiment, a PPG signal may be presented to the user as a real-time or near-real-time waveform on a display of the biometric monitoring device (or on a display of a secondary device in communication with the biometric monitoring device). This waveform may provide similar feedback to the waveform displayed on an ECG or EKG machine. In addition to providing the user with an indication of the PPG signal which may be used to estimate various heart metrics (e.g., heart rate), the waveform may also provide feedback that may enable the user to optimize the position and pressure with which they are wearing the biometric monitoring device. For example, the user may see that the waveform has a low amplitude. In response to this, the user may try moving the position of the biometric monitoring device to a different location which gives a higher amplitude signal. In some implementations, the biometric monitoring device may, based on such indications, provide instructions to the user to move or adjust the fit of the biometric monitoring device so as to improve the signal quality.

In another embodiment, feedback about the quality of the PPG signal may be provided to the user through a method other than displaying the waveform. The biometric monitoring device may emit an auditory alarm (e.g. a beep) if the signal quality (e.g. signal to noise ratio) exceeds a certain threshold. The biometric monitoring device may provide a visual cue (through the use of a display for example) to the user to either change the position of the sensor and/or increase the pressure with which the device is being worn (for example by tightening a wrist strap in the case that the device is worn on the wrist).

Biometric feedback may be provided for sensors other than PPG sensors. For example, if the device uses ECG, EMG, or is connected to a device which performs either of these, it may provide feedback to the user regarding the waveform from those sensors. If the signal-to-noise-ratio of these sensors is low, or the signal quality is otherwise compromised, the user may be instructed on how they can improve the signal. For example, if the heart rate cannot be detected from the ECG sensor, the device may provide a visual message to the user instructing them to wet or moisten the ECG electrodes to improve the signal.

Environmental Sensors

Some embodiments of biometric monitoring devices of the present disclosure may use one, some or all of the following environmental sensors to, for example, acquire the environmental data, including environmental data outlined in the table below. Such biometric monitoring devices are not limited to the number or types of sensors specified below but may employ other sensors that acquire environmental data outlined in the table below. All combinations and permutations of environmental sensors and/or environmental data are intended to fall within the scope of the present disclosure. Additionally, the device may derive environmental data from the corresponding sensor output data, but is not limited to the types of environmental data that it could derive from said sensor.

Notably, embodiments of biometric monitoring devices of the present disclosure may use one or more, or all of the environmental sensors described herein and one or more, or all of the physiological sensors described herein. Indeed, biometric monitoring device of the present disclosure may acquire any or all of the environmental data and physiological data described herein using any sensor now known or later developed—all of which are intended to fall within the scope of the present disclosure.

| Environmental Sensors | Environmental data acquired |
| --- | --- |
| Motion Detector<br>Potential Embodiments:<br>Inertial, Gyroscopic or Accelerometer-based Sensors<br>GPS | Location |
| Pressure/Altimeter sensor<br>Ambient Temp<br>Light Sensor | Elevation<br>Temperature<br>Indoor vs outdoor<br>Watching TV (spectrum/flicker rate detection)<br>Optical data transfer-initiation, QR codes, etc.<br>Ultraviolet light exposure |
| Audio | Indoor vs. Outdoor |
| Compass<br>Potential Embodiments:<br>−3 Axis Compass | Location and/or orientation |

Figure 19C:
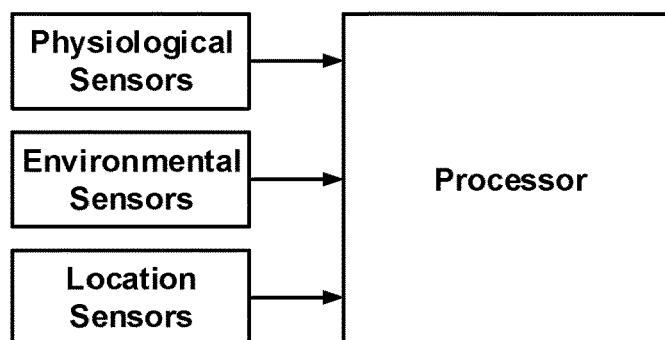
FIG. 19C is a schematic diagram of an example of a portable biometric monitoring device having physiological sensors, environmental sensors, and location sensors connected to a processor.

In one embodiment, the biometric monitoring device may include an altimeter sensor, for example, disposed or located in the interior of the device housing. (See, for example, FIGS. 19B and 19C; FIG. 19C illustrates an example of a portable biometric monitoring device having physiological sensors, environmental sensors, and location sensors connected to a processor). In such a case, the device housing may have a vent that allows the interior of the device to measure, detect, sample and/or experience any changes in exterior pressure. In one embodiment, the vent may prevent water from entering the device while facilitating measuring, detecting and/or sampling changes in pressure via the altimeter sensor. For example, an exterior surface of the biometric monitoring device may include a vent type configuration or architecture (for example, a Gore™ vent) that allows ambient air to move in and out of the housing of the device (which allows the altimeter sensor to measure, detect and/or sample changes in pressure), but reduces, prevents, and/or minimizes water and other liquids from flowing into the housing of the device.

The altimeter sensor, in one embodiment, may be filled with gel that allows the sensor to experience pressure changes outside of the gel. The gel may act as a relatively impervious, incompressible, yet flexible, membrane that transmits external pressure variations to the altimeter while physically separating the altimeter (and other internal components) from the outside environment. The use of a gel-filled altimeter may give the device a higher level of environmental protection with or without the use of an environmentally sealed vent. The device may have a higher survivability rate with a gel-filled altimeter in locations including, but not limited to, locations that have high humidity, clothes washers, dish washers, clothes dryers, a steam room or sauna, a shower, a pool, a bath, and any location where the device may be exposed to moisture, exposed to liquid, or submerged in liquid.

Sensors integration/Signal Processing

Some embodiments of the biometric monitoring devices of the present disclosure may use data from two or more sensors to calculate the corresponding physiological or environmental data as seen in the table below (for example, data from two or more sensors may be used in combination to determine metrics such as those listed below). The biometric monitoring device may include, but is not limited to, the number, types, or combinations of sensors specified below. Additionally, such biometric monitoring devices may derive the included data from the corresponding sensor combinations, but are not limited to the number or types of data that may be calculated from the corresponding sensor combinations.

sensors/circuitries to, for example, determine, correlate, and/or "map" geographical regions according to physiological data (for example, heart rate, stress, activity level, quantity of sleep and/or caloric intake). In this way, the biometric monitoring device may identify geographical regions that increase or decrease a measurable user metric including, but not limited to, heart rate, stress, activity, level, quantity of sleep and/or caloric intake.

| Sensor Integrations | Data derived from signal processing of multiple sensors |
| --- | --- |
| Skin Temp and Ambient Temp | Heat Flux |
| Heart Rate and Motion | Elevation gain |
| Motion detector and other user's motion detector (linked by wireless communication path) | Users in the proximity |
| Motion, any pulse waveform sensor, galvanic skin response | Sit/ Standing detection |
| Any heart rate, heart rate variability sensor, respiration, motion | Sleep Phase detection |
| Any pulse waveform sensor and/or wetness sensor, and/or motion detector | Sleep Apnea detection Resting Heart rate Active Heart Rate Heart rate while asleep Heart rate while sedentary |
| Any heart rate detector | Early detection of heart problems: Cardiac Arrhythmia Cardiac Arrest |
| Multiple heart rate detectors | Pulse transit time |
| Audio and/or strain gauge | Typing detection |
| GPS and photoplethysmography (PPG) | Location-stress correlation: determination of stressful regions determination of low stress regions Activity-specific heart rate resting heart rate active heart rate Automatic activity classification and activity heart rate determination |
| Heart rate, galvanic skin response, accelerometer and respiration | User fatigue, for example while exercising |

In some embodiments, the biometric monitoring device may also include a near-field communication (NFC) receiver/transmitter to detect proximity to another device, such as a mobile phone. When the biometric monitoring device is brought into close or detectable proximity to the second device, it may trigger the start of new functionality on the second device (e.g., the launching of an "app" on the mobile phone and radio syncing of physiological data from the device to the second device). (See, for example, FIG. 17). Indeed, the biometric monitoring device of the present disclosure may implement any of the circuitry and techniques described and/or illustrated in U.S. Provisional Patent Application 61/606,559, filed Mar. 5, 2012, "Near Field Communication System, and Method of Operating Same", inventor: James Park (the contents of which are incorporated herein by reference for such purpose).

Figure 17:
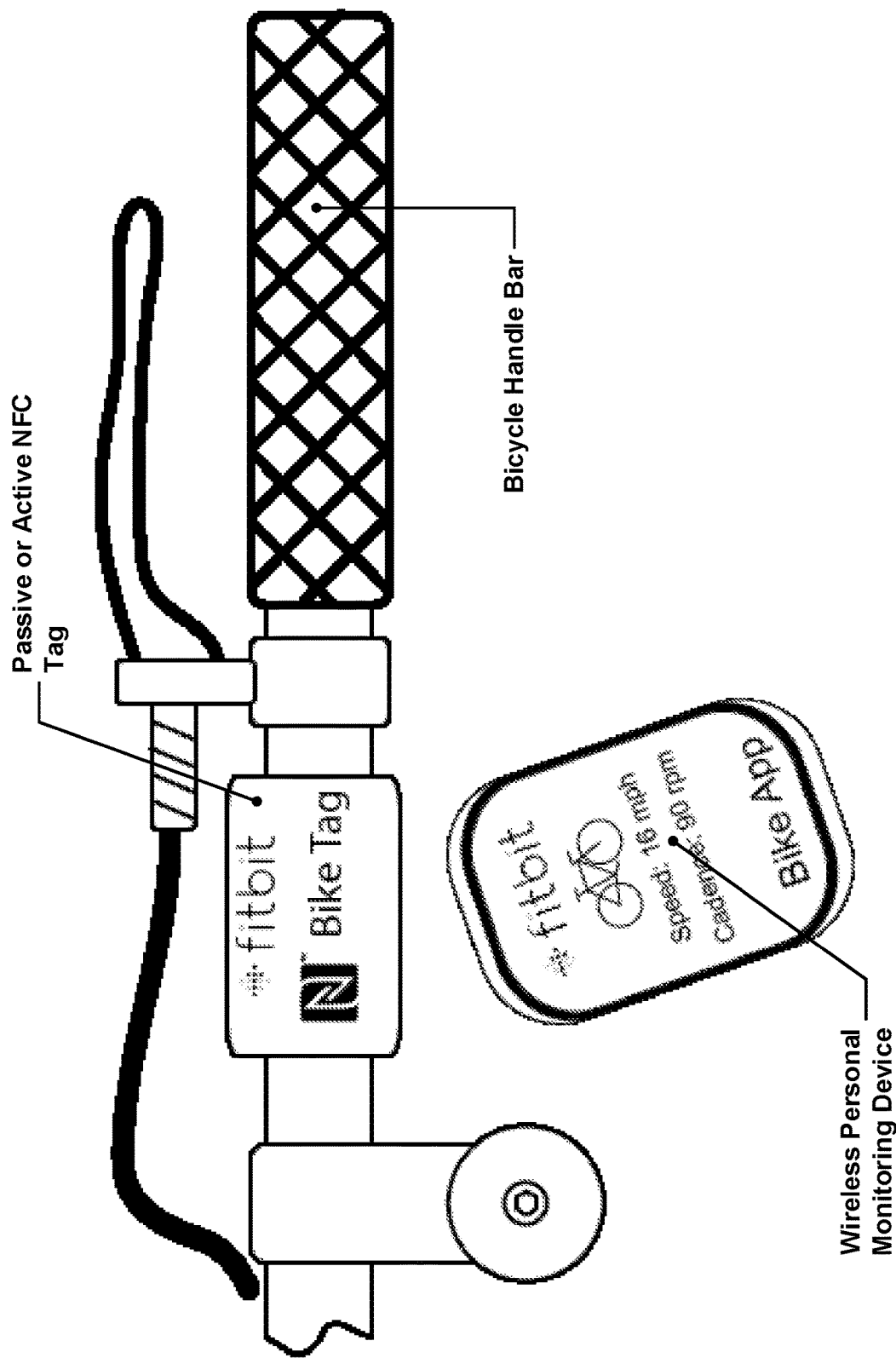
FIG. 17 illustrates an example of a portable biometric monitoring device that has a bicycle application on it that may display bicycle speed and/or pedaling cadence, among other metrics.

FIG. 17 illustrates an example of a portable biometric monitoring device that has a bicycle application on it that may display bicycle speed and/or pedaling cadence, among other metrics. The app may be activated whenever the biometric monitoring device comes into proximity of a passive or active NFC tag. This NFC tag may be attached to the user's handlebars.

In another embodiment, the biometric monitoring device may include a location sensor (for example, GPS circuitry) and pulse waveform sensor (for example, photoplethysmography circuitry) to generate GPS- or location-related data and heart rate-related data, respectively. (See, for example, FIGS. 19B and 19C). The biometric monitoring device may then fuse, process and/or combine data from these two In addition thereto, or in lieu thereof, some embodiments of biometric monitoring devices may employ GPS-related data and photoplethysmography-related data (notably, each of which may be considered data streams) to determine or correlate the user's heart rate according to activity levels— for example, as determined by the user's acceleration, speed, location and/or distance traveled (as measured by the GPS and/or determined from GPS-related data). (See, for example, FIGS. 19B and 19C). Here, in one embodiment, heart rate as a function of speed may be "plotted" for the user, or the data may be broken down into different levels including, but not limited to, sleeping, resting, sedentary, moderately active, active, and highly active.

Indeed, some embodiments of biometric monitoring devices may also correlate GPS-related data to a database of predetermined geographic locations that have activities associated with them for a set of predetermined conditions. For example, activity determination and corresponding physiological classification (for example, heart rate classification) may include correlating a user's GPS coordinates that correspond to location(s) of exercise equipment, health club and/or gym and physiological data. Under these circumstances, a user's heart rate during, for example a gym workout, may be automatically measured and displayed. Notably, many physiological classifications may be based on GPS-related data including location, acceleration, altitude, distance and/or velocity. Such a database including geographic data and physiological data may be compiled, developed and/or stored on the biometric monitoring device and/or external computing device. Indeed, in one embodiment, the user may create their own location database or add to or modify the location database to better classify their activities.

In another embodiment, the user may simultaneously wear multiple biometric monitoring devices (having any of the features described herein). The biometric monitoring devices of this embodiment may communicate with each other or a remote device using wired or wireless circuitry to calculate, for example, biometric or physiologic qualities or quantities that, for example, may be difficult or inaccurate to calculate otherwise, such as pulse transit time. The use of multiple sensors may also improve the accuracy and/or precision of biometric measurements over the accuracy and/or precision of a single sensor. For example, having a biometric tracking device on the waist, wrist, and ankle may improve the detection of the user taking a step over that of a single device in only one of those locations. Signal processing may be performed on the biometric tracking devices in a distributed or centralized method to provide measurements improved over that of a single device. This signal processing may also be performed remotely and communicated back to the biometric tracking devices after processing.

In another embodiment, heart rate or other biometric data may be correlated to a user's food log (a log of foods ingested by a user, their nutritional content, and portions thereof). Food log entries may be entered into the food log automatically or may be entered by the user themselves through interaction with the biometric monitoring device (or a secondary or remote device, e.g., a smartphone, in communication with the biometric monitoring device or some other device, e.g., a server, in communication with the biometric monitoring device). Information may be presented to the user regarding the biometric reaction of their body to one or more food inputs. For example, if a user has coffee, their heart rate may rise as a result of the caffeine. In another example, if a user has a larger portion of food late at night, it may take longer for them to fall asleep than usual. Any combination of food input and corresponding result in biometrics may be incorporated into such a feedback system.

The fusion of food intake data and biometric data may also enable some embodiments of biometric monitoring device to make an estimation of a user's glucose level. This may be particularly useful for users who have diabetes. With an algorithm which relates the glucose level to the user's activity (e.g. walking, running, calorie burn) and nutritional intake, a biometric monitoring device may be able to advise the user when they are likely to have an abnormal blood sugar level.

Processing Task Delegation

Embodiments of biometric monitoring devices may include one or more processors. Figures. For example, an independent application processor may be used to store and execute applications that utilize sensor data acquired and processed by one or more sensor processors (processor(s) that process data from physiological, environmental, and/or activity sensors). In the case where there are multiple sensors, there may also be multiple sensor processors. An application processor may have sensors directly connected to it as well. Sensor and application processors may exist as separate discrete chips or exist within the same packaged chip (multi-core). A device may have a single application processor, or an application processor and sensor processor, or a plurality of application processors and sensor processors.

In one embodiment, the sensor processor may be placed on a daughterboard that consists of all of the analog components. This board may have some of the electronics typically found on the main PCB such as, but not limited to, transimpedance amplifiers, filtering circuits, level shifters, sample-and-hold circuits, and a microcontroller unit. Such a configuration may allow the daughterboard to be connected to the main PCB through the use of a digital connection rather than an analog connection (in addition to any necessary power or ground connections). A digital connection may have a variety of advantages over an analog daughterboard to main PCB connection, including, but not limited to, a reduction in noise and a reduction in the number of necessary cables. The daughterboard may be connected to the main board through the use of a flex cable or set of wires.

Multiple applications may be stored on an application processor. An application may consist of executable code and data for the application, but is not limited to these. Data may consist of graphics or other information required to execute the application or it may be information output generated by the application. The executable code and data for the application may both reside on the application processor (or memory incorporated therein) or the data for the application may be stored and retrieved from an external memory. External memory may include but is not limited to NAND flash, NOR flash, flash on another processor, other solid-state storage, mechanical or optical disks, RAM, etc.

The executable code for an application may also be stored in an external memory. When a request to execute an application is received by the application processor, the application processor may retrieve the executable code and/or data from the external storage and execute it. The executable code may be temporarily or permanently stored on the memory or storage of the application processor. This allows the application to be executed more quickly on the next execution request, since the step of retrieval is eliminated. When the application is requested to be executed, the application processor may retrieve all of the executable code of the application or portions of the executable code. In the latter case, only the portion of executable code required at that moment is retrieved. This allows applications that are larger than the application processor's memory or storage to be executed.

The application processor may also have memory protection features to prevent applications from overwriting, corrupting, interrupting, blocking, or otherwise interfering with other applications, the sensor system, the application processor, or other components of the system.

Applications may be loaded onto the application processor and/or any external storage via a variety of wired, wireless, optical, or capacitive mechanisms including, but not limited to, USB, Wi-Fi, Bluetooth, Bluetooth Low Energy, NFC, RFID, Zigbee.

Applications may also be cryptographically signed with an electronic signature. The application processor may restrict the execution of applications to those that have the correct signature.

Integration of Systems in a Biometric Monitoring Device

In some implementations of biometric monitoring devices, some sensors or electronic systems in the biometric monitoring device may be integrated with one another or may share components or resources. For example, a photodetector for an optically-based pulse waveform sensor (such as may be used in the heart-rate sensors discussed in U.S. Provisional Patent Application No. 61/946,439, filed Feb. 28, 2014, and previously incorporated by reference herein, may also serve as a photodetector for determining ambient light level, such as may be used to correct for the effects of ambient light on the pulse waveform sensor reading. For example, if the light source for such a heart rate detector is turned off, the light that is measured by the photodetector may be indicative of the amount of ambient light that is present.

In some implementations of a biometric monitoring device, the biometric monitoring device may be configured or communicated with using onboard optical sensors such as the components in an optical pulse waveform monitor or heart rate monitor. For example, the photodetectors of an optical heart-rate sensor (or, if present, an ambient light sensor) may also serve as a receiver for an optically-based transmission channel, e.g., infrared communications.

In some implementations of a biometric monitoring device, a hybrid antenna may be included that combines a radio frequency antenna, e.g., a Bluetooth antenna or GPS antenna, with an inductive loop, such as may be used in a near-field communications (NFC) tag or in an inductive charging system. In such implementations, the functionality for two different systems may be provided in one integrated system, saving packing volume. In such a hybrid antenna, an inductive loop may be placed in close proximity to the radiator of an inverted-F antenna. The inductive loop may inductively couple with the radiator, allowing the inductive loop to serve as a planar element of the antenna for radio-frequency purposes, thus forming, for example, a planar inverted-F antenna. At the same time, the inductive loop may also serve its normal function, e.g., such as providing current to an NFC chip through inductive coupling with an electromagnetic field generated by an NFC reader. Examples of such hybrid antenna systems are discussed in more detail in U.S. Provisional Patent Application No. 61/948,470, filed Mar. 5, 2014, which was previously incorporated herein by reference in the "Cross-Reference to Related Applications" section and which is again hereby incorporated by reference with respect to content directed at hybrid antenna structures. Of course, such hybrid antennas may also be used in other electronic devices other than biometric monitoring devices, and such non-biometric-monitoring-device use of hybrid antennas is contemplated as being within the scope of this disclosure.

User Interface with the Device

Some embodiments of a biometric monitoring device may include functionality for allowing one or more methods of interacting with the device either locally or remotely.

In some embodiments, the biometric monitoring device may convey data visually through a digital display. The physical embodiment of this display may use any one or a plurality of display technologies including, but not limited to one or more of LED, LCD, AMOLED, E-Ink, Sharp display technology, graphical displays, and other display technologies such as TN, HTN, STN, FSTN, TFT, IPS, and OLET. This display may show data acquired or stored locally on the device or may display data acquired remotely from other devices or Internet services. The biometric monitoring device may use a sensor (for example, an Ambient Light Sensor, "ALS") to control or adjust the amount of screen backlighting, if backlighting is used. For example, in dark lighting situations, the display may be dimmed to conserve battery life, whereas in bright lighting situations, the display brightness may be increased so that it is more easily read by the user.

In another embodiment, the biometric monitoring device may use single or multicolor LEDs to indicate a state of the device. States that the biometric monitoring device may indicate using LEDs may include, but are not limited to, biometric states such as heart rate or application states such as an incoming message or that a goal has been reached. These states may be indicated through the LED's color, the LED being on or off (or in an intermediate intensity), pulsing (and/or rate thereof) of the LEDs, and/or a pattern of light intensities from completely off to highest brightness. In one embodiment, an LED may modulate its intensity and/or color with the phase and frequency of the user's heart rate.

In some embodiments, the use of an E-Ink display may allow the display to remain on without the battery drain of a non-reflective display. This "always-on" functionality may provide a pleasant user experience in the case of, for example, a watch application where the user may simply glance at the biometric monitoring device to see the time. The E-Ink display always displays content without including the battery life of the device, allowing the user to see the time as they would on a traditional watch.

Some implementations of a biometric monitoring device may use a light such as an LED to display the heart rate of the user by modulating the amplitude of the light emitted at the frequency of the user's heart rate. The device may depict heart rate zones (e.g., aerobic, anaerobic, etc.) through the color of an LED (e.g., green, red) or a sequence of LEDs that light up in accordance with changes in heart rate (e.g., a progress bar). The biometric monitoring device may be integrated or incorporated into another device or structure, for example, glasses or goggles, or communicate with glasses or goggles to display this information to the user.

Some embodiments of a biometric monitoring device may also convey information to a user through the physical motion of the device. One such embodiment of a method to physically move the device is the use of a vibration-inducing motor. The device may use this method alone, or in combination with a plurality of other motion-inducing technologies.

In some implementations, a biometric monitoring device may convey information to a user through audio feedback. For example, a speaker in the biometric monitoring device may convey information through the use of audio tones, voice, songs, or other sounds.

These three information communication methods—visual, motion, and auditory— may, in various embodiments of biometric monitoring devices, be used alone or in any combination with each other or another method of communication to communicate any one or plurality of the following information:

That a user needs to wake up at certain time
That a user should wake up as they are in a certain sleep phase
That a user should go to sleep as it is a certain time
That a user should wake up as they are in a certain sleep phase and in a preselected time window bounded by the earliest and latest time that the user wants to wake up.
That an email was received
That the user has been inactive for a certain period of time. Notably, this may integrate with other applications like, for instance, a meeting calendar or sleep tracking application to block out, reduce, or adjust the behavior of the inactivity alert.
That the user has been active for a certain period of time
That the user has an appointment or calendar event
That the user has reached a certain activity metric
That the user has gone a certain distance
That the user has reached a certain mile pace
That the user has reached a certain speed
That the user has accumulated a certain elevation gain
That the user has taken a certain number of steps That the user has had a pulse waveform measurement or heart rate measurement recently That the user's heart rate has reached a certain level That the user has a normal, active, or resting heart rate of a specific value or in a specific range That the user's heart rate has enter or exited a certain goal range or training zone That the user has a new heart rate "zone" goal to reach, as in the case of heart rate zone training for running, bicycling, swimming, etc. activities That the user has swum a lap or completed a certain number of laps in a pool An external device has information that needs to be communicated to the user such as an incoming phone call or any one of the above alerts That the user has reached a certain fatigue goal or limit. In one embodiment, fatigue may be determined through a combination of heart rate, galvanic skin response, motion sensor, and/or respiration data These examples are provided for illustration and are not intended to limit the scope of information that may be communicated by such embodiments of biometric monitoring devices (for example, to the user). Note that the data used to determine whether or not an alert condition is met may be acquired from a first device and/or one or more secondary devices. The biometric monitoring device itself may determine whether the criteria or conditions for an alert have been met. Alternatively, a computing device in communication with the biometric monitoring device (e.g., a server and/or a mobile phone) may determine when the alert should occur. In view of this disclosure, other information that the biometric monitoring device may communicate to the user may be envisioned by one of ordinary skill in the art. For example, the biometric monitoring device may communicate with the user when a goal has been met. The criteria for meeting this goal may be based on physiological, contextual, and environmental sensors on a first device, and/or other sensor data from one or more secondary devices. The goal may be set by the user or may be set by the biometric monitoring device itself and/or another computing device in communication with the biometric monitoring device (e.g. a server). In an example embodiment, the biometric monitoring device may vibrate when a biometric goal is met.

Some embodiments of biometric monitoring devices of the present disclosure may be equipped with wireless and/or wired communication circuitry to display data on a secondary device in real time. For example, such biometric monitoring devices may be able to communicate with a mobile phone via Bluetooth Low Energy in order to give real-time feedback of heart rate, heart rate variability, and/or stress to the user. Such biometric monitoring devices may coach or grant "points" for the user to breathe in specific ways that alleviate stress (e.g. by taking slow, deep breaths). Stress may be quantified or evaluated through heart rate, heart rate variability, skin temperature, changes in motion-activity data and/or galvanic skin response.

Some embodiments of biometric monitoring devices may receive input from the user through one or more local or remote input methods. One such embodiment of local user input may use a sensor or set of sensors to translate a user's movement into a command to the device. Such motions could include but may not be limited to tapping, rolling the wrist, flexing one or more muscles, and swinging one's arm. Another user input method may be through the use of a button such as, but not limited to, capacitive touch buttons, capacitive screen buttons, and mechanical buttons. In one embodiment, the user interface buttons may be made of metal. In embodiments where the screen uses capacitive touch detection, it may always be sampling and ready to respond to any gesture or input without an intervening event such as pushing a physical button. Such biometric monitoring devices may also take input through the use of audio commands. All of these input methods may be integrated into biometric monitoring devices locally or integrated into a remote device that can communicate with such biometric monitoring devices, either through a wired or wireless connection. In addition, the user may also be able to manipulate the biometric monitoring device through a remote device. In one embodiment, this remote device may have Internet connectivity.

Alarms

In some embodiments, the biometric monitoring device of the present disclosure may act as a wrist-mounted vibrating alarm to silently wake the user from sleep. Such biometric monitoring devices may track the user's sleep quality, waking periods, sleep latency, sleep efficiency, sleep stages (e.g., deep sleep vs REM), and/or other sleep-related metrics through one or a combination of heart rate, heart rate variability, galvanic skin response, motion sensing (e.g., accelerometer, gyroscope, magnetometer), and skin temperature. The user may specify a desired alarm time or window of time (e.g., set alarm to go off between 7 am and 8 am). Such embodiments may use one or more of the sleep metrics to determine an optimal time within the alarm window to wake the user. In one embodiment, when the vibrating alarm is active, the user may cause it to hibernate or turn off by slapping or tapping the device (which is detected, for example, via motion sensor(s), a pressure/force sensor, and/or capacitive touch sensor in the device). In one embodiment, the device may attempt to arouse the user at an optimum point in the sleep cycle by starting a small vibration at a specific user sleep stage or time prior to the alarm setting. It may progressively increase the intensity or noticeability of the vibration as the user progresses toward wakefulness or toward the alarm setting. (See, for example, FIG. 15).

Figure 15:
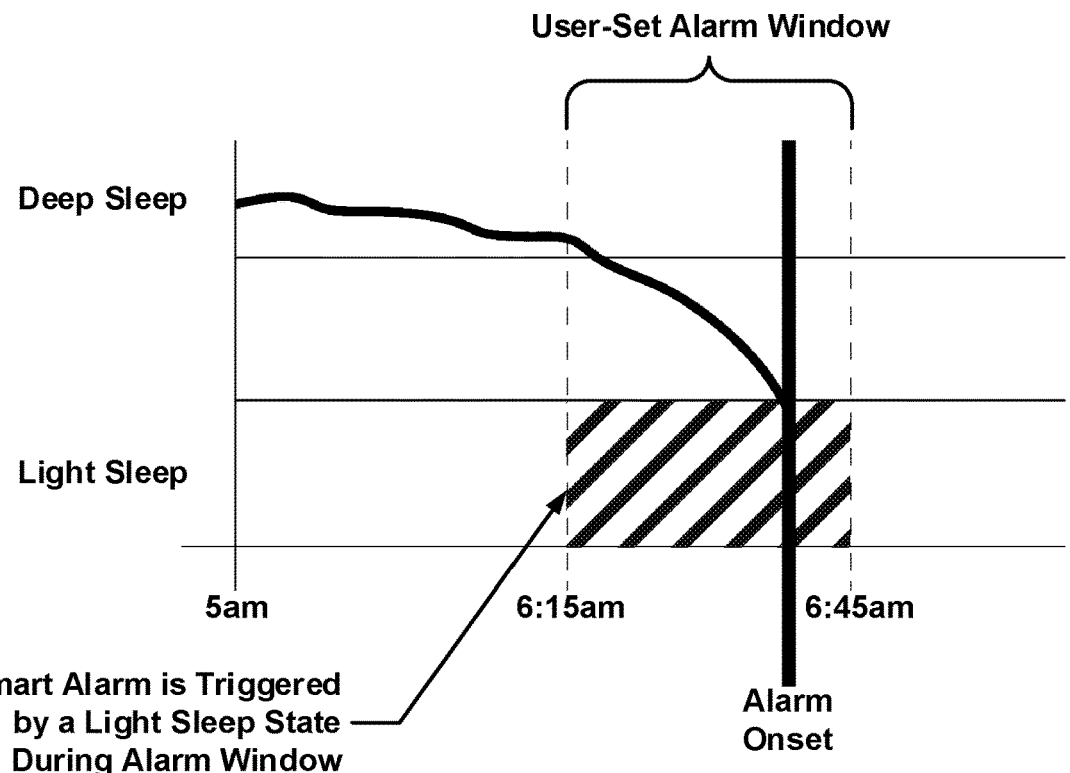
FIG. 15 illustrates functionality of an example biometric monitoring device smart alarm feature.

FIG. 15 illustrates functionality of an example portable biometric monitoring device smart alarm feature. The biometric monitoring device may be able to detect or may be in communication with a device that can detect the sleep stage or state of a user (e.g., light or deep sleep). The user may set a window of time which they would like to be awoken (e.g., 6:15 am to 6:45 am). The smart alarm may be triggered by the user going into a light sleep state during the alarm window.

The biometric monitoring device may be configured to allow the user to select or create an alarm vibration pattern of their choice. The user may have the ability to "snooze" or postpone an alarm event. In one embodiment, the user may be able to set the amount of delay for the "snooze" feature—the delay being the amount of time before the alarm will go off again. They may also be able to set how many times the snooze feature may be activated per alarm cycle. For example, a user may choose a snooze delay of 5 minutes and a maximum sequential snooze number to be 3. Therefore, they can press snooze up to 3 times to delay the alarm by 5 minutes each time they press snooze to delay the alarm. In such embodiments, the snooze function will not turn off the alarm if the user attempts to press snooze a fourth time.

Some biometric monitoring devices may have information about the user's calendar and/or schedule. The user's calendar information may be entered directly into the biometric monitoring device or it may be downloaded from a different device (e.g. a smartphone). This information may be used to automatically set alarms or alarm characteristics. For example, if a user has a meeting at 9 am in the morning, the biometric monitoring device may automatically wake the user up at 7:30 am to allow the user enough time to prepare for and/or get to the meeting. The biometric monitoring device may determine the amount of time required for the user to prepare for the meeting based on the user's current location, the location of the meeting, and the amount of time it would take to get the location of the meeting from the user's current location. Alternatively, historical data about how long the user takes to get to the meeting location and/or prepare to leave for the meeting (e.g. how long it takes to wake up, take a shower, have breakfast, etc. in the morning) may be used to determine at what time to wake the user. A similar functionality may be used for calendar events other than meetings such as eating times, sleeping times, napping times, and exercise times.

In some embodiments, the biometric monitoring device may use information on when the user went to sleep to determine when an alarm should go off to wake the user. This information may supplement calendar information described herein. The user may have a goal of approximately how many hours of sleep they would like to get each night or week. The biometric monitoring device may set the morning alarm at the appropriate time for the user to meet these sleep goals. In addition to amount of time that the user would like to sleep each night, other sleep goals that the user may set may include, but are not limited to, the amount of deep sleep, REM sleep, and light sleep that the user experiences while sleeping, all of which may be used by the biometric monitoring device to determine when to set an alarm in the morning. Additionally, the user may be alerted at night when they should go to bed to meet their sleep goals. Additionally, the user may be alerted during the day when they should take a nap to meet their sleep goals. The time at which to alert a user that they should take a nap may be determined by factors that optimize the user's sleep quality during the nap, subsequent naps, or night-time sleep. For example, the user is likely to have a hard time falling asleep at night if they took a nap in the early evening. The user may also be advised to eat certain foods or drinks or avoid certain foods or drinks to optimize their sleep quality. For example, a user may be discouraged from drinking alcohol close to their bed time as it is likely to decrease their sleep quality. The user may also be advised to perform certain activities or avoid certain activities to optimize their sleep quality. For example, a user may be encouraged to exercise in the early afternoon to improve their sleep quality. A user may be discouraged from exercising or watching TV close to their bedtime to improve their sleep quality.

User Interface with a Secondary Device

In some embodiments, the biometric monitoring device may transmit and receive data and/or commands to and/or from a secondary electronic device. The secondary electronic device may be in direct or indirect communication with the biometric monitoring device. Direct communication refers herein to the transmission of data between a first device and a secondary device without any intermediary devices. For example, two devices may communicate to one another over a wireless connection (e.g. Bluetooth) or a wired connection (e.g. USB). Indirect communication refers to the transmission of data between a first device and a secondary device with the aid of one or multiple intermediary third devices which relay the data. Third devices may include, but are not limited to, a wireless repeater (e.g. WiFi repeater), a computing device such as a smartphone, laptop, desktop or tablet computer, a cell phone tower, a computer server, and other networking electronics. For example, a biometric device may send data to a smartphone which forwards the data through a cellular network data connection to a server which is connected through the internet to the cellular network.

In some embodiments, the secondary device that acts as a user interface to the biometric monitoring device may consist of a smartphone. An app on the smart phone may facilitate and/or enable the smartphone to act as a user interface to the biometric monitoring device. The biometric monitoring device may send biometric and other data to the smartphone in real-time or with some delay. The smartphone may send a command or commands to the biometric monitoring device, for example, to instruct it to send biometric and other data to the smartphone in real-time or with some delay. For example, if the user enters a mode in the app for tracking a run, the smartphone may send a command to the biometric device to instruct it to send data in real-time. Therefore, the user can track their run on their app as they go along without any delay.

Such a smartphone may have one or multiple apps to enable the user to view data from their biometric device or devices. The app may, by default, open to a "dashboard" page when the user launches or opens the app. On this page, summaries of data totals such as the total number of steps, floors climbed miles traveled, calories burned, calories consumed and water consumed may be shown. Other pertinent information such as the last time the app received data from the biometric monitoring device, metrics regarding the previous night's sleep (e.g. when the user went to sleep, woke up, and how long they slept for), and how many calories the user can eat in the day to maintain their caloric goals (e.g. a calorie deficit goal to enable weight loss) may also be shown. The user may be able to choose which of these and other metrics are shown on the dashboard screen. The user may be able to see these and other metrics on the dashboard for previous days. They may be able to access previous days by pressing a button or icon on a touchscreen. Alternatively, gestures such as swiping to the left or right may enable the user to navigate through current and previous metrics.

The smartphone app may also have another page which provides a summary of the user's activities. Activities may include, but are not limited to, walking, running, biking, cooking, sitting, working, swimming, working out, weightlifting, commuting, and yoga. Metrics pertinent to these activities may be presented on this page. For example, a bar graph may show how the number of steps the user took for different portions of the day (e.g. how many steps every 5 minutes or 1 hour). In another example, the amount of time the user spent performing a certain activity and how many calories were burned in this period of time may be displayed. Similar to the dashboard page, the app may provide navigational functionality to allow the user to see these and other metrics for past days. Other time periods such as an hour, minute, week, month or year may also be selected by the user to enable them to view trends and metrics of their activities over shorter or larger spans of time.

The smartphone app may also have an interface to log food that has been, or will be, eaten by the user. This interface may have a keyword search feature to allow the user to quickly find the food that they would like to enter into their log. As an alternative to, or in addition to, searching for foods, users may have the ability to find a food to log by navigating through a menu or series of menus. For example, a user may choose the following series of categories—breakfast/cereal/healthy/oatmeal to arrive at the food which they would like to log (e.g., apple-flavored oatmeal). At any one of these menus, the user may be able to perform a keyword search. For example, the user may search for "oatmeal" after having selected the category "breakfast" to search for the keyword "oatmeal" within the category of breakfast foods. After having selected the food that they would like to log, the user may be able to modify or enter the serving size and nutritional content. After having logged at least one food, the app may display a summary of the foods that were logged in a certain time period (e.g. a day) and the nutritional content of the foods (individual and total calorie content, vitamin content, sugar content, etc.).

The smartphone app may also have a page that displays metrics regarding the user's body such as the user's weight, body fat percentage, BMI, and waist size. It may display a graph or graphs showing the trend of one or multiple of these metrics over a certain period of time (e.g., two weeks). The user may be able to choose the value of this period of time and view previous time periods (e.g., last month).

The smartphone app may also a page which allows the user to enter how much water the user has consumed. Each time the user drinks some water, they may enter that amount in the unit of their choice (e.g., ozs., cups, etc.). The app may display the total of all of the water the user has logged within a certain time period (e.g., a day). The app may allow the user to see previously-logged water entries and daily totals for previous days as well as the current day.

The smartphone app may also have a page that displays online friends of the user. This "friends" page may enable the user to add or request new friends (e.g., by searching for their name or by their email address). This page may also display a leaderboard of the user and his or her friends. The user and his or friends may be ranked based on one or more metrics. For example, the user and his or her friends may be ranked using the total of the past seven days' step counts.

The smartphone app may also have a page that shows metrics regarding the user's sleep for the previous night and/or previous nights. This page may also enable the user to log when they slept in the past by specifying when they went to bed and when they woke. The user may also have the ability to enter a subjective metric about their sleep (e.g., bad night's rest, good night's rest, excellent night's rest, etc.). The user may be able to view these metrics for days or time periods (e.g., two weeks) in the past. For example, the sleep page may default to showing a bar graph of the amount of time the user slept each night in the last two weeks. The user may be able to also view a bar graph of the amount of time the user slept each night in the last month.

The user may also be able to access the full capabilities of the smartphone app described herein (e.g., the ability to enter food logs, view dashboard, etc.) through an alternative or additional interface. In one embodiment, this alternative interface may consist of a webpage that is hosted by a server in indirect communication with the biometric monitoring device. The webpage may be accessed through any internet connected device using a program such as a web browser.

Wireless Connectivity and Data Transmission

Some embodiments of biometric monitoring devices of the present disclosure may include a means of wireless communication to transmit and receive information from the Internet and/or other devices. The wireless communication may consist of one or more interfaces such as Bluetooth, ANT, WLAN, power-line networking, and cell phone networks. These are provided as examples and should not be understood to exclude other existing wireless communication methods or protocols, or wireless communications techniques or protocols that are yet to be invented.

The wireless connection may be bi-directional. The biometric monitoring device may transmit, communicate and/or push its data to other devices, e.g., smart phones, computers, etc., and/or the Internet, e.g., web servers and the like. The biometric monitoring device may also receive, request and/or pull data from other devices and/or the Internet.

The biometric monitoring device may act as a relay to provide communication for other devices to each other or to the Internet. For example, the biometric monitoring device may connect to the Internet via WLAN but also be equipped with an ANT radio. An ANT device may communicate with the biometric monitoring device to transmit its data to the Internet through the biometric monitoring device's WLAN (and vice versa). As another example, the biometric monitoring device may be equipped with Bluetooth. If a Bluetooth-enabled smart phone comes within range of the biometric monitoring device, the biometric monitoring device may transmit data to, or receive data from, the Internet through the smart phone's cell phone network. Data from another device may also be transmitted to the biometric monitoring device and stored (or vice versa) or transmitted at a later time.

Embodiments of biometric monitoring devices of the present disclosure may also include functionality for streaming or transmitting web content for display on the biometric monitoring device. The following are typical examples of such content:

1. Historical graphs of heart rate and/or other data measured by the device but stored remotely
2. Historical graphs of user activity and/or foods consumed and/or sleep data that are measured by other devices and/or stored remotely (e.g., such as at a website like fitbit.com)
3. Historical graphs of other user-tracked data that are stored remotely. Examples include heart rate, blood pressure, arterial stiffness, blood glucose levels, cholesterol, duration of TV watching, duration of video game play, mood, etc.
4. Coaching and/or dieting data based on one or more of the user's heart rate, current weight, weight goals, food intake, activity, sleep, and other data.
5. User progress toward heart rate, weight, activity, sleep, and/or other goals.
6. Summary statistics, graphics, badges, and/or metrics (e.g., "grades") to describe the aforementioned data
7. Comparisons between the aforementioned data for the user and similar data for his/her "friends" with similar devices and/or tracking methods
8. Social content such as Twitter feeds, instant messaging, and/or Facebook updates
9. Other online content such as newspaper articles, horoscopes, weather reports, RSS feeds, comics, crossword puzzles, classified advertisements, stock reports, and websites
10. Email messages and calendar schedules Content may be delivered to the biometric monitoring device according to different contexts. For instance, in the morning, news and weather reports may be displayed along with the user's sleep data from the previous night. In the evening, a daily summary of the day's activities may be displayed.

Various embodiments of biometric monitoring devices as disclosed herein may also include NFC, RFID, or other short-range wireless communication circuitry that may be used to initiate functionality in other devices. For instance, a biometric monitoring device may be equipped with an NFC antenna so that when a user puts it into close proximity with a mobile phone, an app is launched automatically on the mobile phone.

These examples are provided for illustration and are not intended to limit the scope of data that may be transmitted, received, or displayed by the device, nor any intermediate processing that may occur during such transfer and display. In view of this disclosure/application, many other examples of data that may be streamed to or via a biometric monitoring device may be envisioned by one reasonably skilled in the art.

Charging and Data Transmission

Some embodiments of biometric monitoring devices may use a wired connection to charge an internal rechargeable battery and/or transfer data to a host device such as a laptop or mobile phone. In one embodiment, similar to one discussed earlier in this disclosure, the biometric monitoring device may use magnets to help the user align the biometric monitoring device to a dock or cable. The magnetic field of magnets in the dock or cable and the magnets in the device itself may be strategically oriented so as to force the biometric monitoring device to self-align with the dock or cable (or, more specifically, a connector on the cable) and so as to provide a force that holds the biometric monitoring device in the dock or to the cable. The magnets may also be used as conductive contacts for charging or data transmission purposes. In another embodiment, a permanent magnet may only be used in the dock or cable side and not in the biometric monitoring device itself. This may improve the performance of the biometric monitoring device where the biometric monitoring device employs a magnetometer. If there is a magnet in the biometric monitoring device, the strong field of a nearby permanent magnet may make it significantly more difficult for the magnetometer to accurately measure the earth's magnetic field. In such embodiments, the biometric monitoring device may utilize a ferrous material in place of a magnet, and the magnets on the dock or cable side may attach to the ferrous material.

In another embodiment, the biometric monitoring device may contain one or more electromagnets in the biometric monitoring device body. The charger or dock for charging and data transmission may also contain an electromagnet and/or a permanent magnet. The biometric monitoring device could only turn on its electromagnet when it is close to the charger or dock. The biometric monitoring device may detect proximity to the dock or charger by looking for the magnetic field signature of a permanent magnet in the charger or dock using a magnetometer. Alternatively, the biometric monitoring device may detect proximity to the charger by measuring the Received Signal Strength Indication (RSSI) of a wireless signal from the charger or dock, or, in some embodiments, by recognizing an NFC or RFID tag associated with the charger or dock. The electromagnet could be reversed, creating a force that repels the device from the charging cable or dock either when the device doesn't need to be charged, synced, or when it has completed syncing or charging. In some embodiments, the charger or dock may include the electromagnet and may be configured (e.g., a processor in the charger or dock may be configured via program instructions) to turn the electromagnet on when a biometric monitoring device is connected for charging (the electromagnet may normally be left on such that a biometric monitoring device that is placed on the charger is drawn against the charger by the electromagnet, or the electromagnet may be left off until the charger determines that a biometric monitoring device has been placed on the charger, e.g., through completion of a charging circuit, recognition of an NFC tag in the biometric monitoring device, etc., and then turned on to draw the biometric monitoring device against the charger. Upon completion of charging (or of data transfer, if the charger is actually a data transfer cradle or a combined charger/data transfer cradle), the electromagnet may be turned off (either temporarily or until the biometric monitoring device is again detected as being placed on the charger) and the biometric monitoring device may stop being drawn against the charger. In such embodiments, it may be desirable to orient the interface between the biometric monitoring device and the charger such that, in the absence of a magnetic force generated by the electromagnet, the biometric monitoring device would fall off of the charger or otherwise shift into a visibly different position from the charging position (to visually indicate to a user that charging or data transfer is complete).

Sensor Use in Data Transfer

In some implementations, biometric monitoring devices may include a communications interface that may switch between two or more protocols that have different data transmission rates and different power consumption rates. Such switching may be driven by data obtained from various sensors of the biometric monitoring device. For example, if Bluetooth is used, the communications interface may switch between using Bluetooth base rate/enhanced data rate (BR/EDR) and Bluetooth low energy (BLE) protocols responsive to determinations made based on data from the sensors of the biometric monitoring device. For example, the lower-power, slower BLE protocol may be used when sensor data from accelerometers in a biometric monitoring device indicates that the wearer is asleep or otherwise sedentary. By contrast, the higher-power, faster BR/EDR protocol may be used when sensor data from the accelerometers in a biometric monitoring device indicates that the wearer is walking around. Such adaptive data transmission techniques and functionality are discussed further in U.S. Provisional Patent Application No. 61/948,468, filed Mar. 5, 2014, which was previously incorporated herein by reference in the "Cross-Reference to Related Applications" section and which is again hereby incorporated by reference with respect to content directed at adaptive data transfer rates in biometric monitoring devices.

Such communication interfaces may also serve as a form of sensor for a biometric monitoring device. For example, a wireless communications interface may allow a biometric monitoring device to determine the number and type of devices that are within range of the wireless communications interface. Such data may be used to determine if the biometric monitoring device is in a particular context, e.g., indoors, in a car, etc., and to change its behavior in various ways in response to such a determination. For example, as discussed in U.S. Provisional Patent Application No. 61/948,468 (incorporated by reference above), such contexts may be used to drive the selection of a particular wireless communications protocol to use for wireless communications.

Configurable App Functionality

In some embodiments, biometric monitoring devices of the present disclosure may include a watch-like form factor and/or a bracelet, armlet, or anklet form factor and may be programmed with "apps" that provide specific functionality and/or display specific information. Apps may be launched or closed by a variety of means including, but not limited to, pressing a button, using a capacitive touch sensor, performing a gesture that is detected by an accelerometer, moving to a specific location or area detected by a GPS or motion sensor, compressing the biometric monitoring device body (thereby creating a pressure signal inside the device that may be detected by an altimeter inside the biometric monitoring device), or placing the biometric monitoring device close to an NFC tag that is associated with an app or set of apps. Apps may also be automatically triggered to launch or close by certain environmental or physiological conditions including, but not limited to, detection of a high heart rate, detection of water using a wet sensor (to launch a swimming application, for example), a certain time of day (to launch a sleep tracking application at night, for example), a change in pressure and motion characteristic of a plane taking off or landing to launch and close an "airplane" mode app. Apps may also be launched or closed by meeting multiple conditions simultaneously. For example, if an accelerometer detects that a user is running and the user presses a button, the biometric monitoring device may launch a pedometer application, an altimeter data collection application, and/or display. In another case where the accelerometer detects swimming and the user presses the same button, it may launch a swimming lap-counting application.

In some embodiments, the biometric monitoring device may have a swim-tracking mode that may be launched by starting a swimming app. In this mode, the biometric monitoring device's motion sensors and/or magnetometer may be used to detect swim strokes, classify swim stroke types, detect swimming laps, and other related metrics such as stroke efficiency, lap time, speed, distance, and calorie burn. Directional changes indicated by the magnetometer may be used to detect a diversity of lap turn methods. In a preferred embodiment, data from a motion sensor and/or pressure sensor may be used to detect strokes.

In another embodiment, a bicycling app may be launched by moving the biometric monitoring device within proximity of an NFC or RFID tag that is located on the bicycle, on a mount on the bicycle, or in a location associated with a bicycle including, but not limited to, a bike rack or bike storage facility. (See, for example, FIG. 17). The app launched may use a different algorithm than is normally used to determine metrics including, but not limited to, calories burned, distance travelled, and elevation gained. The app may also be launched when a wireless bike sensor is detected including, but not limited to, a wheel sensor, GPS, cadence sensor, or power meter. The biometric monitoring device may then display and/or record data from the wireless bike sensor or bike sensors.

Additional apps include, but are not limited to, a programmable or customizable watch face, stop watch, music player controller (e.g., mp3 player remote control), text message and/or email display or notifier, navigational compass, bicycle computer display (when communicating with a separate or integrated GPS device, wheel sensor, or power meter), weightlifting tracker, sit-up reps tracker, pull up reps tracker, resistance training form/workout tracker, golf swing analyzer, tennis (or other racquet sport) swing/serve analyzer, tennis game swing detector, baseball swing analyzer, ball throw analyzer (e.g., football, baseball), organized sports activity intensity tracker (e.g., football, baseball, basketball, volleyball, soccer), disk throw analyzer, food bite detector, typing analyzer, tilt sensor, sleep quality tracker, alarm clock, stress meter, stress/relaxation biofeedback game (e.g., potentially in combination with a mobile phone that provides auditory and/or visual cues to train user breathing in relaxation exercises), teeth brushing tracker, eating rate tracker (e.g., to count or track the rate and duration by which a utensil is brought to the mouth for food intake), intoxication or suitability to drive a motor vehicle indicator (e.g., through heart rate, heart rate variability, galvanic skin response, gait analysis, puzzle solving, and the like), allergy tracker (e.g., using galvanic skin response, heart rate, skin temperature, pollen sensing and the like (possibly in combination with external seasonal allergen tracking from, for instance, the internet and possibly determining the user's response to particular forms of allergen, e.g., tree pollen, and alerting the user to the presence of such allergens, e.g., from seasonal information, pollen tracking databases, or local environmental sensors in the biometric monitoring device or employed by the user), fever tracker (e.g., measuring the risk, onset, or progress of a fever, cold, or other illness, possibly in combination with seasonal data, disease databases, user location, and/or user provided feedback to assess the spread of a particular disease (e.g., flu) in relation to a user, and possibly prescribing or suggesting the abstinence of work or activity in response), electronic games, caffeine affect tracker (e.g., monitoring the physiologic response such as heart rate, heart rate variability, galvanic skin response, skin temperature, blood pressure, stress, sleep, and/or activity in either short term or long term response to the intake or abstinence of coffee, tea, energy drinks and/or other caffeinated beverages), drug affect tracker (e.g., similar to the previously mentioned caffeine tracker but in relation to other interventions, whether they be medical or lifestyle drugs such as alcohol, tobacco, etc.), endurance sport coach (e.g., recommending or prescribing the intensity, duration, or profile of a running/bicycling/swimming workout, or suggesting the abstinence or delay of a workout, in accordance with a user specified goal such as a marathon, triathlon, or custom goal utilizing data from, for instance, historical exercise activity (e.g., distance run, pace), heart rate, heart rate variability, health/sickness/stress/fever state), weight and/or body composition, blood pressure, blood glucose, food intake or caloric balance tracker (e.g., notifying the user how many calories he may consume to maintain or achieve a weight), pedometer, and nail biting detector. In some cases, the apps may rely solely on the processing power and sensors of the present disclosure. In other cases, the apps may fuse or merely display information from an external device or set of external devices including, but not limited to, a heart rate strap, GPS distance tracker, body composition scale, blood pressure monitor, blood glucose monitor, watch, smart watch, mobile communication device such as a smart phone or tablet, or server.

In one embodiment, the biometric monitoring device may control a music player on a secondary device. Aspects of the music player that may be controlled include, but are not limited to, the volume, selection of tracks and/or playlists, skipping forward or backward, fast forwarding or rewinding of tracks, the tempo of the track, and the music player equalizer. Control of the music player may be via user input or automatic based on physiological, environmental, or contextual data. For example, a user may be able to select and play a track on their smart phone by selecting the track through a user interface on the biometric monitoring device. In another example, the biometric monitoring device may automatically choose an appropriate track based on the activity level of the user (the activity level being calculated from biometric monitoring device sensor data). This may be used to help motivate a user to maintain a certain activity level. For example, if a user goes on a run and wants to keep their heart rate in a certain range, the biometric monitoring device may play an upbeat or higher tempo track if their heart rate is below the range which they are aiming for.

Automated Functions Triggered by User's Activity

Sleep Stage Triggered Functionality

Sleep stages can be monitored through various biometric signals and methods disclosed herein, such as heart rate, heart rate variability, body temperature, body motions, ambient light intensity, ambient noise level, etc. Such biometrics may be measured using optical sensors, motion sensors (accelerometers, gyroscopic sensors, etc.), microphones, and thermometers, for example, as well as other sensors discussed herein.

The biometric monitoring device may have a communication module as well, including, but not limited to, Wi-Fi (802.xx), Bluetooth (Classic, low power), or NFC. Once the sleep stages are estimated, the sleep stages may be transmitted to a cloud-based system, home server, or main control unit that is connected to communication-enabled appliances (with Wi-Fi, Bluetooth, or NFC) wirelessly. Alternatively, the biometric monitoring device may communicate directly with the communication-enabled appliances. Such communication-enabled appliances may include, for example, kitchen appliances such as microwaves, ovens, coffee grinders/makers, toasters, etc.

Once the sleep stages indicate that it is close the time for the user to wake up, the biometric monitoring device may send out a trigger to the appliances that the user has indicated should be operated automatically. For example, the coffee grinder and maker may be caused to start making coffee, and the toaster may be caused to start warming up bread. The microwave oven may be caused to start cooking oatmeal or eggs as well, and electric kettle to start boiling water. So long as the ingredients are appropriately prepared, this automated signal may trigger breakfast-cooking.

Alertness Detection

Alertness, e.g., a low alertness may correlate with a person being drowsy, may also be detected from the biometrics listed above, and may be used to trigger an appliance such as a coffee maker to start brewing coffee automatically.

Hydration

[1] The portable biometric monitoring device in combination with an activity level tracker may submit the user's activity level to a cloud-based system, home server, main control unit, or appliances directly. This may trigger some actions of the appliances, especially related to hydration, such as starting the ice cube maker of a refrigerator, or lowering operating temperature of a water purifier.

Power Saving

Many appliances typically operate in a low-power idle state that consumes power. Using aggregated information of the user's biometric signals, communication-enabled appliances may be caused to go into a super-low power mode. For example, a water dispenser at home may shut itself down into a super-low-power mode when the user is asleep or out for work, and may start cooling/heating water once the user's activity at home is expected.

Restaurant Recommendation System Based on Location and Activity

Aggregation of real-time biometric signals and location information may be used to create an educated-guess on one or multiple users' needs for a given time, e.g., ionized drink. Combining this guessed need with historical user data on the user's activity levels, activity types, activity time, and activity durations, as well as food intake data logged by the users, an app on a smart phone and/or smart watch may recommend a restaurant that would meet the user's life-style and current need.

For example, a user who just finished a six mile circuit may launch this app. The app may know that this person maintained a high activity level for the past hour, and thus determine that the person may be dehydrated. From the historical user data, the app may also know, for example, that the user's diet is heavy on vegetables but low in sugar. With an optimization algorithm that considers the user's current location, price ranges, and other factors mentioned above, the app may recommend a restaurant that offers smoothies, for example.

Blood Glucose Level and Heart Rate

Biometric monitoring devices that continuously measure biometric signals may provide meaningful information on preconditions of, progress towards, and recoveries from diseases. Such biometric monitoring devices may have sensors and run algorithms accordingly to measure and calculate biometric signals such as heart rate, heart rate variability, steps taken, calories burned, distance traveled, weight and body fat, activity intensity, activity duration and frequency, etc. In addition to the measured biometric signals, food intake logs provided by users may be used.

In one embodiment, a biometric monitoring device may observe heart rate and its changes over time, especially before and after a food intake event or events. It is known that heart rate is affected by blood sugar level, whereas it is well known that high blood sugar level is a pre-diabetic condition. Thus, mathematical models that describe the relation between time elapsed (after food intake) and blood sugar level may be found via statistical regression, where data are collected from normal, pre-diabetic, and diabetic individuals to provide respective mathematical models. With the mathematical models, one may predict whether an individual with specific heart rate patterns is healthy, pre-diabetic, or diabetic.

Knowing that many heart failures are associated with pre-diabetic or diabetic conditions, it is possible to further inform users of biometric monitoring devices with possible heart failures, e.g., coronary heart disease, cerebrovascular disease and peripheral vascular disease etc., of such risks based on their biometric data.

Users' activity intensity, type, duration, and frequency may also be taken into account, when developing the mathematical models, as an argument that controls "probability" of the disease onset, using recommended exercise guidelines such as guidelines provided by American Heart Association (http://www.heart.org/). Many guidelines on nutrition and weight management are also available in academia and to the general public to prevent cardiovascular and diabetic disease. Such guidelines may be incorporated into the mathematical models with the user data accumulated over time, such as ingredients of the food that the users consumed, and weight and body fat trends.

If users have set their family members as their friends on a social network site, which stores and displays biometric data, the likelihood of the family members getting a disease may also be analyzed and the users informed of the results.

In addition to informing users regarding a potential development of disease, recommended life-style including exercise regime and recipes with healthier ingredients and methods of preparation may be provided to the users.

Sport Metric Acquisition Using a Sensor Device

In some embodiments, a sensor may be mounted on a racket, e.g., tennis racket, to help to measure the different strokes of the player. This may be applicable to most, if not all, racket sports including, but not limited to, tennis, racquetball, squash, table tennis, badminton, lacrosse, etc., as well as sports played with a bat like baseball, softball, cricket, etc. Similar techniques may also be used to measure different aspects of golf. Such a device can be mounted on the base of the racket, on the handle or on the shock absorber typically mounted on the strings. This device may have various sensors like an accelerometer, gyroscope, magnetometer, strain sensor, and/or microphone. The data from these sensors may either be stored locally or transmitted wirelessly to a host system on a smartphone or other wireless receiver.

In some embodiments of a biometric monitoring device, a wrist mounted biometric monitoring device including an accelerometer, gyroscope, magnetometer, microphone, etc. may perform similar analysis of the user's game or motions. This biometric monitoring device may take the form of a watch or other band worn on the user's wrist. Racket- or bat-mounted sensors that measure or detect the moment of impact between the bat or racket and the ball and wirelessly transmit such data to the wrist-mounted biometric monitoring device may be used to improve accuracy of such algorithms by accurately measuring the time of impact with the ball.

Both wrist and racket-/bat-mounted devices may help measure different aspects of the user's game including, but not limited to, stroke-type (forehand, backhand, serve, slice, etc.), number of forehands, number of backhands, ball spin direction, topspin, service percentage, angular velocity of racket head, backswing, shot power, shot consistency, etc. The microphone or the strain sensor may be used in addition to the accelerometer to identify the moment at which the ball impacts the racket/bat. In cricket and baseball, such a device may measure the backswing, the angular velocity of the bat at the time of impact, the number of shots on the off-side vs. leg-side (cricket). It may also measure the number of swings and misses and the number of defensive vs. offensive strokes. Such a device may also have a wireless transmitter to transmit such statistics in real time to a scoreboard or to individual devices held by spectators.

The wrist- or racket-mounted device may have a small number of buttons (e.g., two) that may be used by the player to indicate when a volley is won or when an unforced error occurs. This will allow the algorithm to calculate the fraction of winners and unforced errors that are forehands vs. backhands. The algorithm may also keep track of the number of aces vs. double-faults in tennis. If both players use such a system, the system may also automatically keep track of the score.

Indirect Metric Estimation

Bicycle computers typically measure a variety of metrics including, but not limited to, speed, cadence, power, and wind speed. In the case that the portable monitoring device does not measure these metrics or is not in communication with devices which may be able to supply these metrics, these and other metrics may be inferred using the sensors that the portable biometric monitoring device does have. In one embodiment, the portable biometric monitoring device may measure heart rate. It may use this measurement to infer/estimate the amount of power that the user is outputting. Other metrics such as the user's age, height, and weight may help inform the power measurement. Additional sensor data such as GPS-measured speed, altitude gain/descent, bicycle attitude (so as the measure the incline or decline of a slope), and accelerometer signals may be used to further inform the power estimate. In one embodiment, an approximately linear relationship between heart rate and power output may be used to calculate the user's power output.

In one embodiment, a calibration phase may occur where the user takes data from the portable biometric monitoring device and a secondary device that may be used during calibration as a baseline but not be used at a later time (e.g., a power meter). This may allow a relationship between sensor data measured by the portable monitoring device and sensor data measured by the secondary device data to be determined. This relationship may then be used when the secondary device is not present to calculate estimated values of data that is explicitly provided by the secondary device but not by the biometric monitoring device.

Activity Based Automatic Scheduling

In one embodiment, the day's travel requirements (to work, from work, between meetings) may be scheduled for the user based on the information in their calendar (or emails or text messages etc.), with the aim of meeting daily activity goal(s) or long term activity goal(s). The user's historical data may be used to help plan both meeting the goal(s) and also the transit time required. This feature may be combined with friends or colleagues. The scheduling may be done such that a user may meet a friend along the way as they walk to work, or meet a colleague on the way to a meeting (the user might need to set a rendezvous point, though). If there is real-time communication between biometric monitoring devices of the user and the user's friend, the user may be directed to walk a longer route if data from the friend's biometric monitoring device indicates that their friend is running late.

In another embodiment, walking/running/fitness routes may be suggested to the user based (in whole or in part) on their proximity to the user. The data for such recommendations could also or additionally be based on GPS info from other users. If there is real-time communication, the user may be directed to a busy route or a quiet route as preferred. Knowing heart rate and basic fitness information about other users may allow the system to suggest a route to match a user's fitness level and the desired exercise/exertion level. Again this information may be used for planning/guiding a user to longer term activity/fitness goals.

Location/Context Sensing and Applications

Through one or more methods, embodiments of the biometric monitoring devices disclosed herein may have sensors that can determine or estimate the location and or context (e.g. in a bus, at home, in a car) of the biometric monitoring device. Purpose-built location sensors such as GPS, GLONASS, or other GNSS (Global Navigation Satellite System) sensors may be used. Alternatively, location may be inferred, estimated or guessed using less precise sensors. In some embodiments in which it is difficult to know the user's location, user input may aid in the determination of their location and or context. For example, if sensor data makes it difficult to determine if a user was in a car or a bus, the biometric monitoring device or a portable communication device in communication with the biometric monitoring device or a cloud server which is in communication with the biometric monitoring device may present a query to the user asking them if they took the bus today or took a car. Similar queries may occur for locations other than vehicular contexts. For example, if sensor data indicate that the user completed a vigorous workout, but there is no location data that indicates that the user went to a gym, the user may be asked if they went to the gym today.

Vehicular Transportation Detection

In some embodiments, sensors of the biometric monitoring device and/or a portable electronic device in communication with the biometric monitoring device and/or a server which communicates with the biometric monitoring device may be used to determine what type of vehicle (if any) the user is, or was, in. Note that in the embodiments below, a sensor in one or more biometric monitoring devices and/or portable electronic devices may be used to sense the relevant signal. Also note that while specific network protocols such as WiFi or Bluetooth may be used in the following descriptions, one or more alternative protocols such as RFID, NFC, or cellular telephony may also be used.

In one embodiment, the detection of a Bluetooth device associated with a vehicle may be used to infer that the user is in a vehicle. For example, a user may have a car that has a Bluetooth multimedia system. When the user gets close enough to their car for a long enough period of time, the sensor device may recognize the Bluetooth identification of the multimedia system and assume that the user is in the car. Data from other sensors may be used to corroborate the assumption that the user is in the vehicle. Examples of data or signals from other sensors that may be used to confirm that the user is in a car include a GPS speed measurement that is higher than 30 mph and accelerometer signals that are characteristic of being in a car. Information intrinsic to the Bluetooth ID may be used to determine that it is a Wi-Fi router of a vehicle or type of vehicle. For example, the Bluetooth ID of a router in a car may be "Audi In-Car Multimedia." The keyword "Audi" or "Car" may be used to guess that the router is associated with a vehicle type of "car." Alternatively, a database of Bluetooth ID's and their associated vehicles may be used.

In one embodiment, a database of Bluetooth ID's and their associated vehicles may be created or updated by the user of a biometric monitoring device or through portable communication device data. This may be done with and/or without the aid of user input. In one embodiment if a biometric monitoring device can determine whether or not it is in a vehicle, vehicle type, or specific vehicle without the use of Bluetooth ID, and it encounters a Bluetooth ID that moves with the vehicle, it may send the Bluetooth ID and information regarding the vehicle to a central database to be catalogued as a Bluetooth ID that corresponds with a vehicle. Alternatively, if a user inputs information about the vehicle they are in or were in at a previous point in time and there is a Bluetooth ID that was encountered during or close to the time that the user indicated they were in the vehicle, the Bluetooth ID and vehicle information may be sent to a central database and associated with one another.

In another embodiment, the detection of a Wi-Fi device associated with a vehicle may be used to infer that the user is in that vehicle or type of vehicle. Some trains, buses, airplanes, cars, and other vehicles have Wi-Fi routers in them. The SSID of the router may be detected and used to infer or aid an inference that a user is in a specific vehicle or type of vehicle.

In one embodiment, a database of SSID's and their associated vehicles may be created or updated with the user of a biometric monitoring device or through portable communication device data. This may be done with and/or without the aid of user input. In one embodiment, if a biometric monitoring device can determine whether or not it is in a vehicle, vehicle type, or specific vehicle without the use of an SSID, and it encounters an SSID that moves with the vehicle, the biometric monitoring device may send the SSID and information regarding the vehicle to a central database to be catalogued as an SSID that corresponds with a vehicle. Alternatively, if a user inputs information about the vehicle they are in or were in at a previous point in time and there is an SSID that was encountered during or close to the time that the user indicated they were in the vehicle, the SSID and vehicle information may be sent to a central database and associated with one another.

In another embodiment of a biometric monitoring device, location sensors may be used to determine the track of a user. This track may then be compared to a database of routes for different modes of transit. Modes of transit may include, but are not limited to walking, running, biking, driving, taking a bus, taking a train, taking a tram, taking the subway, and/or motorcycling. If the user's track corresponds well with a route of a specific mode of transit, it may be assumed that the user used that mode of transit for the period of time that it took them to traverse the route. Note that the speed with which the route or sections of the route were completed may improve the guess of the mode of transit. For example, a bus and a car may both be able to take the same route, but the additional stopping of the bus at bus stops may allow the device to determine that the user was taking a bus rather than a car. Similarly, the discrimination between biking and driving a route may be aided by the typical difference of speed between the two. This difference in speed may also depend on the time of day. For example, some routes may be slower by car during rush hour.

In another embodiment, a biometric monitoring device may be able to detect that the user is in or near a vehicle based on measurements of the magnetic field of vehicle. In some embodiments, the magnetic field signature of a location typically associated with the vehicle (e.g., train station, subway station, bus stop, car garage) may also be used to infer that the user is currently in, will be, or has been in a vehicle. The magnetic field signature may be time invariant or time varying.

If it is determined that the user was indeed in a vehicle for a period of time, other metrics about the user may be modified to reflect such a status. In the case that the biometric monitoring device and/or portable electronic device can measure activity metrics such as steps taken, distance walked or run, altitude climbed, and/or calories burned, these metrics may be modified based on information about vehicular travel. If any steps taken or altitude climbed were incorrectly logged during the time that the user is in a vehicle, they may be removed from the log of metrics about the user. Metrics derived from the incorrectly logged steps taken or altitude climbed such as distance travelled and calories burned may also be removed from the log of metrics about the user. In the case that it can be determined in real-time or near real-time whether or not the user is in a vehicle, the sensors detecting metrics which should not be measured while in a vehicle (e.g. steps taken, stairs climbed) may be turned off or algorithms which are used to measure these metrics may be turned off to prevent incorrectly logged metrics (as well to save power). Note that metrics regarding vehicle use such as type of vehicle taken, when it was taken, which route was taken, and how long the trip took may be recorded and used later to present the user with this data and/or to correct other activity and physiological metrics about the user.

Location Sensing Using Bluetooth

Methods similar to those described above may also be used by a biometric monitoring device to determine when the user comes into proximity of static locations. In one embodiment, Bluetooth ID's from computers (e.g., tablet computers) at restaurants or stores may be used to determine the user's location. In another embodiment, semi-fixed Bluetooth ID's from portable communication devices (e.g., smartphones) may be used to determine a user's location. In the case of semi-fixed Bluetooth ID sources, multiple Bluetooth ID's may be need to reach an acceptable level of confidence of the location of the user. For example, a database of Bluetooth ID's of the coworkers of a user may be created. If the user is within range of several of these Bluetooth ID's during typical working hours, it may be assumed that the user is at work. The detection of other Bluetooth ID's may also be used to record when two users meet up. For example, it may be determined that a user went for a run with another user by analyzing pedometer data and Bluetooth ID's. Similar such concepts are discussed in further detail in U.S. Provisional Patent Application No. 61/948,468, filed Mar. 5, 2014, and previously incorporated by reference with regard to such concepts.

Uncertainty Metric for GPS Based on Location

When fusing sensor signals with GPS signal to estimate informative biometrics, such as steps, live pace, speed, or trajectory of trips, quality of the GPS signal is often very informative. However, GPS signal quality is known to be time-varying, and one of the factors that affects the signal quality is environmental surroundings.

Location information may be used to estimate GPS signal quality. A server may store a map of area types, where the area types are pre-determined by number and kind of objects that deteriorate GPS signals. The types may, for example, be: large building area, small building area, open area, side-by-water area, and forested area. These area types are then queried when GPS sensor gets turned on with its very first few location estimates, which are expected to be rough and inaccurate. With the rough GPS estimates of the location, possible types of areas may be returned, and these area types may then be taken into account in the calculation of the GPS signal quality and reliability.

For example, if a user is in or near an urban canyon (an area surround by tall buildings) such as downtown San Francisco, a low certainty may be associated with any GNSS location measurements. This certainty may be used later by algorithms that attempt to determine the user's track, speed, and/or elevation based on, at least in part, GPS data.

In one embodiment, a database of location and GPS signal quality may be created automatically using data from one or more GNSS sensors. This may be automatically performed by comparing the GNSS tracks with a map of streets and seeing when the GNSS sensors show characteristics of a user travelling along a street (e.g., having a speed of 10 mph or higher), but their track is not located on a road. The database of GPS certainty based on approximate location may also be inferred from maps showing where there are tall buildings, canyons, or dense forests.

Location Sensing Using Vehicular GNSS and/or Dead Reckoning

Many vehicles have integrated GNSS navigation systems. Users of vehicles that don't have integrated GNSS navigations systems often buy a GNSS navigation system for their car that is typically mounted non-permanently in the driver's field of view. In one embodiment, a portable biometric monitoring device may be able to communicate with the vehicle's GNSS system. In the case where the portable biometric monitoring device is also used to track location, it may receive location information from the vehicle GNSS. This may enable the biometric monitoring device to turn off its own GNSS sensor (in the case that it has one), therefore reducing its power consumption.

In addition to GNSS location detection, a vehicle may be able to transmit data about its steering wheel orientation and/or its orientation with respect to the earth's magnetic field in addition to its speed as measured using the tire size and tire rotational velocity. This information may be used to perform dead-reckoning to determine a track and/or location in the case that the vehicle does not have a GNSS system or the vehicle's GNSS system cannot get a reliable location measurement. Dead-reckoning location information may supplement GNSS sensor data from the biometric monitoring device. For example, the biometric monitoring device may reduce the frequency with which it samples GNSS data and fill in the gap between GNSS location data with locations determined through dead reckoning.

Step counter data fusion with satellite-based location determination

In some implementations of a biometric monitoring device, data from various different sensors may be fused together to provide new insights as to activities of the wearer of the biometric monitoring device. For example, data from an altimeter in the biometric monitoring device may be combined with step count data obtained by performing peak detection analysis on accelerometer data from an accelerometer of the biometric monitoring device to determine when the wearer of the biometric monitoring device is, for example, climbing stairs or walking uphill (as opposed to riding an elevator or an escalator or walking across flat ground).

In another example of sensor data fusion, data from a step counter such as that discussed above may be combined with distance measurements derived from GPS data to provide a refined estimate of total distance traveled within a given window. For example, GPS-based distance or speed data may be combined with step-counter-based distance or speed (using steps taken multiplied by stride length, for example) using a Kalman filter in order to obtain a refined distance estimate that may be more accurate than either the GPS-based distance or speed measurement or the step-counter-based distance or speed measurement alone. In another implementation, a GPS-based distance measurement may be filtered using a smoothing constant that is a function of the step rate as measured by, for example, an accelerometer. Such implementations are discussed further in U.S. Provisional Patent Application No. 61/973,614, filed Apr. 1, 2014, which was previously incorporated herein by reference in the "Cross-Reference to Related Applications" section and which is again hereby incorporated by reference with respect to content directed at distance or speed estimation refinement using data from satellite-based location systems and step count sensors.

Biometric and Environmental/Exercise Performance Correlation

Some embodiments of portable monitoring devices described herein may detect a variety of data including biometric data, environmental data, and activity data. All of this data may be analyzed or presented to a user to facilitate analysis of or correlation between two or more types of data. In one embodiment, a user's heart rate may be correlated to car speed, biking speed, running speed, swimming speed or walking speed. For example, the user may be presented with a graph that plots biking speed on the X axis and heart rate on the Y axis. In another example, a user's heart rate may be correlated to music that they were listening to. The biometric monitoring device may receive data regarding what music the user was listening to through a wireless connection (e.g., Bluetooth) to a car radio. In another embodiment, the biometric monitoring device may also function as a music player itself, and therefore can record which song was played when.

UV Exposure Detection

In one embodiment, the biometric monitoring device may have the ability to monitor an individual's exposure to UV radiation. UVA and UVB may be measured with one or multiple sensors. For example, a photodiode having a bandpass filter which passes only UVA may detect UVA exposure and a photodiode having a bandpass filter which passes only UVB may detect UVB exposure. The user's skin pigmentation may also be measured using a camera or reflectometer (light emitter and light detector which determines the efficiency with which light is reflected off the skin). Using UVA, UVB, and skin pigmentation data, the biometric monitoring device may provide a user with information regarding the amount of UV exposure they have been subjected to. The biometric monitoring device may also provide estimates or alarms regarding over exposure to UV, potential for sunburn, and potential for increasing their risk of skin cancer.

Screen Power Saving Using User Presence Sensors

The portable biometric monitoring device may have one or more a displays to present information to the user. In one embodiment sensors on the biometric monitoring device may determine the user is using the biometric monitoring device and/or wearing the biometric monitoring device to determine the state of the display. For example, a biometric monitoring device having a PPG sensor may use the PPG sensor as a proximity sensor to determine when the user is wearing the biometric monitoring device. If the user is wearing the biometric monitoring device, the state of the screen (e.g. a color LCD screen) may be changed to "on" or "standby" from its typical state of being off.

Power Conservation with Respect to Satellite-Based Location Determination Systems In some implementations, certain systems included in a biometric monitoring device may consume relatively large amounts of power compared to other systems in the biometric monitoring device. Due to the small space constraints of many biometric monitoring devices, this may seriously affect overall battery charge life for the biometric monitoring device. For example, in some biometric monitoring devices, a satellite-based location determination system may be included. Each time the satellite-based location determination system is used to obtain a position fix using data from the GPS satellite constellation, it uses power drawn from the biometric monitoring device battery. The biometric monitoring device may be configured to alter the frequency with which the satellite-based location determination system obtains a location fix based on data from one or more sensors of the biometric monitoring device. This adaptive location fix frequency functionality may help conserve power while still allowing the satellite-based location determination system to provide location fixes at useful intervals (when appropriate).

For example, if a biometric monitoring device has an ambient light sensor, data from the ambient light sensor may be used to determine whether the lighting conditions indicate that the biometric monitoring device is likely indoors as opposed to outdoors. If indoors, the biometric monitoring device may cause the location fix frequency to be set to a level that is lower than the location fix frequency that may be used when the lighting conditions appear to indicate that the biometric monitoring device is outdoors. This has the effect of decreasing the number of location fixes that are attempted when the biometric monitoring device is indoors and thus less likely to obtain a good location fix using a satellite-based location determination system.

In another example, if motion sensors of the biometric monitoring device indicate that the wearer of the biometric monitoring device is substantially stationary, e.g., sleeping or generally not moving more than a few feet every minute, the location fix frequency of the satellite-based location determination system may be set to a lower level than if the motion sensors indicate that the wearer of the biometric monitoring device is in motion, e.g., walking or running from one location to another, e.g., moving more than a few feet.

In yet another example, the biometric monitoring device may be configured to determine if the biometric monitoring device is actually being worn by a person-if not, the biometric monitoring device may set the location fix frequency to a lower level than if the biometric monitoring device is actually being worn. Such determinations regarding whether or not the biometric monitoring device is being worn may be made, for example, when motion data collected from motion sensors of the biometric monitoring device indicate that the biometric monitoring device is substantially immobile, e.g., not even demonstrating small movements experienced by biometric monitoring devices when the wearer is sleeping or sedentary, or when data, for example, from a pulse waveform sensor indicates that no heart rate is detected. For optical pulse waveform sensors, if there is little or no change in the amount of light detected by the light detection sensor when the light source is turned on and off, this may be indicative of the fact that the pulse waveform sensor is not pressed against a person's skin and that, by inference, the biometric monitoring device is not being worn. Such adaptive satellite-based location determination system fix frequency concepts are discussed in more detail in U.S. Provisional Patent Application No. 61/955,045, filed Mar. 18, 2014, which was previously incorporated herein by reference in the "Cross-Reference to Related Applications" section and which is again hereby incorporated by reference with respect to content directed at power conservation in the context of satellite-based location determination systems.

It is to be understood that biometric monitoring devices, in addition to including the features discussed below in more detail, may also include one or more features or functionalities discussed above or discussed in the various applications incorporated by reference in the above discussion. Such implementations are to be understood as being within the scope of this disclosure.

There are many concepts and embodiments described and illustrated herein. While certain embodiments, features, attributes, and advantages have been described and illustrated herein, it should be understood that many others, as well as different and/or similar embodiments, features, attributes and advantages are apparent from the description and illustrations. As such, the above embodiments are merely provided by way of example. They are not intended to be exhaustive or to limit this disclosure to the precise forms, techniques, materials and/or configurations disclosed. Many modifications and variations are possible in light of this disclosure. It is to be understood that other embodiments may be utilized and operational changes may be made without departing from the scope of the present disclosure. As such, the scope of the disclosure is not limited solely to the description above because the descriptions of the above embodiments have been presented for the purposes of illustration and description.

Importantly, the present disclosure is neither limited to any single aspect nor embodiment, nor to any combinations and/or permutations of such aspects and/or embodiments. Moreover, each of the aspects of the present disclosure, and/or embodiments thereof, may be employed alone or in combination with one or more of the other aspects and/or embodiments thereof. For the sake of brevity, many of those permutations and combinations will not be discussed and/or illustrated separately herein.

The invention claimed is:

1. A biometric monitoring device for measuring blood pressure comprising:
   a wearable fixing structure configured to attach to a user and/or a user's apparel;

a motion sensor operable to detect motion of the user of the biometric monitoring device;

a photoplethysmogram (PPG) sensor to generate PPG sensor data; and one or more processors configured to:
obtain motion data from the motion sensor,
obtain the PPG sensor data from the PPG sensor,
obtain a plurality of pulse waveforms based, at least in part, on the PPG data, and
determine one or more features of a pulse waveform derived from the PPG sensor data, and/or transmit the PPG sensor data to a device configured to determine the one or more features of the pulse waveform from the PPG sensor data, the one or more features being related to blood pressure, via one of a plurality of trained models for determining the one or more features selected for the user based on at least the motion data to obtain the one or more features for the user as an output of the selected model.

2. The biometric monitoring device of claim 1, the one or more processors further configured to:
filter the PPG sensor data using information obtained from the motion data.

3. The biometric monitoring device of claim 1, the one or more processors further configured to:
determine that one or more conditions for collecting pulse waveform data from the user are satisfied; and
trigger, based on the determination that the one or more conditions are satisfied, the PPG sensor to obtain the PPG sensor data.

4. The biometric monitoring device of claim 3, the one or more conditions comprising the user's activity or location.

5. The biometric monitoring device of claim 4, the one or more processors configured to determine that the motion data matches an activity profile for an activity comprising resistance training, aerobic exercising, endurance training, sitting, working, and sleeping.

6. The biometric monitoring device of claim 3, the one or more conditions comprising the motion data being indicative of the biometric monitoring device being still for a period of time.

7. The biometric monitoring device of claim 3, the triggering the PPG sensor to obtain the PPG sensor data comprising increasing a sampling rate in which the PPG sensor operates.

8. The biometric monitoring device of claim 1, the motion sensor comprising an inertial sensor, an accelerometer a gyroscopic sensor, a magnetometer, or a combination thereof.

9. The biometric monitoring device of claim 1, the one or more processors further configured to determine that the motion data matches an orientation profile.

10. The biometric monitoring device of claim 1, the obtaining the PPG sensor data from the PPG sensor being performed based on the one or more processors determining, from the motion data, that the biometric monitoring device has experienced movement below a movement threshold for a period of time and/or the motion data matches an orientation profile.

11. The biometric monitoring device of claim 1, the wearable fixing structure comprising a strap for attaching to the user's wrist.

12. The biometric monitoring device of claim 11, the biometric monitoring device configured to permit the PPG sensor to obtain the PPG sensor data from the user's ulnar and/or radial artery.

13. The biometric monitoring device of claim 1, further comprising a housing enclosing the motion sensor, the PPG sensor, and the one or more processors.

14. The biometric monitoring device of claim 1, the one or more processors further configured to trigger repeatedly obtaining the PPG sensor data for determining pulse waveforms, while the user wears the biometric monitoring device.

15. The biometric monitoring device of claim 14, the one or more processors configured to trigger obtaining the PPG sensor data for at least X pulse waveforms over a period of at most about Y seconds.

16. The biometric monitoring device of claim 14, the one or more processors configured to trigger obtaining the PPG sensor data for at least X pulse waveforms every day over a period of at least Y days.

17. The biometric monitoring device of claim 14, the one or more processors configured to trigger obtaining the PPG sensor data at a schedule based on activity types or locations of the user.

18. The biometric monitoring device of claim 1, the one or more processors further configured to analyze the pulse waveform to obtain an estimate of the user's blood pressure.

19. The biometric monitoring device of claim 18, the estimate of the user's blood pressure being correlated with pulse transit time and/or pulse wave velocity.

* * * * *